US012655191B2

(12) United States Patent
Lorenz et al.

(10) Patent No.: US 12,655,191 B2
(45) Date of Patent: Jun. 16, 2026

(54) TCR CONSTRUCTS SPECIFIC FOR EBV-DERIVED ANTIGENS

(71) Applicant: MAX-DELBRÜCK-CENTRUM FÜR MOLEKULARE MEDIZIN IN DER HELMHOLTZ-GEMEINSCHAFT, Berlin (DE)

(72) Inventors: Felix Lorenz, Berlin (DE); Krystyna Dudaniec, Szczecin (PL); Wolfgang Uckert, Berlin (DE)

(73) Assignee: MAX-DELBRÜCK-CENTRUM FÜR MOLEKULARE MEDIZIN IN DER HELMHOLTZ-GEMEINSCHAFT, Berlin (DE)

( * ) Notice: Subject to any disclaimer, the term of this patent is extended or adjusted under 35 U.S.C. 154(b) by 1146 days.

(21) Appl. No.: 17/638,985

(22) PCT Filed: Feb. 28, 2020

(86) PCT No.: PCT/EP2020/074065
§ 371 (c)(1),
(2) Date: Feb. 28, 2022

(87) PCT Pub. No.: WO2021/038031
PCT Pub. Date: Mar. 4, 2021

(65) Prior Publication Data
US 2022/0267407 A1 Aug. 25, 2022

(30) Foreign Application Priority Data
Aug. 30, 2019 (EP) ..................................... 19194724

(51) Int. Cl.
| | |
|---|---|
| C07K 14/725 | (2006.01) |
| A61K 40/11 | (2025.01) |
| A61K 40/32 | (2025.01) |
| A61K 40/46 | (2025.01) |
| A61P 31/22 | (2006.01) |
| C07K 14/705 | (2006.01) |
| C07K 14/74 | (2006.01) |
| C12N 5/0783 | (2010.01) |
| A61K 38/00 | (2006.01) |

(52) U.S. Cl.
CPC .......... *C07K 14/7051* (2013.01); *A61K 40/11* (2025.01); *A61K 40/32* (2025.01); *A61K 40/46* (2025.01); *A61P 31/22* (2018.01); *C07K 14/70539* (2013.01); *C12N 5/0636* (2013.01); *A61K 38/00* (2013.01); *A61K 2239/31* (2023.05); *A61K 2239/48* (2023.05)

(58) Field of Classification Search
CPC .......... C07K 14/7051; C07K 14/70539; A61K 40/32; A61K 40/46; A61K 39/12; C12N 5/0636; C12N 2510/00; A61P 35/00
See application file for complete search history.

(56) References Cited

U.S. PATENT DOCUMENTS

| | | | |
|---|---|---|---|
| 2003/0175300 A1 | 9/2003 | Rajiv et al. | |
| 2016/0289760 A1 | 10/2016 | Suzuki et al. | |
| 2017/0088895 A1* | 3/2017 | Han | C12Q 1/6883 |

FOREIGN PATENT DOCUMENTS

| | | |
|---|---|---|
| CN | 106632658 A | 5/2017 |
| CN | 110577590 A | 12/2019 |
| CN | 110627894 A | 12/2019 |
| EP | 3091074 | 11/2016 |
| WO | 2011039508 | 4/2011 |
| WO | 2012031132 A1 | 3/2012 |
| WO | 2012058460 A2 | 5/2012 |
| WO | 2014091034 A1 | 6/2014 |
| WO | 2015022520 | 2/2015 |
| WO | 2015075939 | 5/2015 |

(Continued)

OTHER PUBLICATIONS

RossJohn et al. T Cell Antigen Receptor Recognition of Antigen-Presenting Molecules.Annu. Rev. Immunol. 2015. 33:169-200 (Year: 2015).*
Song et al. Broad TCR repertoire and diverse structural solutions for recognition of an immunodominant CD8+ T cell epitope. vol. 24 No. Apr. 4, 2017 nature structural & molecular biology (Year: 2017).*
Extended European Search Report issued for Application No. 19194724.1, dated Jun. 26, 2020.
International Search report and Written Opinion issued for Application No. PCT/EP2020074065, dated Feb. 2, 2021, 29 pages.
Jurgens, Lisa A., et al. "Transduction of primary lymphocytes with Epstein-Barr virus (EBV) latent membrane protein-specific T-cell receptor induces lysis of virus-infected cells: a novel strategy for the treatment of Hodgkin's disease and nasopharyngeal carcinoma." Journal of clinical immunology 26.1 (2006): 22-32.

(Continued)

*Primary Examiner* — Daniel E Kolker
*Assistant Examiner* — Brian Hartnett
(74) *Attorney, Agent, or Firm* — Meunier Carlin & Curfman LLC

(57) ABSTRACT
The present invention relates to the filed of immunotherapy, in particular, of Epstein-Barr virus-associated diseases (EBV, also designated Human gammaherpesvirus 4), e.g., cancer or post-transplant lymphoproliferative disease, in particular, to adoptive T cell therapy or T cell receptor (TCR) gene therapy. The invention provides a combination of nucleic acids encoding at least two TCR constructs, or the respective proteins or host cells, wherein each TCR construct is capable of specifically binding to its respective epitope in the context of the respective MHC I, and wherein the epitopes are peptides from different antigens expressed by the same infective agent or cancer, e.g., EBV antigens. The invention also provides specific nucleic acids encoding a TCR alpha chain construct (TRA) and/or a TCR beta chain construct (TRB) of a TCR construct specific for an epitope in complex with a human MHC I, wherein the epitope is an epitope of an Epstein-Barr-virus protein, wherein the TCR constructs are specific for epitopes from LMP2A, LMP1 or EBNA3C. Proteins encoded by said nucleic acids, corresponding host cells and pharmaceutical compositions and kits are also objects of the invention.

Figures 2B, 3:
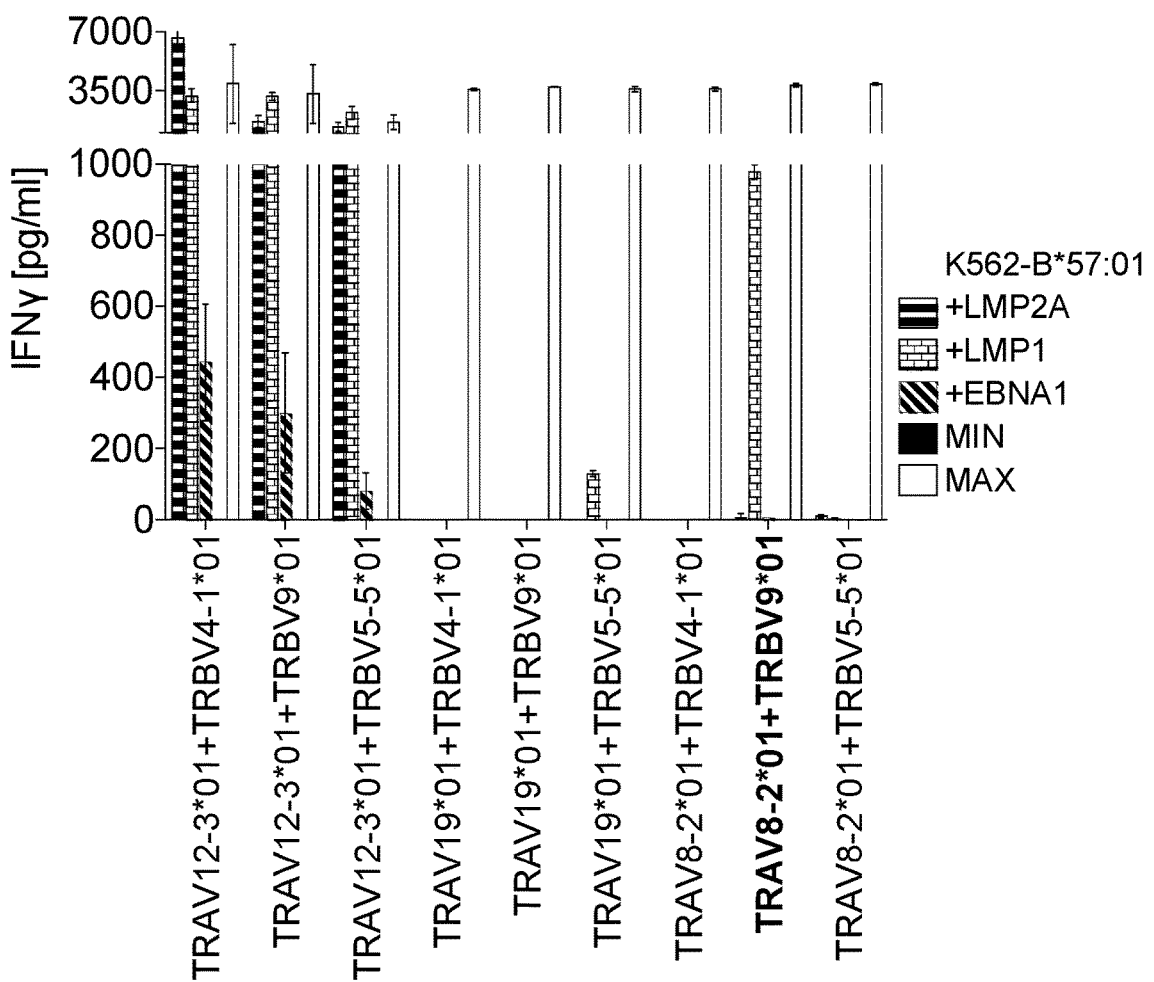

19 Claims, 22 Drawing Sheets
Specification includes a Sequence Listing.

(56) References Cited

FOREIGN PATENT DOCUMENTS

| | | | |
|---|---|---|---|
| WO | 2016022400 | A1 | 2/2016 |
| WO | 2016095783 | | 6/2016 |
| WO | 2016095783 | A1 | 6/2016 |
| WO | 2016191756 | A1 | 12/2016 |
| WO | 2016193299 | A1 | 12/2016 |
| WO | 2016201124 | | 12/2016 |
| WO | 2016203577 | A1 | 12/2016 |
| WO | 2017059084 | A1 | 4/2017 |
| WO | 2017084421 | A1 | 5/2017 |
| WO | 2017203356 | A1 | 11/2017 |
| WO | 2017203362 | A1 | 11/2017 |
| WO | 2018015810 | A2 | 1/2018 |
| WO | 2018026691 | A1 | 2/2018 |
| WO | 2018067618 | A1 | 4/2018 |
| WO | 2018129199 | A1 | 7/2018 |
| WO | 2018132479 | A1 | 7/2018 |
| WO | 2018136762 | A1 | 7/2018 |
| WO | 2018175585 | A1 | 9/2018 |
| WO | 2018218038 | A1 | 11/2018 |
| WO | 2019028406 | A2 | 2/2019 |
| WO | 2019031938 | A2 | 2/2019 |
| WO | 2019031939 | A2 | 2/2019 |
| WO | 2019036688 | A1 | 2/2019 |
| WO | 2019047932 | A1 | 3/2019 |
| WO | 2019067243 | A1 | 4/2019 |
| WO | 2019067805 | A1 | 4/2019 |
| WO | 2019070435 | A1 | 4/2019 |
| WO | 2019070541 | A1 | 4/2019 |
| WO | 2019103857 | A1 | 5/2019 |
| WO | 2019118902 | A2 | 6/2019 |
| WO | 2019147604 | A2 | 8/2019 |
| WO | 2019152743 | A1 | 8/2019 |
| WO | 2019161133 | A1 | 8/2019 |
| WO | 2019213184 | A1 | 11/2019 |
| WO | 2020018691 | A1 | 1/2020 |
| WO | 2020049496 | A1 | 3/2020 |
| WO | 2020055862 | A1 | 3/2020 |
| WO | 2020082130 | A1 | 4/2020 |
| WO | 2020097466 | A1 | 5/2020 |
| WO | 2020112815 | A1 | 6/2020 |
| WO | 2020118094 | A1 | 6/2020 |
| WO | 2020133050 | A1 | 7/2020 |
| WO | 2020162696 | A1 | 8/2020 |

OTHER PUBLICATIONS

Orentas, Rimas J., et al. "Retroviral transduction of a T cell receptor specific for an Epstein-Barr virus-encoded peptide." Clinical immunology 98.2 (2001): 220-228.
Database Geneseq [online] Jul. 16, 2015, "Human TCR TRAV2/TRAJ33 CDR3, SEQ ID 1454" XP002797031, 1 page.
Chervin, Adam S., et al. "Engineering higher affinity T cell receptors using a T cell display system." Journal of immunological methods 339.2 (2008): 175-184.
Cho, Hyun-Il, et al. "A novel Epstein-Barr virus-latent membrane protein-1-specific T-cell receptor for TCR gene therapy." British Journal of Cancer 118.4 (2018): 534-545.
Cohen, Cyrille J., et al. "Enhanced antitumor activity of murine-human hybrid T-cell receptor (TCR) in human lymphocytes is associated with improved pairing and TCR/CD3 stability." Cancer research 66.17 (2006): 8878-8886.

Cohen, Cyrille J., et al. "Enhanced antitumor activity of T cells engineered to express T-cell receptors with a second disulfide bond." Cancer research 67.8 (2007): 3898-3903.
Danska, Jayne S., et al. "The presumptive CDR3 regions of both T cell receptor alpha and beta chains determine T cell specificity for myoglobin peptides." The Journal of experimental medicine 172.1 (1990): 27-33.
Doran, Stacey L., et al. "T-cell receptor gene therapy for human papillomavirus-associated epithelial cancers: a first-in-human, phase I/II study." Journal of Clinical Oncology 37.30 (2019): 2759. doi: 10.1200/JCO.18.02424. [Epub ahead of print].
Engels, Boris, et al. "Retroviral vectors for high-level transgene expression in T lymphocytes." Human gene therapy 14.12 (2003): 1155-1168.
Garcia, K. Christopher, and Erin J. Adams. "How the T cell receptor sees antigen-a structural view." Cell 122.3 (2005): 333-336.
Hart, D. P., et al. "Retroviral transfer of a dominant TCR prevents surface expression of a large proportion of the endogenous TCR repertoire in human T cells." Gene therapy 15.8 (2008): 625-631.
Kuball, Jurgen, et al. "Facilitating matched pairing and expression of TCR chains introduced into human T cells." Blood 109.6 (2007): 2331-2338.
Leisegang, Matthias, et al. "Enhanced functionality of T cell receptor-redirected T cells is defined by the transgene cassette." Journal of molecular medicine 86.5 (2008): 573-583.
Linette, Gerald P., et al. "Cardiovascular toxicity and titin cross-reactivity of affinity-enhanced T cells in myeloma and melanoma." Blood, The Journal of the American Society of Hematology 122.6 (2013): 863-871.
Lorenz, Felix KM, et al. "Unbiased Identification of T-Cell Receptors Targeting Immunodominant Peptide-MHC Complexes for T-Cell Receptor Immunotherapy." Human gene therapy 28.12 (2017): 1158-1168.
Morgan, Richard A., et al. "Cancer regression and neurologic toxicity following anti-MAGE-A3 TCR gene therapy." Journal of immunotherapy (Hagerstown, Md.: 1997) 36.2 (2013): 133.
Robbins, Paul F., et al. "Single and dual amino acid substitutions in TCR CDRs can enhance antigen-specific T cell functions." The Journal of Immunology 180.9 (2008): 6116-6131.
Scholten, Kirsten BJ, et al. "Codon modification of T cell receptors allows enhanced functional expression in transgenic human T cells." Clinical Immunology 119.2 (2006): 135-145.
Simpson, Amy A., et al. "Structural and energetic evidence for highly peptide-specific tumor antigen targeting via allo-MHC restriction." Proceedings of the National Academy of Sciences 108.52 (2011): 21176-21181.
Sommermeyer, Daniel, and Wolfgang Uckert. "Minimal amino acid exchange in human TCR constant regions fosters improved function of TCR gene-modified T cells." The Journal of Immunology 184.11 (2010): 6223-6231.
Tran, Eric, et al. "Cancer immunotherapy based on mutation-specific CD4+ T cells in a patient with epithelial cancer." Science 344.6184 (2014): 641-645.
Yang, Dongchang, et al. "Evaluation of Epstein-Barr virus latent membrane protein 2 specific T-cell receptors driven by T-cell specific promoters using lentiviral vector." Clinical and Developmental Immunology 2011 (2011). Article ID 716926. https://doi.org/10.1155/2011/716926.
Zheng, Yong, et al. "Human leukocyte antigen (HLA) A* 1101-restricted Epstein-Barr virus-specific T-cell receptor gene transfer to target nasopharyngeal carcinoma." Cancer immunology research 3.10 (2015): 1138-1147.

* cited by examiner

Fig. 1
A
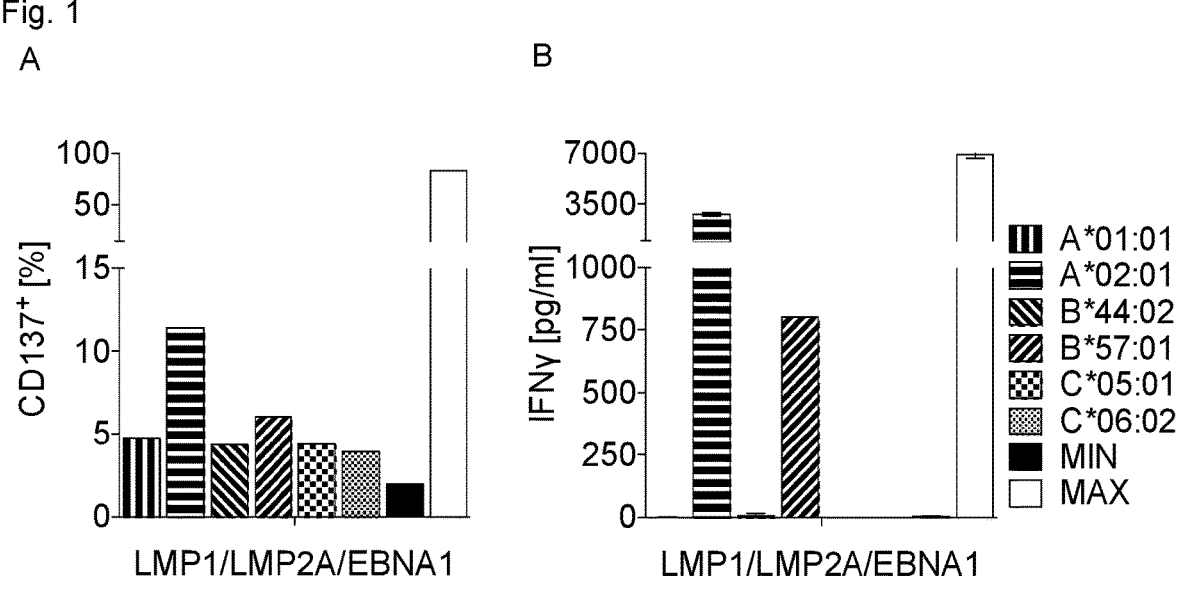
B
C
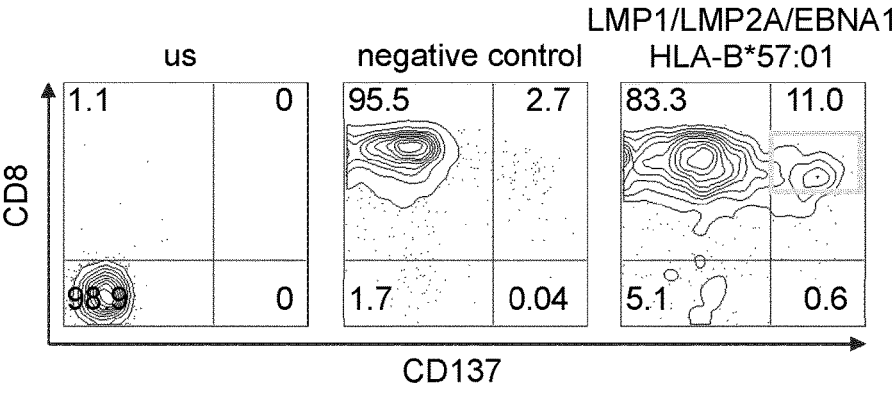
Fig. 2A
LMP1/LMP2A/EBNA1-HLA-B*57:01
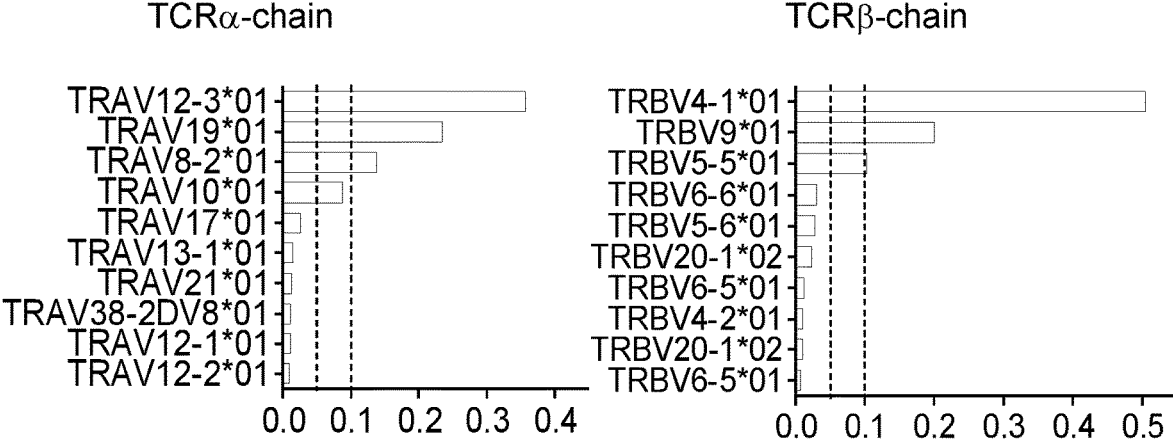

| TCR | EBV antigen-MHC combination | V segment | V segment frequency (%) | CDR-3 |
|---|---|---|---|---|
| TCR50 | LMP1/LMP2A/ EBNA1 HLA-B*57:01 | TRAV12-3*01 TRAV19*01 TRAV8-2*01 | 35.8 23.3 13.7 | AMSDLYAGNNRKLI ALTFLRDDKII VVMATGFQKLV |
| | | TRBV4-1*01 TRBV9*01 TRBV5-5*01 | 50.3 20.0 10.2 | ASSQDARVSGANVLT ASSVTSGSDEQF ASSFSLGHSYEQY |

| Truncated construct of LMP1 | Length (nt) |
|---|---|
| LMP1 (full length) | 1-1036 |
| LMP1/2 | 1-624 |
| LMP1/1 | 1-315 |

B

| Epitope | Length (-mer) | Affinity (nM) | Bind level |
|---|---|---|---|
| WTLLVDLLW | 9 | 12.25 | SB |
| IALYLQQNWW | 10 | 14.84 | SB |
| IALYLQQNW | 9 | 16.32 | SB |
| WWTLLVDLLW | 10 | 32.51 | SB |
| IIALYLQQNW | 10 | 57.84 | SB |
| WTLLVDLLWL | 10 | 111.95 | SB |
| LAILIWMYY | 9 | 231.02 | SB |
| LLFLAILIW | 9 | 234.00 | SB |
| LLLFLAILIW | 10 | 749.75 | WB |
| LAILIWMYYH | 10 | 789.96 | WB |
| ALYLQQNWW | 9 | 853.78 | WB |
| FLAILIWMYY | 10 | 1515.23 | WB |
| NSNEGRHHL | 9 | 12828.84 | WB |

Fig. 7
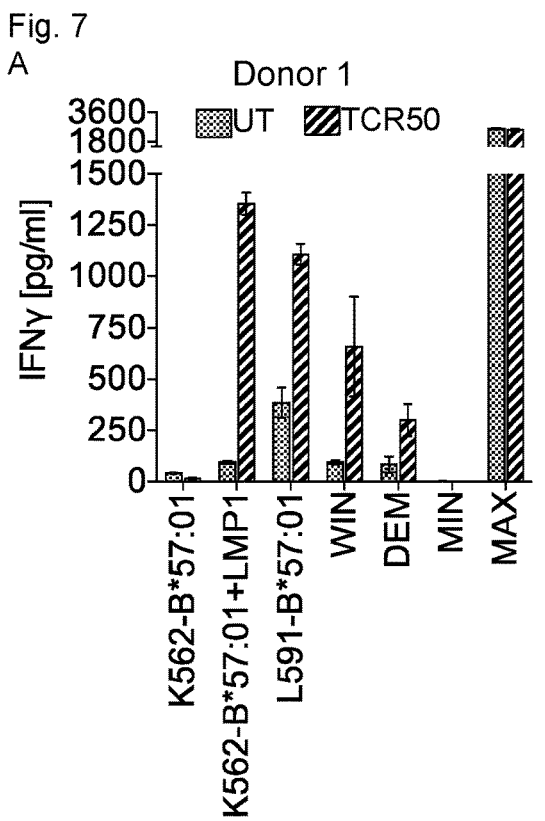
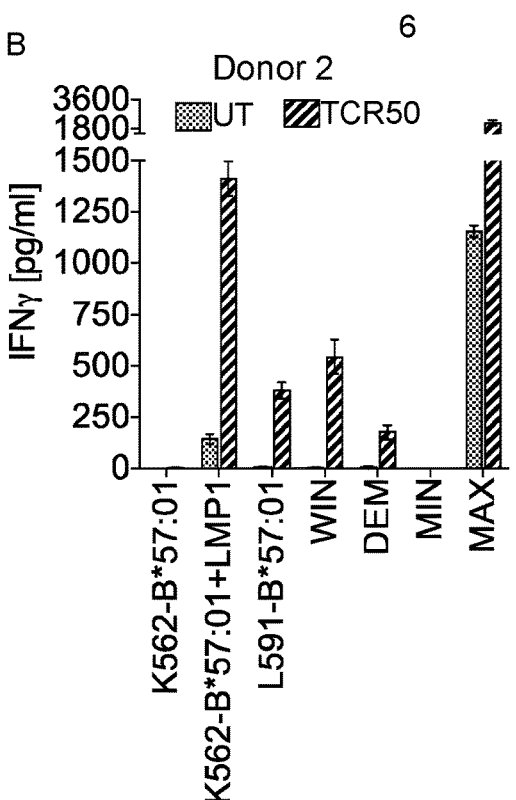
Fig. 8: TCR01 (EBNA3C)
A
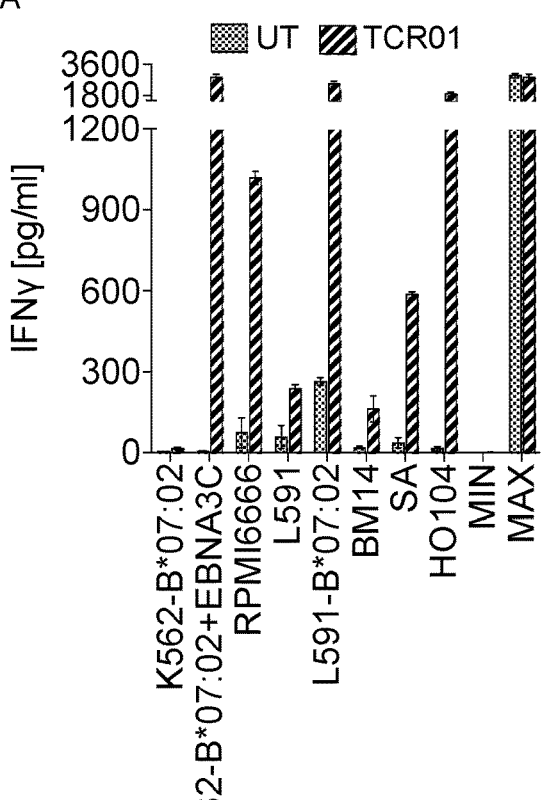
B
| Truncated construct of EBNA3C | Length (nt) |
| --- | --- |
| EBNA3C (full length) | 1-2979 |
| EBNA3C/3 | 1-2070 |
| EBNA3C/2 | 1-1569 |
| EBNA3C/1 | 1-567 |

Fig. 8: TCR01 (EBNA3C)

C

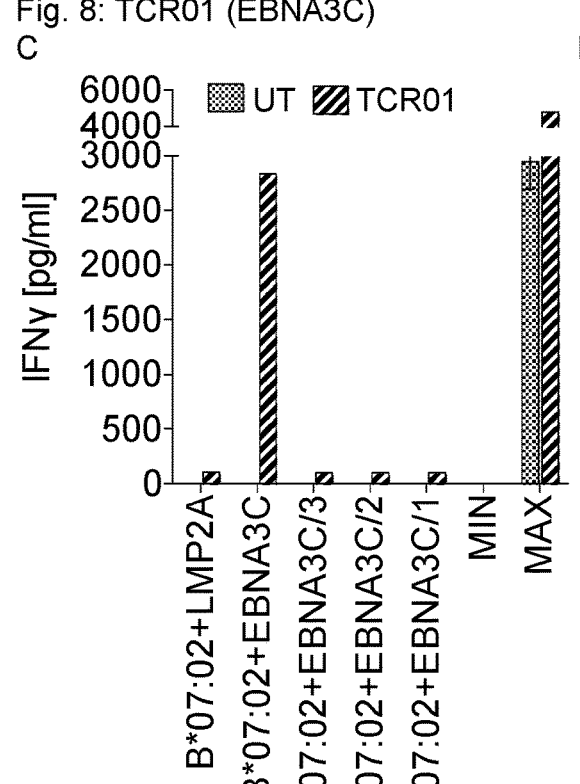

D

| Epitope | Length (-mer) | Affinity (nM) | Bind level |
|---|---|---|---|
| QPRAPIRPI | 9 | 8.88 | SB |
| RPIPTRFPPPPM | 12 | 11.25 | SB |
| RPRVEESSHGPA | 12 | 19.34 | SB |
| SPQPRAPI | 8 | 23.53 | SB |
| SPQPRAPIRPI | 11 | 39.61 | SB |
| SPQPRAPIRPIP | 12 | 96.46 | SB |
| PQPRAPIRPI | 10 | 100.18 | SB |
| QPRAPIRPIP | 10 | 102.53 | SB |
| PRAPIRPI | 8 | 110.41 | SB |
| APIRPIPTRF | 9 | 114.88 | SB |
| FPPPPMPL | 8 | 161.90 | WB |
| HGPARCSQAT | 10 | 196.24 | WB |
| RPIPTRFPP | 9 | 250.57 | WB |
| RPIPTRFP | 8 | 275.13 | WB |
| IPTRFPPPPMP | 11 | 321.08 | WB |
| PIPTRFPPPPM | 11 | 333.78 | WB |
| IPTRFPPPPMPL | 12 | 365.16 | WB |
| GPARCSQATA | 10 | 373.18 | WB |
| FPPPPMPLQDSM | 12 | 439.96 | WB |
| PPMPLQDSM | 9 | 507.20 | WB |
| RPIPTRFPPP | 10 | 858.94 | WB |
| MPLQDSMAVG | 10 | 895.50 | WB |
| PIPTRFPPPPMP | 12 | 923.80 | WB |
| PMPLQDSMAV | 10 | 985.94 | WB |
| PMPLQDSM | 8 | 1002.15 | WB |
| QPRAPIRPIPT | 11 | 1018.57 | WB |
| QPRAPIRP | 8 | 1397.58 | WB |

Fig. 8: TCR01 (EBNA3C)
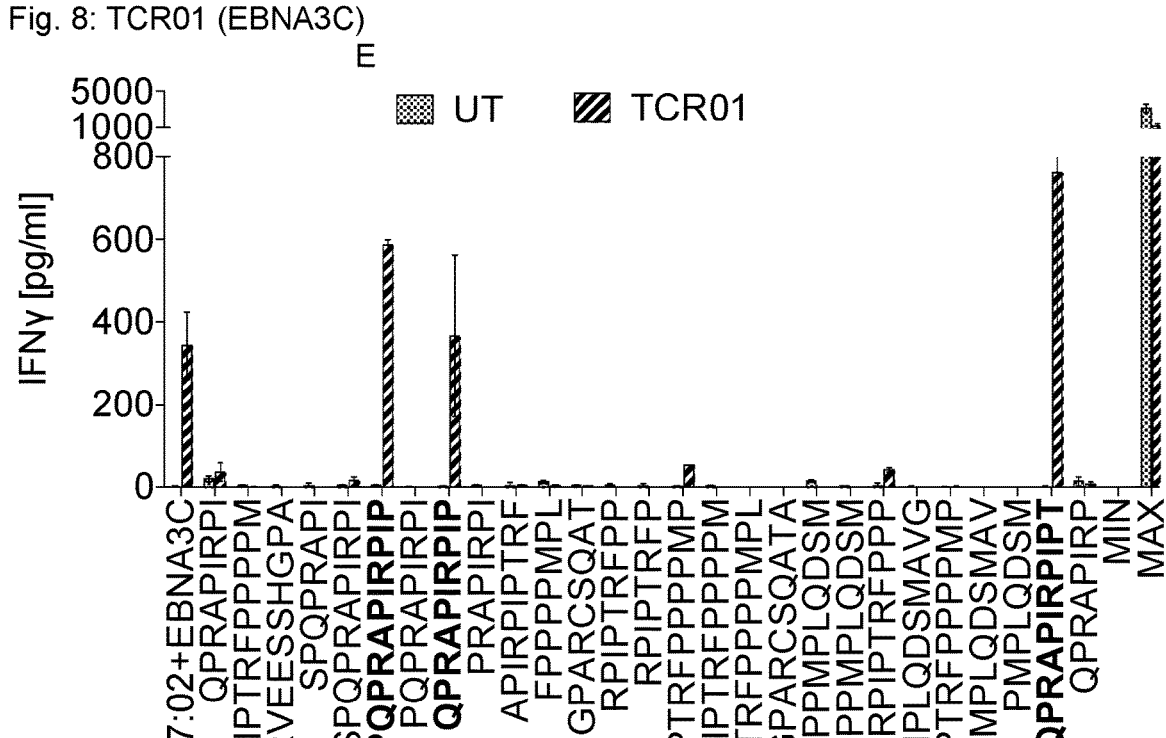
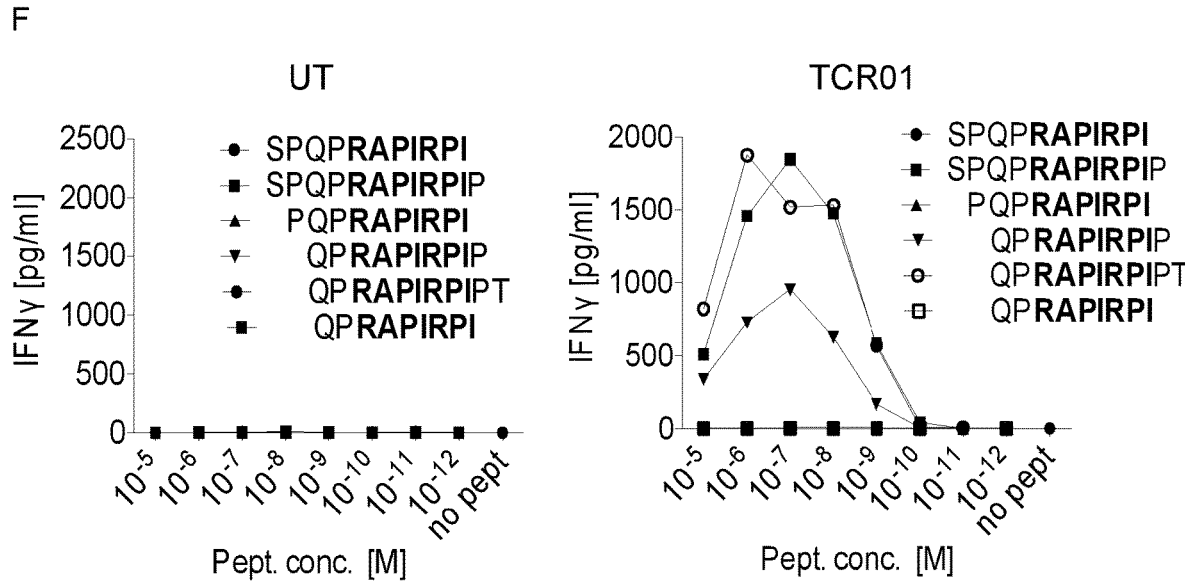

Fig. 9: TCR25 (EBNA3C)
A
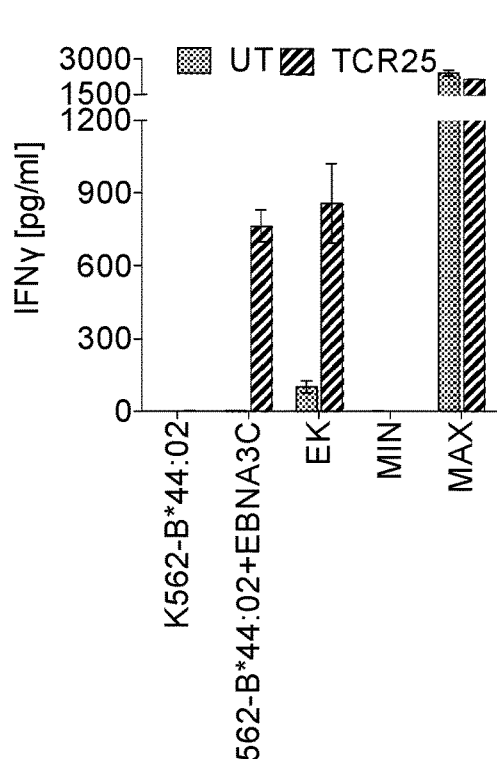
B
| Truncated construct of EBNA3C | Length (nt) |
|---|---|
| EBNA3C (full length) | 1-2979 |
| EBNA3C/3 | 1-2070 |
| EBNA3C/2 | 1-1569 |
| EBNA3C/1 | 1-567 |
C
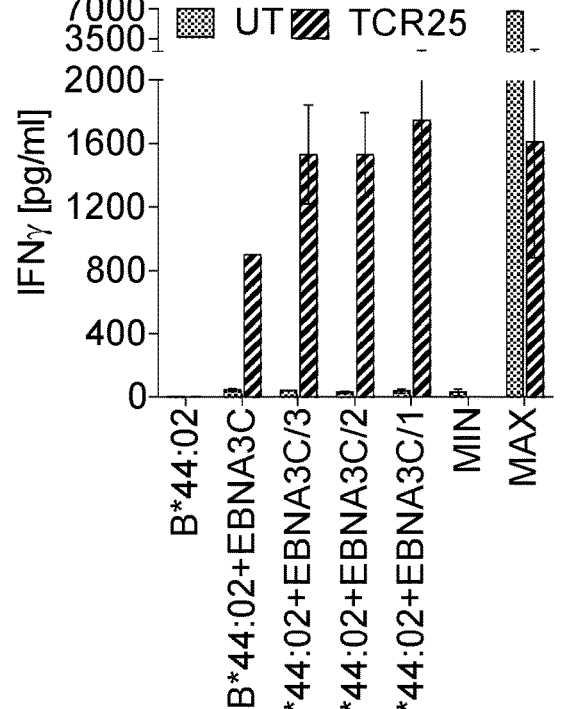
D
| Epitope | Length (-mer) | Affinity (nM) | Bind level |
|---|---|---|---|
| AEGGVGWRHW | 10 | 12.74 | SB |
| SERLVPEESY | 10 | 415.83 | WB |
| WLLTSPSQSW | 10 | 3285.78 | WB |
| LLTSPSQSW | 9 | 12269.12 | |

Fig. 9: TCR25 (EBNA3C)
E
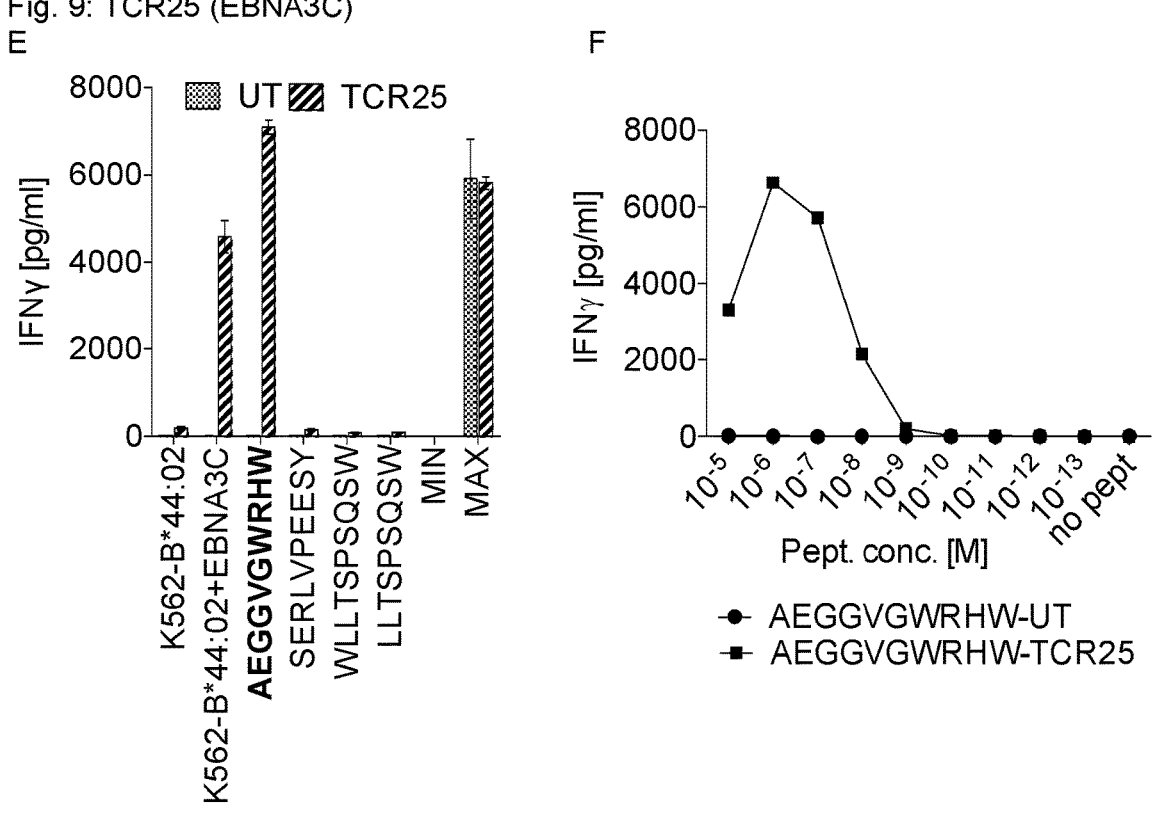
Fig. 10: TCR27 (EBNA3C)
A
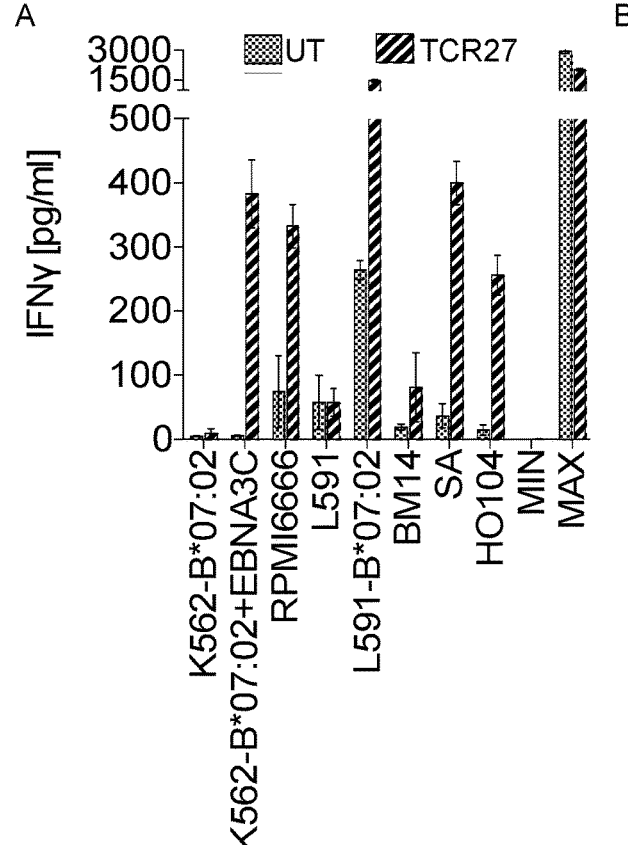
B
| Truncated construct of EBNA3C | Length (nt) |
|---|---|
| EBNA3C (full length) | 1-2979 |
| EBNA3C/3 | 1-2070 |
| EBNA3C/2 | 1-1569 |
| EBNA3C/1 | 1-567 |

Fig. 10: TCR27 (EBNA3C)

C

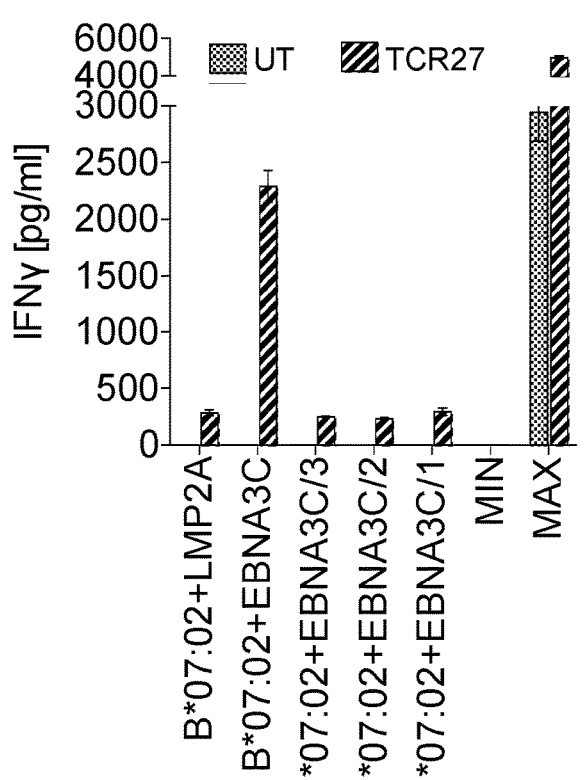

D

| Epitope | Length (-mer) | Affinity (nM) | Bind level |
|---|---|---|---|
| QPRAPIRPI | 9 | 8.88 | SB |
| RPIPTRFPPPPM | 12 | 11.25 | SB |
| RPRVEESSHGPA | 12 | 19.34 | SB |
| SPQPRAPI | 8 | 23.53 | SB |
| SPQPRAPIRPI | 11 | 39.61 | SB |
| SPQPRAPIRPIP | 12 | 96.46 | SB |
| PQPRAPIRPI | 10 | 100.18 | SB |
| QPRAPIRPIP | 10 | 102.53 | SB |
| PRAPIRPI | 8 | 110.41 | SB |
| APIRPIPTRF | 9 | 114.88 | SB |
| FPPPPMPL | 8 | 161.90 | WB |
| HGPARCSQAT | 10 | 196.24 | WB |
| RPIPTRFPP | 9 | 250.57 | WB |
| RPIPTRFP | 8 | 275.13 | WB |
| IPTRFPPPPMP | 11 | 321.08 | WB |
| PIPTRFPPPPM | 11 | 333.78 | WB |
| IPTRFPPPPMPL | 12 | 365.16 | WB |
| GPARCSQATA | 10 | 373.18 | WB |
| FPPPPMPLQDSM | 12 | 439.96 | WB |
| PPMPLQDSM | 9 | 507.20 | WB |
| RPIPTRFPPP | 10 | 858.94 | WB |
| MPLQDSMAVG | 10 | 895.50 | WB |
| PIPTRFPPPPMP | 12 | 923.80 | WB |
| PMPLQDSMAV | 10 | 985.94 | WB |
| PMPLQDSM | 8 | 1002.15 | WB |
| QPRAPIRPIPT | 11 | 1018.57 | WB |
| QPRAPIRP | 8 | 1397.58 | WB |

Fig. 10: TCR27 (EBNA3C)
E
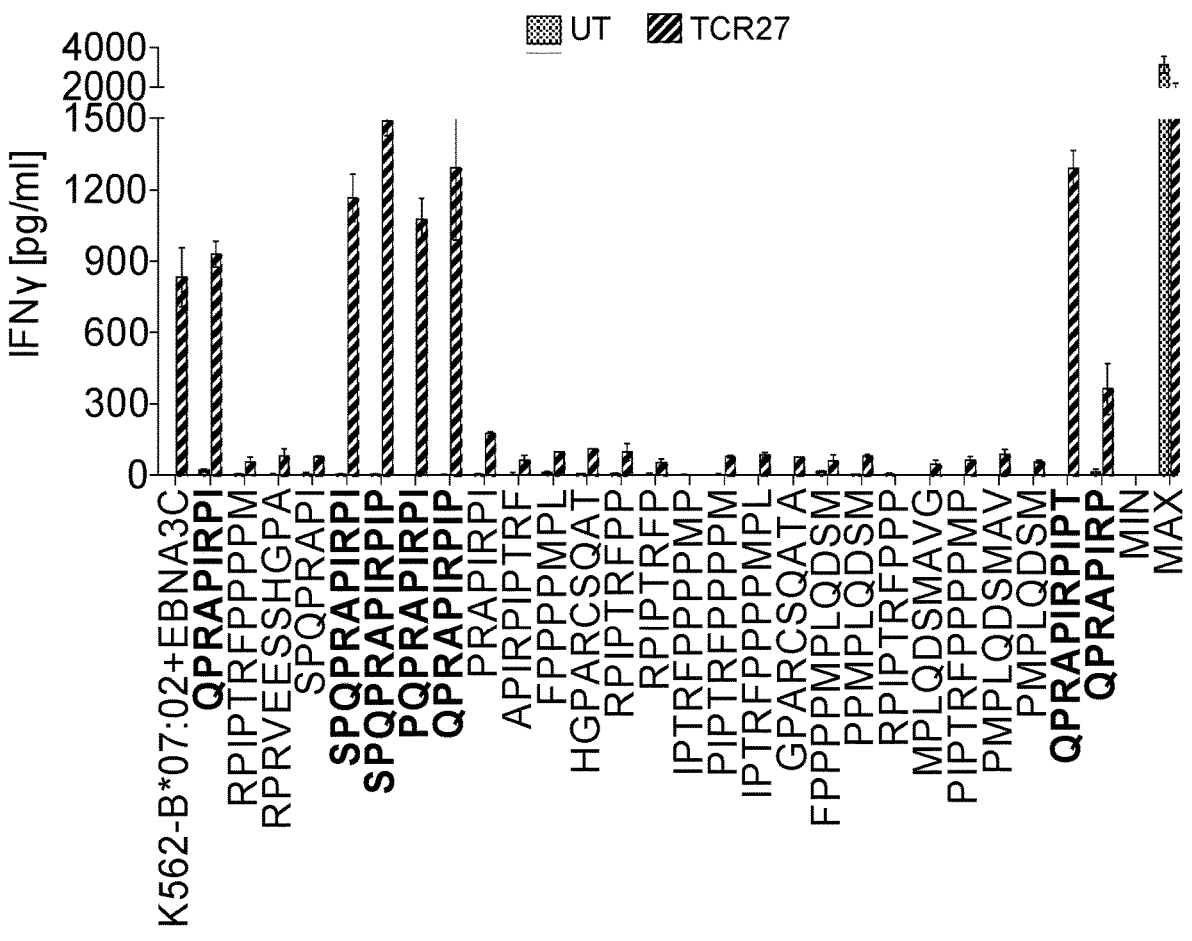
F
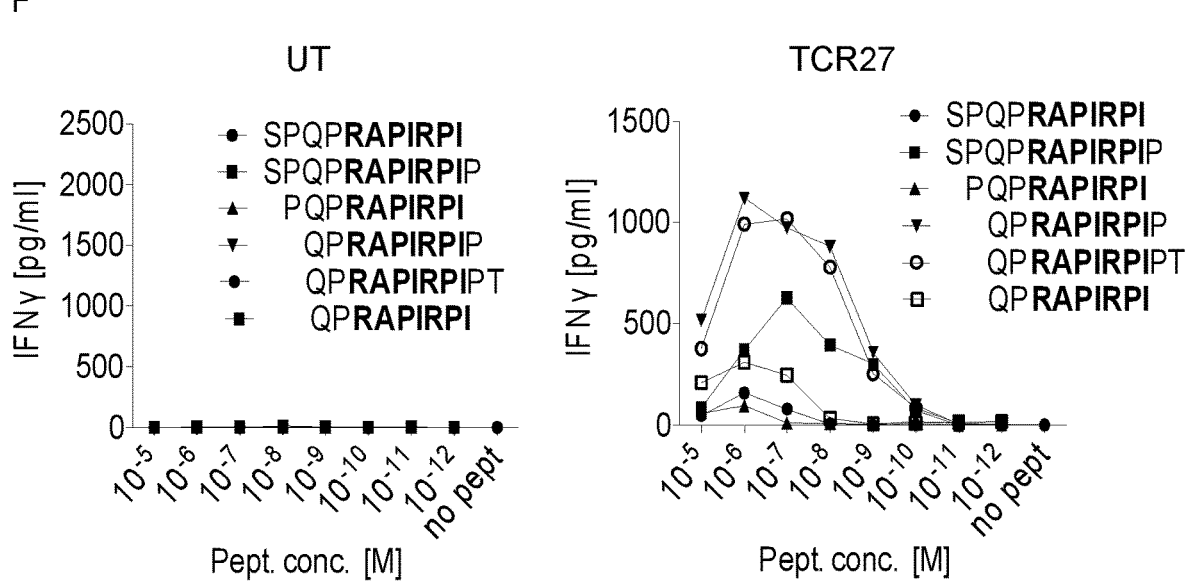

Fig. 11: TCR58 (EBNA3C)
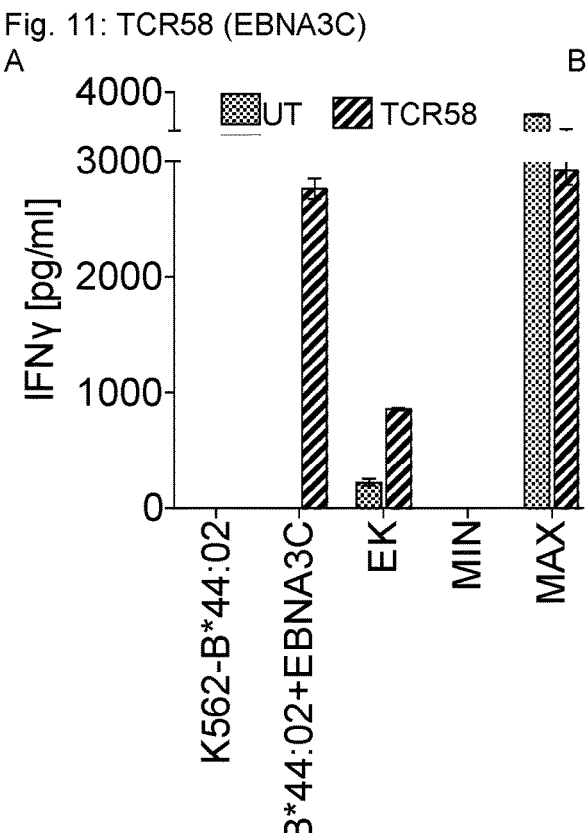
| Truncated construct of EBNA3C | Length (nt) |
|---|---|
| EBNA3C (full length) | 1-2979 |
| EBNA3C/3 | 1-2070 |
| EBNA3C/2 | 1-1569 |
| EBNA3C/1 | 1-567 |
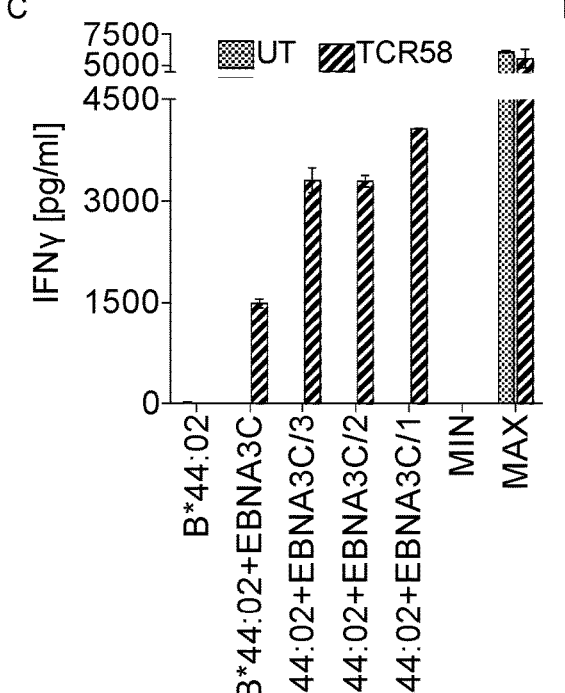
| Epitope | Length (-mer) | Affinity (nM) | Bind level |
|---|---|---|---|
| AEGGVGWRHW | 10 | 12.74 | SB |
| SERLVPEESY | 10 | 415.83 | WB |
| WLLTSPSQSW | 10 | 3285.78 | WB |
| LLTSPSQSW | 9 | 12269.12 | |

Fig. 11: TCR58 (EBNA3C)
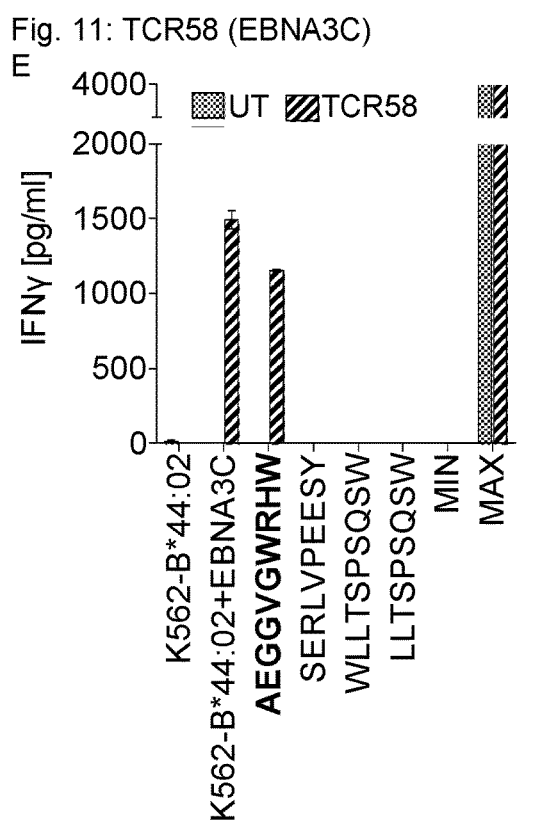
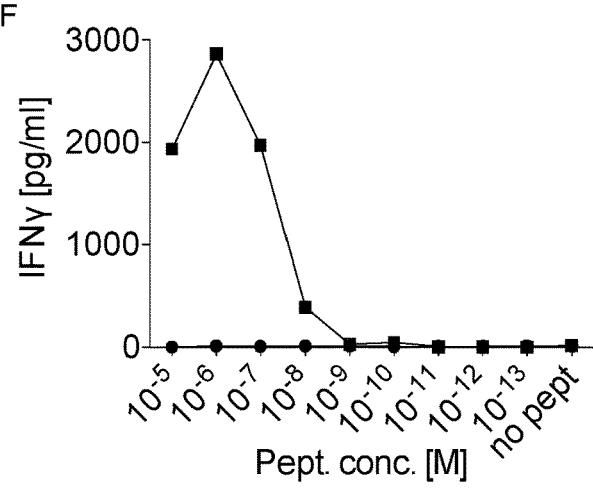
Fig. 12: TCR64 (EBNA3C)
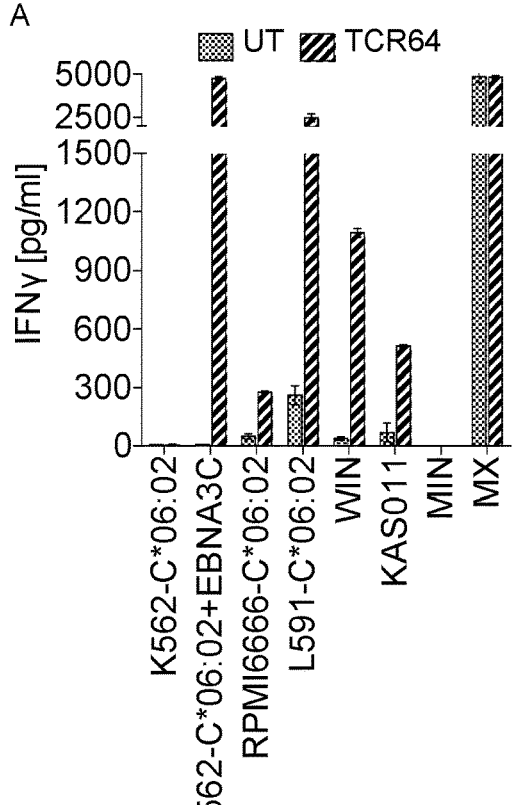
| Truncated construct of EBNA3C | Length (nt) |
|---|---|
| EBNA3C (full length) | 1-2979 |
| EBNA3C/3 | 1-2070 |
| EBNA3C/2 | 1-1569 |
| EBNA3C/1 | 1-567 |

Fig. 12: TCR64 (EBNA3C)

C

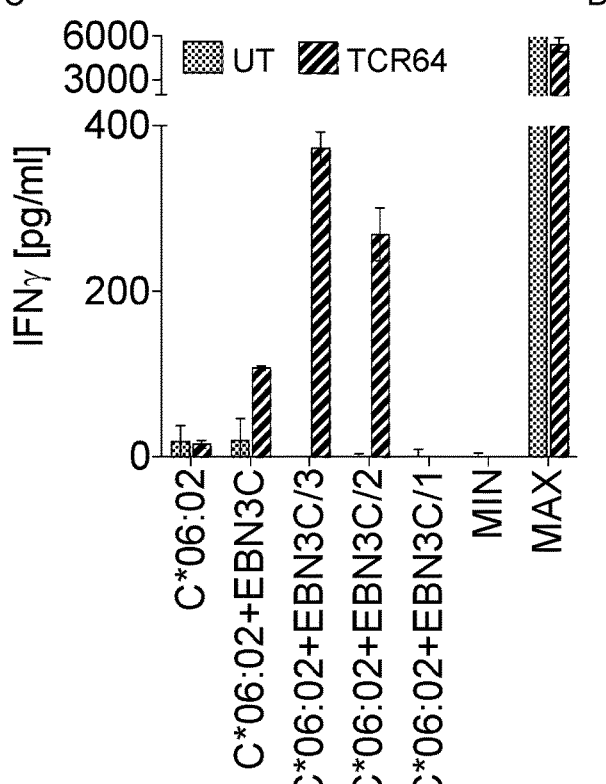

D

| Epitope | Length (-mer) | Affinity (nM) | Bind level |
|---|---|---|---|
| RRYRRIYDL | 9 | 42.19 | SB |
| FRKAQIQGL | 9 | 70.21 | SB |
| AREAEVRFL | 9 | 150.90 | SB |
| LRGKWQRRY | 9 | 154.87 | SB |
| ERYAREAEV | 9 | 194.73 | SB |
| SRRRRGACV | 9 | 561.86 | SB |
| NLLDFVRFM | 9 | 644.16 | SB |
| RRIYDLIEL | 9 | 695.45 | SB |
| RRRRGACVV | 9 | 828.70 | SB |
| VRFLRGKWQ | 9 | 966.12 | SB |
| RRRGACVVY | 9 | 1220.16 | WB |
| QRRYRRIYD | 9 | 1447.20 | WB |
| VRFMGVMSS | 9 | 1479.77 | WB |
| YAREAEVRFL | 10 | 1602.13 | WB |
| NRVGADSIM | 9 | 1849.33 | WB |
| LHHIWQNLL | 9 | 1893.43 | WB |
| RRGIKEHVI | 9 | 2063.06 | WB |
| YRRIYDLIE | 9 | 2320.12 | WB |
| RRYRRIYDLI | 10 | 2493.23 | WB |
| ARRGIKEHV | 9 | 2832.43 | WB |
| QRRYRRIYDL | 10 | 2849.15 | WB |
| WQRRYRRIY | 9 | 3037.39 | WB |
| FLRGKWQRRY | 10 | 3388.28 | WB |
| RRGACVVYD | 9 | 3495.79 | WB |
| VYDDDVIEV | 9 | 4973.38 | WB |
| YAREAEVRF | 9 | 5274.33 | WB |
| GCQNAARTL | 9 | 5591.13 | WB |

Fig. 12: TCR64 (EBNA3C)
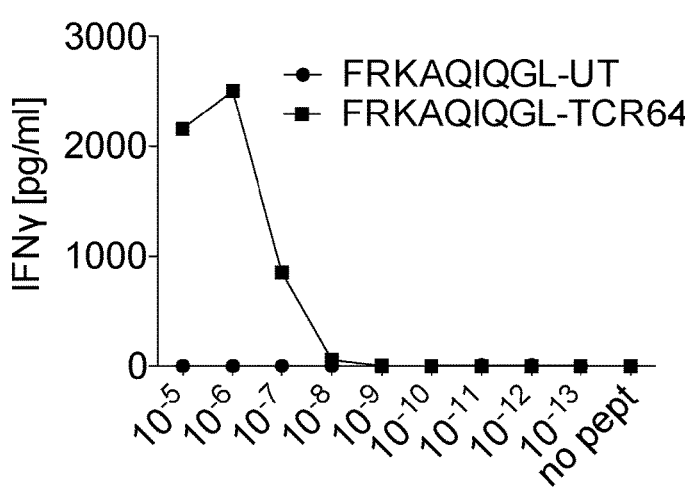

Fig. 13: TCR83 (LMP1)
A
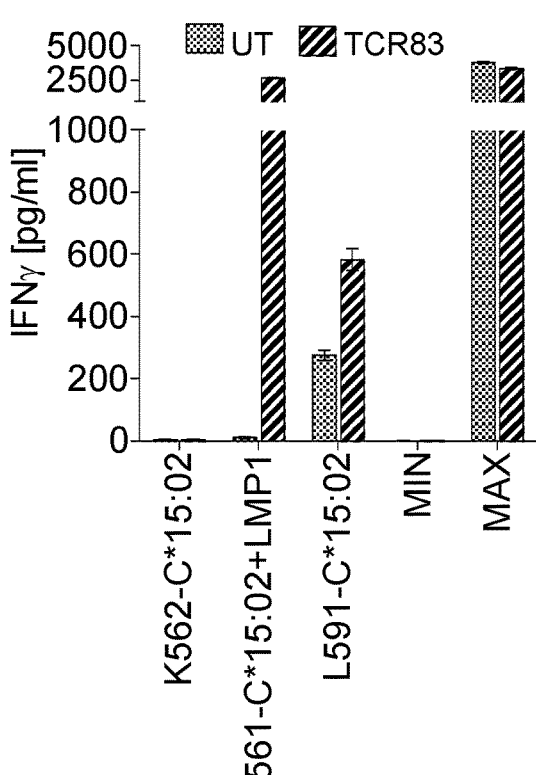
B
| Truncated construct of LMP1 | Length (nt) |
|---|---|
| LMP1 (full length) | 1-1036 |
| LMP1/2 | 1-624 |
| LMP1/1 | 1-315 |
C
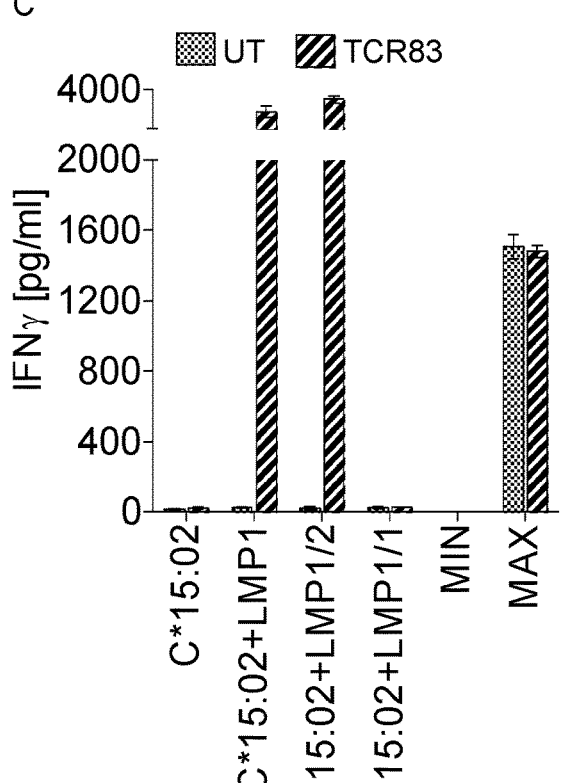
D
| Epitope | Length (-mer) | Affinity (nM) | Bind level |
|---|---|---|---|
| NSNEGRHHL | 9 | 881.86 | WB |
| QQNWWTLLV | 9 | 974.07 | WB |
| DSLPHPQQA | 9 | 3769.65 | WB |
| YLQQNWWTL | 9 | 25471.80 | |

Fig. 13: TCR83 (LMP1)
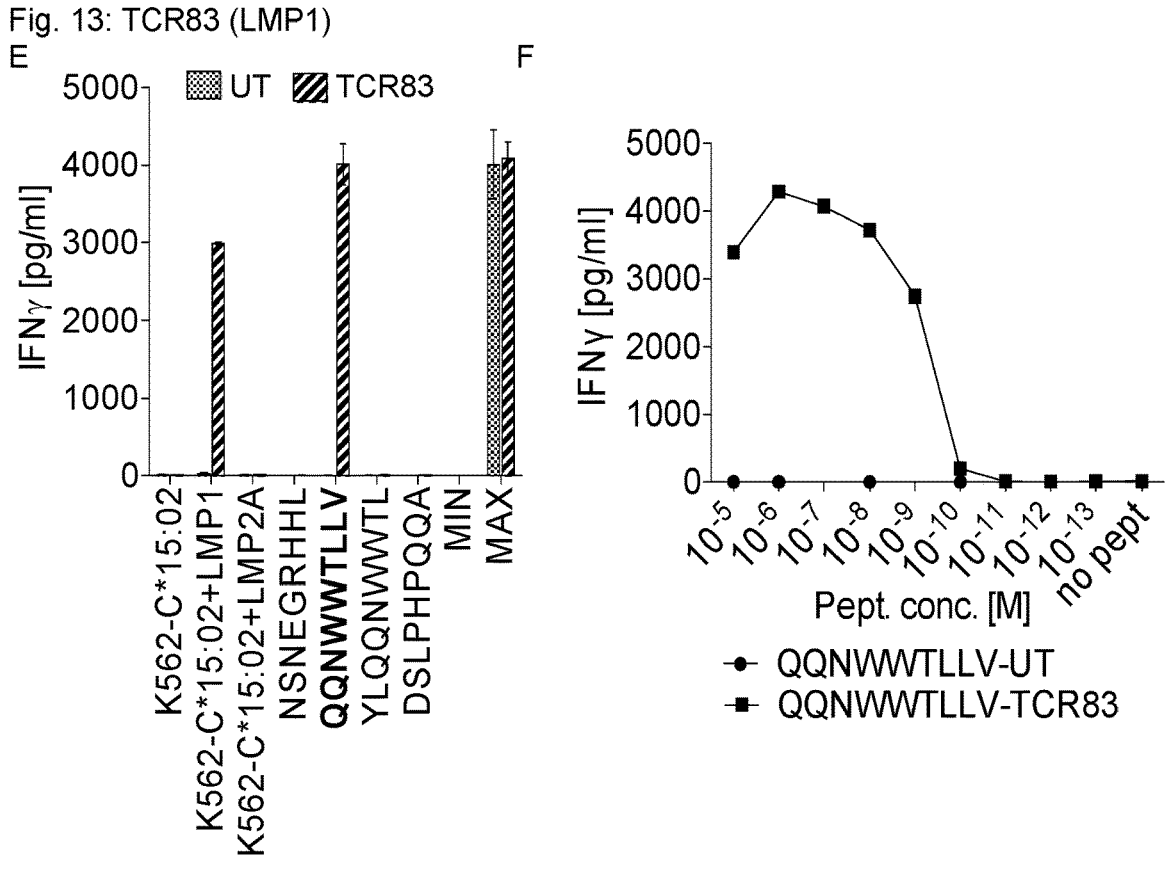
Fig. 14: TCR06 (LMP2A)
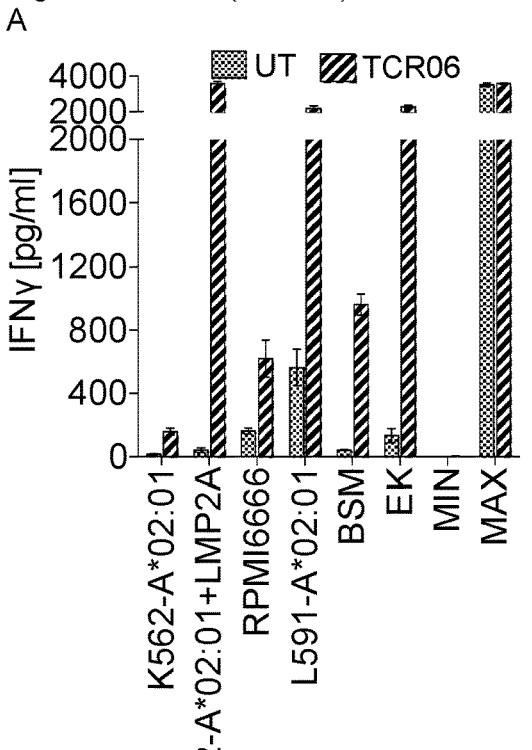
| Truncated construct of LMP2A | Length (nt) |
|---|---|
| LMP2A (full length) | 1-1494 |
| LMP2A/2 | 1-1005 |
| LMP2A/1 | 1-504 |

Fig. 14: TCR06 (LMP2A)
C
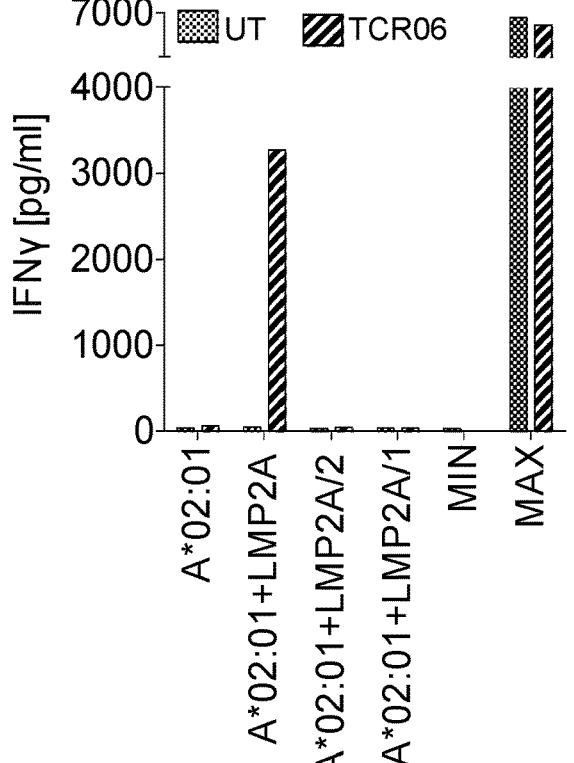
D
| Epitope | Length (-mer) | Affinity (nM) | Bind level |
|---|---|---|---|
| FMCLGGLLTM | 10 | 13.92 | SB |
| MLLLIVAGI | 9 | 23.94 | SB |
| NLFCMLLLI | 9 | 28.54 | SB |
| LLIVAGILFI | 10 | 30.70 | SB |
| NLFCMLLLIV | 10 | 35.77 | SB |
| MCLGGLLTMV | 10 | 37.39 | SB |
| CLGGLLTMV | 9 | 75.60 | WB |
| LIVAGILFI | 9 | 78.80 | WB |
| FIPNLFCML | 9 | 88.29 | WB |
| IVAGILFIL | 9 | 94.09 | WB |
| MLLLIVAGIL | 10 | 102.10 | WB |
| CMLLLIVAGI | 10 | 107.92 | WB |
| PNLFCMLLLI | 10 | 151.79 | WB |
| FIPNLFCMLL | 10 | 154.14 | WB |
E
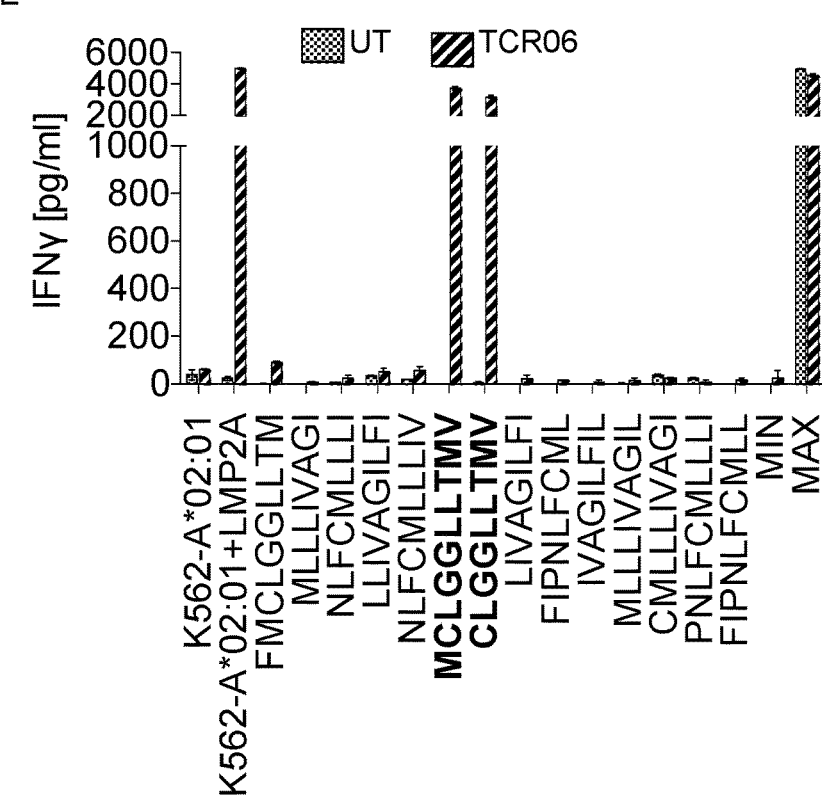

Fig. 14: TCR06 (LMP2A)
F
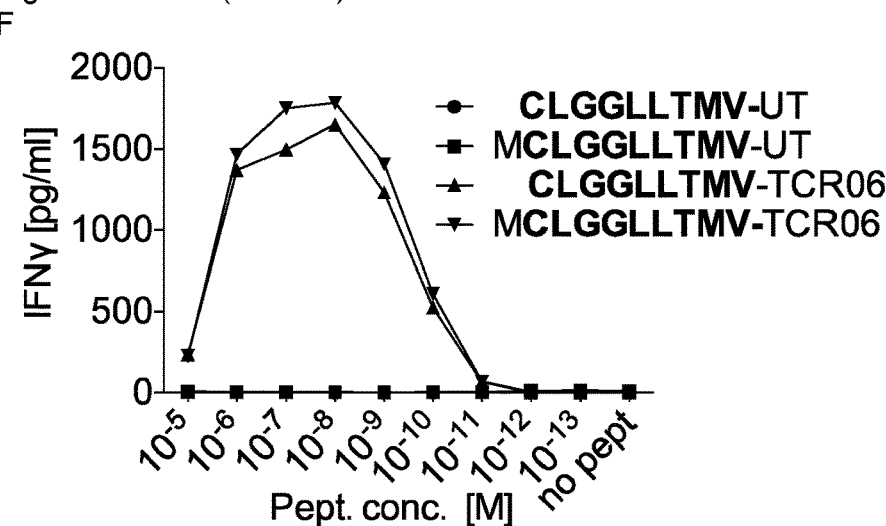
Fig. 15
A
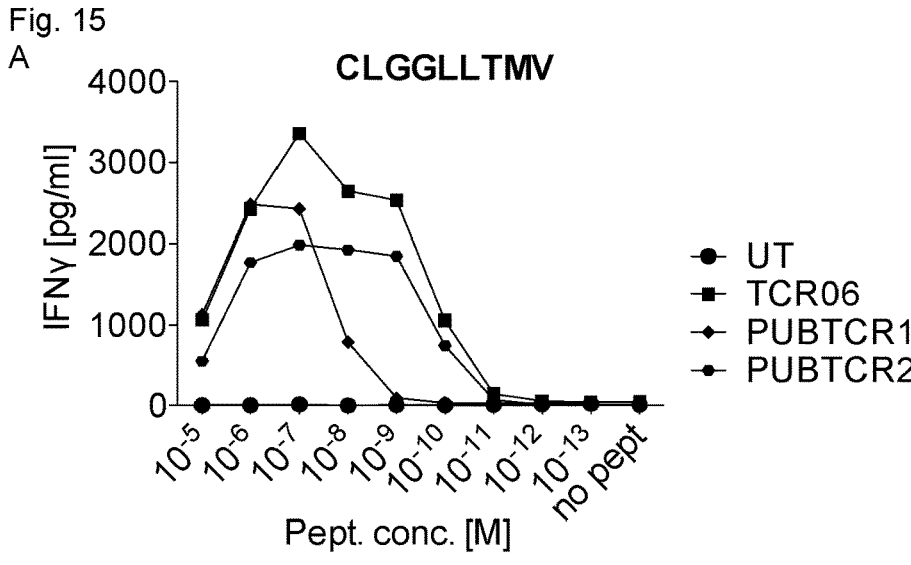
B
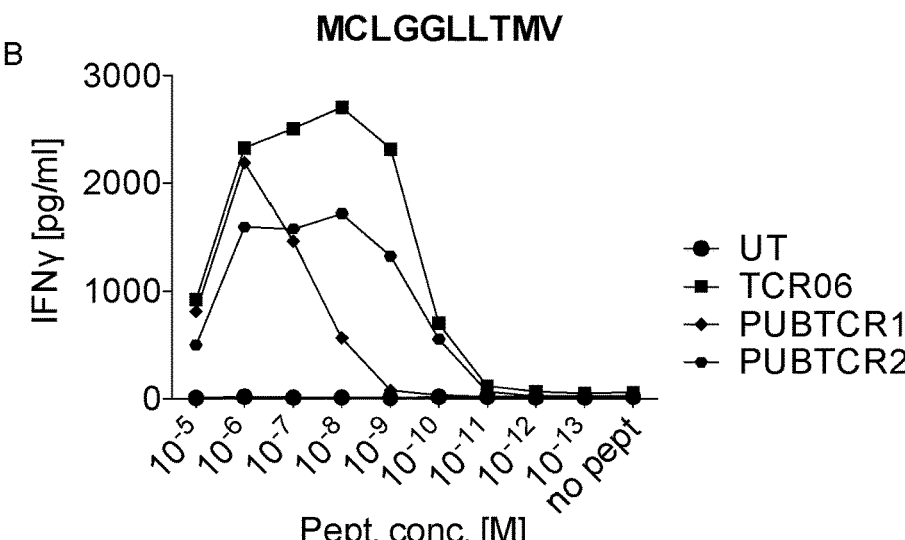

A

B

C

|  | EC50 in $10^{-9}$ M (n=6) | SEM |
|---|---|---|
| TCR06 | 0.34 | 0.07 |
| PUBTCR1 | 1.39 | 0.72 |
| PUBTCR2 | 31.3 | 3.9 |
| TCR-JC | 39.5 | 6.7 |

Fig. 17
A                              B                              C
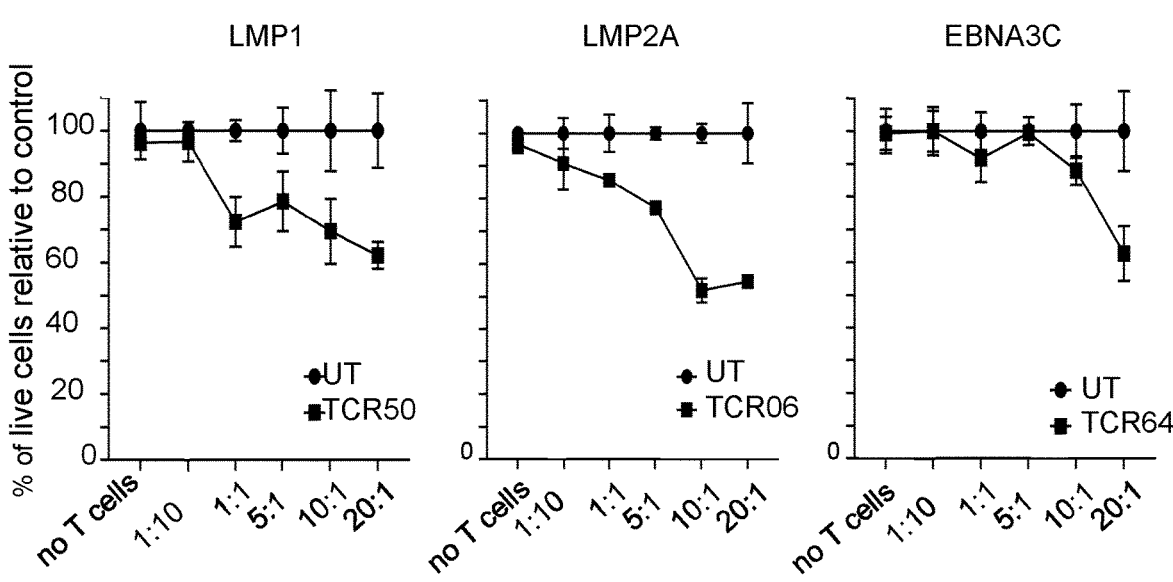
E:T ratio
Fig. 18 A                              B
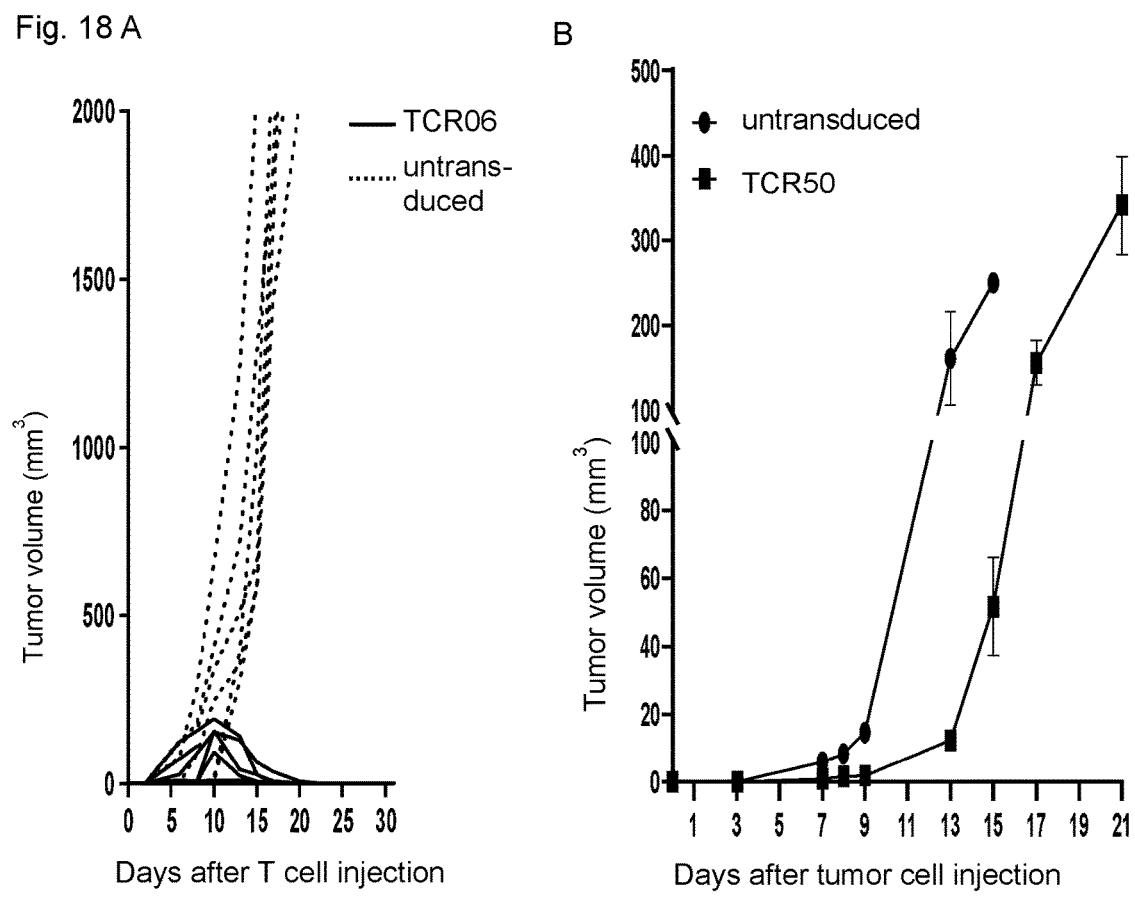
Days after T cell injection          Days after tumor cell injection

SEQUENCE LISTING

```
<160> NUMBER OF SEQ ID NOS: 199

<210> SEQ ID NO 1
<211> LENGTH: 9
<212> TYPE: PRT
<213> ORGANISM: Homo sapiens
<220> FEATURE:
<223> OTHER INFORMATION: Epitope from LMP2A presented on A*02:01

<400> SEQUENCE: 1

Cys Leu Gly Gly Leu Leu Thr Met Val
1               5

<210> SEQ ID NO 2
<211> LENGTH: 9
<212> TYPE: PRT
<213> ORGANISM: Homo sapiens
<220> FEATURE:
<223> OTHER INFORMATION: Epitope from LMP1 presented on B*57:01

<400> SEQUENCE: 2

Ile Ala Leu Tyr Leu Gln Gln Asn Trp
1               5

<210> SEQ ID NO 3
<211> LENGTH: 9
<212> TYPE: PRT
<213> ORGANISM: Homo sapiens
<220> FEATURE:
<223> OTHER INFORMATION: Epitope from LMP1 presented on C*15:02

<400> SEQUENCE: 3

Gln Gln Asn Trp Trp Thr Leu Leu Val
1               5

<210> SEQ ID NO 4
<211> LENGTH: 9
<212> TYPE: PRT
<213> ORGANISM: Homo sapiens
<220> FEATURE:
<223> OTHER INFORMATION: Epitope from EBNA3C presented on C*06:02

<400> SEQUENCE: 4

Phe Arg Lys Ala Gln Ile Gln Gly Leu
1               5

<210> SEQ ID NO 5
<211> LENGTH: 10
<212> TYPE: PRT
<213> ORGANISM: Homo sapiens
<220> FEATURE:
<223> OTHER INFORMATION: Epitope from EBNA3C presented on B*44:02
```

```
<400> SEQUENCE: 5

Ala Glu Gly Gly Val Gly Trp Arg His Trp
1               5                   10

<210> SEQ ID NO 6
<211> LENGTH: 10
<212> TYPE: PRT
<213> ORGANISM: Homo sapiens
<220> FEATURE:
<223> OTHER INFORMATION: Epitope from EBNA3C presented on B*07:02

<400> SEQUENCE: 6

Gln Pro Arg Ala Pro Ile Arg Pro Ile Pro
1               5                   10

<210> SEQ ID NO 7
<211> LENGTH: 11
<212> TYPE: PRT
<213> ORGANISM: Homo sapiens
<220> FEATURE:
<223> OTHER INFORMATION: Epitope from EBNA3C presented on B*07:02

<400> SEQUENCE: 7

Gln Pro Arg Ala Pro Ile Arg Pro Ile Pro Thr
1               5                   10

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 6
<212> TYPE: PRT
<213> ORGANISM: Homo sapiens
<220> FEATURE:
<223> OTHER INFORMATION: TCR06 - TRA - CDR1

<400> SEQUENCE: 11

Asp Ser Ala Ile Tyr Asn
1               5

<210> SEQ ID NO 12
<211> LENGTH: 7
<212> TYPE: PRT
<213> ORGANISM: Homo sapiens
<220> FEATURE:
<223> OTHER INFORMATION: TCR06 - TRA - CDR2

<400> SEQUENCE: 12

Ile Gln Ser Ser Gln Arg Glu
1               5
```

```
<210> SEQ ID NO 13
<211> LENGTH: 11
<212> TYPE: PRT
<213> ORGANISM: Homo sapiens
<220> FEATURE:
<223> OTHER INFORMATION: TCR06 - TRA- CDR3

<400> SEQUENCE: 13

Ala Val Leu Met Asp Ser Asn Tyr Gln Leu Ile
1               5                   10

<210> SEQ ID NO 14
<211> LENGTH: 13
<212> TYPE: PRT
<213> ORGANISM: Homo sapiens
<220> FEATURE:
<223> OTHER INFORMATION: TCR06 - TRA- junction aa

<400> SEQUENCE: 14

Cys Ala Val Leu Met Asp Ser Asn Tyr Gln Leu Ile Trp
1               5                   10

<210> SEQ ID NO 15
<211> LENGTH: 113
<212> TYPE: PRT
<213> ORGANISM: Homo sapiens
<220> FEATURE:
<223> OTHER INFORMATION: TCR06 - TRA - variable region

<400> SEQUENCE: 15

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Leu Met Asp Ser
                85                  90                  95

Asn Tyr Gln Leu Ile Trp Gly Ala Gly Thr Lys Leu Ile Ile Lys Pro
            100                 105                 110

Asp

<210> SEQ ID NO 16
<211> LENGTH: 5
<212> TYPE: PRT
<213> ORGANISM: Homo sapiens
<220> FEATURE:
<223> OTHER INFORMATION: TCR06 - TRB - CDR1

<400> SEQUENCE: 16

Trp Ser His Ser Tyr
1               5

<210> SEQ ID NO 17
<211> LENGTH: 6
<212> TYPE: PRT
<213> ORGANISM: Homo sapiens
<220> FEATURE:
<223> OTHER INFORMATION: TCR06 - TRB - CDR2
```

-continued

```
<400> SEQUENCE: 17

Ser Ala Ala Ala Asp Ile
1               5

<210> SEQ ID NO 18
<211> LENGTH: 12
<212> TYPE: PRT
<213> ORGANISM: Homo sapiens
<220> FEATURE:
<223> OTHER INFORMATION: TCR06 - TRB - CDR3

<400> SEQUENCE: 18

Ala Ser Ser Glu Asp Gly Met Asn Thr Glu Ala Phe
1               5                   10

<210> SEQ ID NO 19
<211> LENGTH: 14
<212> TYPE: PRT
<213> ORGANISM: Homo sapiens
<220> FEATURE:
<223> OTHER INFORMATION: TCR06 - TRB - junction aa

<400> SEQUENCE: 19

Cys Ala Ser Ser Glu Asp Gly Met Asn Thr Glu Ala Phe Phe
1               5                   10

<210> SEQ ID NO 20
<211> LENGTH: 113
<212> TYPE: PRT
<213> ORGANISM: Homo sapiens
<220> FEATURE:
<223> OTHER INFORMATION: TCR06 - TRB - variable region

<400> SEQUENCE: 20

Asp Ala Gly Ile Thr Gln Ser Pro Arg Tyr Lys Ile Thr Glu Thr Gly
1               5                   10                  15

Arg Gln Val Thr Leu Met Cys His Gln Thr Trp Ser His Ser Tyr Met
                20                  25                  30

Phe Trp Tyr Arg Gln Asp Leu Gly His Gly Leu Arg Leu Ile Tyr Tyr
            35                  40                  45

Ser Ala Ala Ala Asp Ile Thr Asp Lys Gly Glu Val Pro Asp Gly Tyr
        50                  55                  60

Val Val Ser Arg Ser Lys Thr Glu Asn Phe Pro Leu Thr Leu Glu Ser
65                  70                  75                  80

Ala Thr Arg Ser Gln Thr Ser Val Tyr Phe Cys Ala Ser Ser Glu Asp
                85                  90                  95

Gly Met Asn Thr Glu Ala Phe Phe Gly Gln Gly Thr Arg Leu Thr Val
                100                 105                 110

Val

<210> SEQ ID NO 21
<211> LENGTH: 6
<212> TYPE: PRT
<213> ORGANISM: Homo sapiens
<220> FEATURE:
<223> OTHER INFORMATION: TCR50 - TRA - CDR1

<400> SEQUENCE: 21

Ser Ser Tyr Ser Pro Ser
1               5

<210> SEQ ID NO 22
```

-continued

```
<211> LENGTH: 8
<212> TYPE: PRT
<213> ORGANISM: Homo sapiens
<220> FEATURE:
<223> OTHER INFORMATION: TCR50 - TRA - CDR2

<400> SEQUENCE: 22

Tyr Thr Ser Ala Ala Thr Leu Val
1               5

<210> SEQ ID NO 23
<211> LENGTH: 11
<212> TYPE: PRT
<213> ORGANISM: Homo sapiens
<220> FEATURE:
<223> OTHER INFORMATION: TCR50 - TRA - CDR3

<400> SEQUENCE: 23

Val Val Met Ala Thr Gly Phe Gln Lys Leu Val
1               5               10

<210> SEQ ID NO 24
<211> LENGTH: 13
<212> TYPE: PRT
<213> ORGANISM: Homo sapiens
<220> FEATURE:
<223> OTHER INFORMATION: TCR50 - TRA - junction aa

<400> SEQUENCE: 24

Cys Val Val Met Ala Thr Gly Phe Gln Lys Leu Val Phe
1               5               10

<210> SEQ ID NO 25
<211> LENGTH: 114
<212> TYPE: PRT
<213> ORGANISM: Homo sapiens
<220> FEATURE:
<223> OTHER INFORMATION: TCR50 - TRA - variable region

<400> SEQUENCE: 25

Ala Gln Ser Val Thr Gln Leu Asp Ser His Val Ser Val Ser Glu Gly
1               5               10               15

Thr Pro Val Leu Leu Arg Cys Asn Tyr Ser Ser Ser Tyr Ser Pro Ser
                20              25              30

Leu Phe Trp Tyr Val Gln His Pro Asn Lys Gly Leu Gln Leu Leu Leu
            35              40              45

Lys Tyr Thr Ser Ala Ala Thr Leu Val Lys Gly Ile Asn Gly Phe Glu
    50              55              60

Ala Glu Phe Lys Lys Ser Glu Thr Ser Phe His Leu Thr Lys Pro Ser
65              70              75              80

Ala His Met Ser Asp Ala Ala Glu Tyr Phe Cys Val Val Met Ala Thr
                85              90              95

Gly Phe Gln Lys Leu Val Phe Gly Thr Gly Thr Arg Leu Leu Val Ser
            100             105             110

Pro Asn

<210> SEQ ID NO 26
<211> LENGTH: 5
<212> TYPE: PRT
<213> ORGANISM: Homo sapiens
<220> FEATURE:
<223> OTHER INFORMATION: TCR50 - TRB - CDR1

<400> SEQUENCE: 26
```

```
Ser Gly Asp Leu Ser
1               5

<210> SEQ ID NO 27
<211> LENGTH: 6
<212> TYPE: PRT
<213> ORGANISM: Homo sapiens
<220> FEATURE:
<223> OTHER INFORMATION: TCR50 - TRB - CDR2

<400> SEQUENCE: 27

Tyr Tyr Asn Gly Glu Glu
1               5

<210> SEQ ID NO 28
<211> LENGTH: 12
<212> TYPE: PRT
<213> ORGANISM: Homo sapiens
<220> FEATURE:
<223> OTHER INFORMATION: TCR50 - TRB - CDR3

<400> SEQUENCE: 28

Ala Ser Ser Val Thr Ser Gly Ser Asp Glu Gln Phe
1               5                   10

<210> SEQ ID NO 29
<211> LENGTH: 14
<212> TYPE: PRT
<213> ORGANISM: Homo sapiens
<220> FEATURE:
<223> OTHER INFORMATION: TCR50 - TRB - junction aa

<400> SEQUENCE: 29

Cys Ala Ser Ser Val Thr Ser Gly Ser Asp Glu Gln Phe Phe
1               5                   10

<210> SEQ ID NO 30
<211> LENGTH: 113
<212> TYPE: PRT
<213> ORGANISM: Homo sapiens
<220> FEATURE:
<223> OTHER INFORMATION: TCR50 - TRB - variable region

<400> SEQUENCE: 30

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
                20                  25                  30

Tyr Trp Tyr Gln Gln Ser Leu Asp Gln Gly Leu Gln Phe Leu Ile Gln
            35                  40                  45

Tyr Tyr Asn Gly Glu Glu Arg Ala Lys Gly Asn Ile Leu Glu Arg Phe
        50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Val Thr
                85                  90                  95

Ser Gly Ser Asp Glu Gln Phe Phe Gly Pro Gly Thr Arg Leu Thr Val
            100                 105                 110

Leu

<210> SEQ ID NO 31
<211> LENGTH: 6
```

```
<212> TYPE: PRT
<213> ORGANISM: Homo sapiens
<220> FEATURE:
<223> OTHER INFORMATION: TCR83 - TRA - CDR1

<400> SEQUENCE: 31

Thr Ser Gly Phe Asn Gly
1               5

<210> SEQ ID NO 32
<211> LENGTH: 6
<212> TYPE: PRT
<213> ORGANISM: Homo sapiens
<220> FEATURE:
<223> OTHER INFORMATION: TCR83 - TRA - CDR2

<400> SEQUENCE: 32

Asn Val Leu Asp Gly Leu
1               5

<210> SEQ ID NO 33
<211> LENGTH: 11
<212> TYPE: PRT
<213> ORGANISM: Homo sapiens
<220> FEATURE:
<223> OTHER INFORMATION: TCR83 - TRA - CDR3

<400> SEQUENCE: 33

Ala Ala Val Asn Asn Ala Gly Asn Met Leu Thr
1               5                   10

<210> SEQ ID NO 34
<211> LENGTH: 13
<212> TYPE: PRT
<213> ORGANISM: Homo sapiens
<220> FEATURE:
<223> OTHER INFORMATION: TCR83 - TRA - junction aa

<400> SEQUENCE: 34

Cys Ala Ala Val Asn Asn Ala Gly Asn Met Leu Thr Phe
1               5                   10

<210> SEQ ID NO 35
<211> LENGTH: 111
<212> TYPE: PRT
<213> ORGANISM: Homo sapiens
<220> FEATURE:
<223> OTHER INFORMATION: TCR83 - TRA - variable region

<400> SEQUENCE: 35

Gly Gln Asn Ile Asp Gln Pro Thr Glu Met Thr Ala Thr Glu Gly Ala
1               5                   10                  15

Ile Val Gln Ile Asn Cys Thr Tyr Gln Thr Ser Gly Phe Asn Gly Leu
            20                  25                  30

Phe Trp Tyr Gln Gln His Ala Gly Glu Ala Pro Thr Phe Leu Ser Tyr
        35                  40                  45

Asn Val Leu Asp Gly Leu Glu Glu Lys Gly Arg Phe Ser Ser Phe Leu
    50                  55                  60

Ser Arg Ser Lys Gly Tyr Ser Tyr Leu Leu Leu Lys Glu Leu Gln Met
65                  70                  75                  80

Lys Asp Ser Ala Ser Tyr Leu Cys Ala Ala Val Asn Asn Ala Gly Asn
                85                  90                  95

Met Leu Thr Phe Gly Gly Gly Thr Arg Leu Met Val Lys Pro His
            100                 105                 110
```

<210> SEQ ID NO 36
<211> LENGTH: 5
<212> TYPE: PRT
<213> ORGANISM: Homo sapiens
<220> FEATURE:
<223> OTHER INFORMATION: TCR83 - TRB - CDR1

<400> SEQUENCE: 36

Leu Gly His Asp Thr
1               5

<210> SEQ ID NO 37
<211> LENGTH: 6
<212> TYPE: PRT
<213> ORGANISM: Homo sapiens
<220> FEATURE:
<223> OTHER INFORMATION: TCR83 - TRB - CDR2

<400> SEQUENCE: 37

Tyr Asn Asn Lys Glu Leu
1               5

<210> SEQ ID NO 38
<211> LENGTH: 15
<212> TYPE: PRT
<213> ORGANISM: Homo sapiens
<220> FEATURE:
<223> OTHER INFORMATION: TCR83 - TRB - CDR3

<400> SEQUENCE: 38

Ala Ser Ser Gln Gly Tyr Gly Gly Pro Ser Thr Asp Thr Gln Tyr
1               5                   10                  15

<210> SEQ ID NO 39
<211> LENGTH: 17
<212> TYPE: PRT
<213> ORGANISM: Homo sapiens
<220> FEATURE:
<223> OTHER INFORMATION: TCR83 - TRB - junction aa

<400> SEQUENCE: 39

Cys Ala Ser Ser Gln Gly Tyr Gly Gly Pro Ser Thr Asp Thr Gln Tyr
1               5                   10                  15

Phe

<210> SEQ ID NO 40
<211> LENGTH: 116
<212> TYPE: PRT
<213> ORGANISM: Homo sapiens
<220> FEATURE:
<223> OTHER INFORMATION: TCR83 - TRB - variable region

<400> SEQUENCE: 40

Asp Thr Ala Val Ser Gln Thr Pro Lys Tyr Leu Val Thr Gln Met Gly
1               5                   10                  15

Asn Asp Lys Ser Ile Lys Cys Glu Gln Asn Leu Gly His Asp Thr Met
            20                  25                  30

Tyr Trp Tyr Lys Gln Asp Ser Lys Lys Phe Leu Lys Ile Met Phe Ser
        35                  40                  45

Tyr Asn Asn Lys Glu Leu Ile Ile Asn Glu Thr Val Pro Asn Arg Phe
    50                  55                  60

Ser Pro Lys Ser Pro Asp Lys Ala His Leu Asn Leu His Ile Asn Ser
65                  70                  75                  80

```
Leu Glu Leu Gly Asp Ser Ala Val Tyr Phe Cys Ala Ser Ser Gln Gly
                85                  90                  95

Tyr Gly Gly Pro Ser Thr Asp Thr Gln Tyr Phe Gly Pro Gly Thr Arg
            100                 105                 110

Leu Thr Val Leu
        115

<210> SEQ ID NO 41
<211> LENGTH: 5
<212> TYPE: PRT
<213> ORGANISM: Homo sapiens
<220> FEATURE:
<223> OTHER INFORMATION: TCR64 - TRA - CDR1

<400> SEQUENCE: 41

Ser Val Phe Ser Ser
1               5

<210> SEQ ID NO 42
<211> LENGTH: 7
<212> TYPE: PRT
<213> ORGANISM: Homo sapiens
<220> FEATURE:
<223> OTHER INFORMATION: TCR64 - TRA - CDR2

<400> SEQUENCE: 42

Val Val Thr Gly Gly Glu Val
1               5

<210> SEQ ID NO 43
<211> LENGTH: 13
<212> TYPE: PRT
<213> ORGANISM: Homo sapiens
<220> FEATURE:
<223> OTHER INFORMATION: TCR64 - TRA - CDR3

<400> SEQUENCE: 43

Ala Gly Asp Val Asp Thr Gly Thr Ala Ser Lys Leu Thr
1               5                   10

<210> SEQ ID NO 44
<211> LENGTH: 15
<212> TYPE: PRT
<213> ORGANISM: Homo sapiens
<220> FEATURE:
<223> OTHER INFORMATION: TCR64 - TRA - junction aa

<400> SEQUENCE: 44

Cys Ala Gly Asp Val Asp Thr Gly Thr Ala Ser Lys Leu Thr Phe
1               5                   10                  15

<210> SEQ ID NO 45
<211> LENGTH: 114
<212> TYPE: PRT
<213> ORGANISM: Homo sapiens
<220> FEATURE:
<223> OTHER INFORMATION: TCR64 - TRA - variable region

<400> SEQUENCE: 45

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
```

-continued

```
              35               40               45
Val Val Thr Gly Gly Glu Val Lys Lys Leu Lys Arg Leu Thr Phe Gln
    50               55               60

Phe Gly Asp Ala Arg Lys Asp Ser Ser Leu His Ile Thr Ala Ala Gln
65               70               75               80

Pro Gly Asp Thr Gly Leu Tyr Leu Cys Ala Gly Asp Val Asp Thr Gly
              85               90               95

Thr Ala Ser Lys Leu Thr Phe Gly Thr Gly Thr Arg Leu Gln Val Thr
          100              105              110

Leu Asp

<210> SEQ ID NO 46
<211> LENGTH: 5
<212> TYPE: PRT
<213> ORGANISM: Homo sapiens
<220> FEATURE:
<223> OTHER INFORMATION: TCR64 - TRB - CDR1

<400> SEQUENCE: 46

Met Asp His Glu Asn
1               5

<210> SEQ ID NO 47
<211> LENGTH: 6
<212> TYPE: PRT
<213> ORGANISM: Homo sapiens
<220> FEATURE:
<223> OTHER INFORMATION: TCR64 - TRB - CDR2

<400> SEQUENCE: 47

Ser Tyr Asp Val Lys Met
1               5

<210> SEQ ID NO 48
<211> LENGTH: 14
<212> TYPE: PRT
<213> ORGANISM: Homo sapiens
<220> FEATURE:
<223> OTHER INFORMATION: TCR64 - TRB - CDR3

<400> SEQUENCE: 48

Ala Ser Ser Leu Leu Gly Ser Gly Ala Leu Tyr Glu Gln Tyr
1               5                    10

<210> SEQ ID NO 49
<211> LENGTH: 16
<212> TYPE: PRT
<213> ORGANISM: Homo sapiens
<220> FEATURE:
<223> OTHER INFORMATION: TCR64 - TRB - junction aa

<400> SEQUENCE: 49

Cys Ala Ser Ser Leu Leu Gly Ser Gly Ala Leu Tyr Glu Gln Tyr Phe
1               5                    10               15

<210> SEQ ID NO 50
<211> LENGTH: 115
<212> TYPE: PRT
<213> ORGANISM: Homo sapiens
<220> FEATURE:
<223> OTHER INFORMATION: TCR64 - TRB - variable region

<400> SEQUENCE: 50

Asp Val Lys Val Thr Gln Ser Ser Arg Tyr Leu Val Lys Arg Thr Gly
```

```
1               5              10             15

Glu Lys Val Phe Leu Glu Cys Val Gln Asp Met Asp His Glu Asn Met
             20              25             30

Phe Trp Tyr Arg Gln Asp Pro Gly Leu Gly Leu Arg Leu Ile Tyr Phe
         35              40             45

Ser Tyr Asp Val Lys Met Lys Glu Lys Gly Asp Ile Pro Glu Gly Tyr
     50              55             60

Ser Val Ser Arg Glu Lys Lys Glu Arg Phe Ser Leu Ile Leu Glu Ser
65               70             75             80

Ala Ser Thr Asn Gln Thr Ser Met Tyr Leu Cys Ala Ser Ser Leu Leu
             85              90             95

Gly Ser Gly Ala Leu Tyr Glu Gln Tyr Phe Gly Pro Gly Thr Arg Leu
         100             105            110

Thr Val Thr
     115
```

<210> SEQ ID NO 51
<211> LENGTH: 6
<212> TYPE: PRT
<213> ORGANISM: Homo sapiens
<220> FEATURE:
<223> OTHER INFORMATION: CDR25 - TRA - CDR1

<400> SEQUENCE: 51

```
Ser Ser Tyr Ser Pro Ser
1               5
```

<210> SEQ ID NO 52
<211> LENGTH: 8
<212> TYPE: PRT
<213> ORGANISM: Homo sapiens
<220> FEATURE:
<223> OTHER INFORMATION: CDR25 - TRA - CDR2

<400> SEQUENCE: 52

```
Tyr Thr Ser Ala Ala Thr Leu Val
1               5
```

<210> SEQ ID NO 53
<211> LENGTH: 11
<212> TYPE: PRT
<213> ORGANISM: Homo sapiens
<220> FEATURE:
<223> OTHER INFORMATION: CDR25 - TRA - CDR3

<400> SEQUENCE: 53

```
Val Ala Trp Asp Thr Gly Phe Gln Lys Leu Val
1               5              10
```

<210> SEQ ID NO 54
<211> LENGTH: 13
<212> TYPE: PRT
<213> ORGANISM: Homo sapiens
<220> FEATURE:
<223> OTHER INFORMATION: CDR25 - TRA - junction aa

<400> SEQUENCE: 54

```
Cys Val Ala Trp Asp Thr Gly Phe Gln Lys Leu Val Phe
1               5              10
```

<210> SEQ ID NO 55
<211> LENGTH: 114
<212> TYPE: PRT

<213> ORGANISM: Homo sapiens
<220> FEATURE:
<223> OTHER INFORMATION: CD25 - TRA - variable region

<400> SEQUENCE: 55

```
Ala Gln Ser Val Thr Gln Leu Asp Ser His Val Ser Val Ser Glu Gly
1               5                   10                  15

Thr Pro Val Leu Leu Arg Cys Asn Tyr Ser Ser Ser Tyr Ser Pro Ser
            20                  25                  30

Leu Phe Trp Tyr Val Gln His Pro Asn Lys Gly Leu Gln Leu Leu Leu
        35                  40                  45

Lys Tyr Thr Ser Ala Ala Thr Leu Val Lys Gly Ile Asn Gly Phe Glu
    50                  55                  60

Ala Glu Phe Lys Lys Ser Glu Thr Ser Phe His Leu Thr Lys Pro Ser
65                  70                  75                  80

Ala His Met Ser Asp Ala Ala Glu Tyr Phe Cys Val Ala Trp Asp Thr
                85                  90                  95

Gly Phe Gln Lys Leu Val Phe Gly Thr Gly Thr Arg Leu Leu Val Ser
            100                 105                 110

Pro Asn
```

<210> SEQ ID NO 56
<211> LENGTH: 5
<212> TYPE: PRT
<213> ORGANISM: Homo sapiens
<220> FEATURE:
<223> OTHER INFORMATION: CD25 - TRB - CDR1

<400> SEQUENCE: 56

```
Ser Asn His Leu Tyr
1               5
```

<210> SEQ ID NO 57
<211> LENGTH: 6
<212> TYPE: PRT
<213> ORGANISM: Homo sapiens
<220> FEATURE:
<223> OTHER INFORMATION: CD25 - TRB - CDR2

<400> SEQUENCE: 57

```
Phe Tyr Asn Asn Glu Ile
1               5
```

<210> SEQ ID NO 58
<211> LENGTH: 10
<212> TYPE: PRT
<213> ORGANISM: Homo sapiens
<220> FEATURE:
<223> OTHER INFORMATION: CD25 - TRB - CDR3

<400> SEQUENCE: 58

```
Ala Ser Lys Ala Leu Ala Asp Thr Gln Tyr
1               5                   10
```

<210> SEQ ID NO 59
<211> LENGTH: 12
<212> TYPE: PRT
<213> ORGANISM: Homo sapiens
<220> FEATURE:
<223> OTHER INFORMATION: CD25 - TRB - junction aa

<400> SEQUENCE: 59

```
Cys Ala Ser Lys Ala Leu Ala Asp Thr Gln Tyr Phe
```

-continued

```
1               5                    10
```

```
<210> SEQ ID NO 60
<211> LENGTH: 112
<212> TYPE: PRT
<213> ORGANISM: Homo sapiens
<220> FEATURE:
<223> OTHER INFORMATION: TCR25 - TRB - variable region

<400> SEQUENCE: 60

Glu Pro Glu Val Thr Gln Thr Pro Ser His Gln Val Thr Gln Met Gly
1               5                    10                   15

Gln Glu Val Ile Leu Arg Cys Val Pro Ile Ser Asn His Leu Tyr Phe
                20                   25                   30

Tyr Trp Tyr Arg Gln Ile Leu Gly Gln Lys Val Glu Phe Leu Val Ser
          35                   40                   45

Phe Tyr Asn Asn Glu Ile Ser Glu Lys Ser Glu Ile Phe Asp Asp Gln
      50                   55                   60

Phe Ser Val Glu Arg Pro Asp Gly Ser Asn Phe Thr Leu Lys Ile Arg
65                   70                   75                   80

Ser Thr Lys Leu Glu Asp Ser Ala Met Tyr Phe Cys Ala Ser Lys Ala
                85                   90                   95

Leu Ala Asp Thr Gln Tyr Phe Gly Pro Gly Thr Arg Leu Thr Val Leu
              100                   105                  110

<210> SEQ ID NO 61
<211> LENGTH: 6
<212> TYPE: PRT
<213> ORGANISM: Homo sapiens
<220> FEATURE:
<223> OTHER INFORMATION: TCR58 - TRA - CDR1

<400> SEQUENCE: 61

Asn Ser Ala Ser Gln Ser
1               5

<210> SEQ ID NO 62
<211> LENGTH: 6
<212> TYPE: PRT
<213> ORGANISM: Homo sapiens
<220> FEATURE:
<223> OTHER INFORMATION: TCR58 - TRA - CDR2

<400> SEQUENCE: 62

Val Tyr Ser Ser Gly Asn
1               5

<210> SEQ ID NO 63
<211> LENGTH: 11
<212> TYPE: PRT
<213> ORGANISM: Homo sapiens
<220> FEATURE:
<223> OTHER INFORMATION: TCR58 - TRA - CDR3

<400> SEQUENCE: 63

Val Ala Ser Gly Asp Ser Ser Tyr Lys Leu Ile
1               5                    10

<210> SEQ ID NO 64
<211> LENGTH: 13
<212> TYPE: PRT
<213> ORGANISM: Homo sapiens
<220> FEATURE:
<223> OTHER INFORMATION: TCR58 - TRA - junction aa
```

-continued

<400> SEQUENCE: 64

Cys Val Ala Ser Gly Asp Ser Ser Tyr Lys Leu Ile Phe
1               5                   10

<210> SEQ ID NO 65
<211> LENGTH: 111
<212> TYPE: PRT
<213> ORGANISM: Homo sapiens
<220> FEATURE:
<223> OTHER INFORMATION: TCR58 - TRA - variable region

<400> SEQUENCE: 65

Arg Lys Glu Val Glu Gln Asp Pro Gly Pro Phe Asn Val Pro Glu Gly
1               5                   10                  15

Ala Thr Val Ala Phe Asn Cys Thr Tyr Ser Asn Ser Ala Ser Gln Ser
            20                  25                  30

Phe Phe Trp Tyr Arg Gln Asp Cys Arg Lys Glu Pro Lys Leu Leu Met
        35                  40                  45

Ser Val Tyr Ser Ser Gly Asn Glu Asp Gly Arg Phe Thr Ala Gln Leu
    50                  55                  60

Asn Arg Ala Ser Gln Tyr Ile Ser Leu Leu Ile Arg Asp Ser Lys Leu
65                  70                  75                  80

Ser Asp Ser Ala Thr Tyr Leu Cys Val Ala Ser Gly Asp Ser Ser Tyr
                85                  90                  95

Lys Leu Ile Phe Gly Ser Gly Thr Arg Leu Leu Val Arg Pro Asp
                100                 105                 110

<210> SEQ ID NO 66
<211> LENGTH: 5
<212> TYPE: PRT
<213> ORGANISM: Homo sapiens
<220> FEATURE:
<223> OTHER INFORMATION: TCR58 - TRB - CDR1

<400> SEQUENCE: 66

Ser Asn His Leu Tyr
1               5

<210> SEQ ID NO 67
<211> LENGTH: 6
<212> TYPE: PRT
<213> ORGANISM: Homo sapiens
<220> FEATURE:
<223> OTHER INFORMATION: TCR58 - TRB - CDR2

<400> SEQUENCE: 67

Phe Tyr Asn Asn Glu Ile
1               5

<210> SEQ ID NO 68
<211> LENGTH: 13
<212> TYPE: PRT
<213> ORGANISM: Homo sapiens
<220> FEATURE:
<223> OTHER INFORMATION: TCR58 - TRB - CDR3

<400> SEQUENCE: 68

Ala Ser Ser Asp Pro Leu Ser Thr Tyr Asn Glu Gln Phe
1               5                   10

<210> SEQ ID NO 69
<211> LENGTH: 15

<212> TYPE: PRT
<213> ORGANISM: Homo sapiens
<220> FEATURE:
<223> OTHER INFORMATION: TCR58 - TRB - junction aa

<400> SEQUENCE: 69

Cys Ala Ser Ser Asp Pro Leu Ser Thr Tyr Asn Glu Gln Phe Phe
1               5                   10                  15

<210> SEQ ID NO 70
<211> LENGTH: 115
<212> TYPE: PRT
<213> ORGANISM: Homo sapiens
<220> FEATURE:
<223> OTHER INFORMATION: TCR58 - TRB - variable region

<400> SEQUENCE: 70

Glu Pro Glu Val Thr Gln Thr Pro Ser His Gln Val Thr Gln Met Gly
1               5                   10                  15

Gln Glu Val Ile Leu Arg Cys Val Pro Ile Ser Asn His Leu Tyr Phe
                20                  25                  30

Tyr Trp Tyr Arg Gln Ile Leu Gly Gln Lys Val Glu Phe Leu Val Ser
            35                  40                  45

Phe Tyr Asn Asn Glu Ile Ser Glu Lys Ser Glu Ile Phe Asp Asp Gln
        50                  55                  60

Phe Ser Val Glu Arg Pro Asp Gly Ser Asn Phe Thr Leu Lys Ile Arg
65                  70                  75                  80

Ser Thr Lys Leu Glu Asp Ser Ala Met Tyr Phe Cys Ala Ser Ser Asp
                85                  90                  95

Pro Leu Ser Thr Tyr Asn Glu Gln Phe Phe Gly Pro Gly Thr Arg Leu
                100                 105                 110

Thr Val Leu
        115

<210> SEQ ID NO 71
<211> LENGTH: 7
<212> TYPE: PRT
<213> ORGANISM: Homo sapiens
<220> FEATURE:
<223> OTHER INFORMATION: TCR27 - TRA - CDR1

<400> SEQUENCE: 71

Thr Ile Ser Gly Thr Asp Tyr
1               5

<210> SEQ ID NO 72
<211> LENGTH: 5
<212> TYPE: PRT
<213> ORGANISM: Homo sapiens
<220> FEATURE:
<223> OTHER INFORMATION: TCR27 - TRA - CDR2

<400> SEQUENCE: 72

Gly Leu Thr Ser Asn
1               5

<210> SEQ ID NO 73
<211> LENGTH: 14
<212> TYPE: PRT
<213> ORGANISM: Homo sapiens
<220> FEATURE:
<223> OTHER INFORMATION: TCR27 - TRA - CDR3

<400> SEQUENCE: 73

-continued

Ile Leu Cys Gly Ala Gly Gly Thr Ser Tyr Gly Lys Leu Thr
1               5                    10

<210> SEQ ID NO 74
<211> LENGTH: 16
<212> TYPE: PRT
<213> ORGANISM: Homo sapiens
<220> FEATURE:
<223> OTHER INFORMATION: TCR27 - TRA - junction aa

<400> SEQUENCE: 74

Cys Ile Leu Cys Gly Ala Gly Gly Thr Ser Tyr Gly Lys Leu Thr Phe
1               5                    10                   15

<210> SEQ ID NO 75
<211> LENGTH: 114
<212> TYPE: PRT
<213> ORGANISM: Homo sapiens
<220> FEATURE:
<223> OTHER INFORMATION: TCR27 - TRA - variable region

<400> SEQUENCE: 75

Asp Ala Lys Thr Thr Gln Pro Asn Ser Met Glu Ser Asn Glu Glu Glu
1               5                    10                   15

Pro Val His Leu Pro Cys Asn His Ser Thr Ile Ser Gly Thr Asp Tyr
              20                   25                   30

Ile His Trp Tyr Arg Gln Leu Pro Ser Gln Gly Pro Glu Tyr Val Ile
              35                   40                   45

His Gly Leu Thr Ser Asn Val Asn Asn Arg Met Ala Ser Leu Ala Ile
              50                   55                   60

Ala Glu Asp Arg Lys Ser Ser Thr Leu Ile Leu His Arg Ala Thr Leu
65                   70                   75                   80

Arg Asp Ala Ala Val Tyr Tyr Cys Ile Leu Cys Gly Ala Gly Gly Thr
                    85                   90                   95

Ser Tyr Gly Lys Leu Thr Phe Gly Gln Gly Thr Ile Leu Thr Val His
              100                  105                  110

Pro Asn

<210> SEQ ID NO 76
<211> LENGTH: 5
<212> TYPE: PRT
<213> ORGANISM: Homo sapiens
<220> FEATURE:
<223> OTHER INFORMATION: TCR27 - TRB - CDR1

<400> SEQUENCE: 76

Met Asn His Glu Tyr
1               5

<210> SEQ ID NO 77
<211> LENGTH: 6
<212> TYPE: PRT
<213> ORGANISM: Homo sapiens
<220> FEATURE:
<223> OTHER INFORMATION: TCR27 - TRB - CDR2

<400> SEQUENCE: 77

Ser Met Asn Val Glu Val
1               5

<210> SEQ ID NO 78
<211> LENGTH: 12

-continued

```
<212> TYPE: PRT
<213> ORGANISM: Homo sapiens
<220> FEATURE:
<223> OTHER INFORMATION: TCR27 - TRB - CDR3

<400> SEQUENCE: 78

Ala Ser Asn Val Gln Gly Ala Asn Asn Glu Gln Phe
1               5                   10

<210> SEQ ID NO 79
<211> LENGTH: 14
<212> TYPE: PRT
<213> ORGANISM: Homo sapiens
<220> FEATURE:
<223> OTHER INFORMATION: TCR27 - TRB - junction aa

<400> SEQUENCE: 79

Cys Ala Ser Asn Val Gln Gly Ala Asn Asn Glu Gln Phe Phe
1               5                   10

<210> SEQ ID NO 80
<211> LENGTH: 113
<212> TYPE: PRT
<213> ORGANISM: Homo sapiens
<220> FEATURE:
<223> OTHER INFORMATION: TCR27 - TRB - variable region

<400> SEQUENCE: 80

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Asn Val Gln
                85                  90                  95

Gly Ala Asn Asn Glu Gln Phe Phe Gly Pro Gly Thr Arg Leu Thr Val
            100                 105                 110

Leu

<210> SEQ ID NO 81
<211> LENGTH: 7
<212> TYPE: PRT
<213> ORGANISM: Homo sapiens
<220> FEATURE:
<223> OTHER INFORMATION: TCR01 - TRA - CDR1

<400> SEQUENCE: 81

Thr Ile Ser Gly Thr Asp Tyr
1               5

<210> SEQ ID NO 82
<211> LENGTH: 5
<212> TYPE: PRT
<213> ORGANISM: Homo sapiens
<220> FEATURE:
<223> OTHER INFORMATION: TCR01 - TRA - CDR2

<400> SEQUENCE: 82
```

```
Gly Leu Thr Ser Asn
1               5

<210> SEQ ID NO 83
<211> LENGTH: 14
<212> TYPE: PRT
<213> ORGANISM: Homo sapiens
<220> FEATURE:
<223> OTHER INFORMATION: TCR01 - TRA - CDR3

<400> SEQUENCE: 83

Ile Leu Cys Gly Ala Gly Gly Thr Ser Tyr Gly Lys Leu Thr
1               5                   10

<210> SEQ ID NO 84
<211> LENGTH: 16
<212> TYPE: PRT
<213> ORGANISM: Homo sapiens
<220> FEATURE:
<223> OTHER INFORMATION: TCR01 - TRA - junction aa

<400> SEQUENCE: 84

Cys Ile Leu Cys Gly Ala Gly Gly Thr Ser Tyr Gly Lys Leu Thr Phe
1               5                   10                  15

<210> SEQ ID NO 85
<211> LENGTH: 114
<212> TYPE: PRT
<213> ORGANISM: Homo sapiens
<220> FEATURE:
<223> OTHER INFORMATION: TCR01 - TRA - variable region

<400> SEQUENCE: 85

Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Cys Gly Ala Gly Gly Thr
                85                  90                  95

Ser Tyr Gly Lys Leu Thr Phe Gly Gln Gly Thr Ile Leu Thr Val His
            100                 105                 110

Pro Asn

<210> SEQ ID NO 86
<211> LENGTH: 5
<212> TYPE: PRT
<213> ORGANISM: Homo sapiens
<220> FEATURE:
<223> OTHER INFORMATION: TCR01 - TRB - CDR1

<400> SEQUENCE: 86

Met Asn His Glu Tyr
1               5

<210> SEQ ID NO 87
<211> LENGTH: 6
<212> TYPE: PRT
```

```
<213> ORGANISM: Homo sapiens
<220> FEATURE:
<223> OTHER INFORMATION: TCR01 - TRB - CDR2

<400> SEQUENCE: 87

Ser Met Asn Val Glu Val
1               5

<210> SEQ ID NO 88
<211> LENGTH: 12
<212> TYPE: PRT
<213> ORGANISM: Homo sapiens
<220> FEATURE:
<223> OTHER INFORMATION: TCR01 - TRB - CDR3

<400> SEQUENCE: 88

Ala Ser Ala Ile Gln Gly Ala Asn Asn Glu Gln Phe
1               5                   10

<210> SEQ ID NO 89
<211> LENGTH: 14
<212> TYPE: PRT
<213> ORGANISM: Homo sapiens
<220> FEATURE:
<223> OTHER INFORMATION: TCR01 - TRB - junction aa

<400> SEQUENCE: 89

Cys Ala Ser Ala Ile Gln Gly Ala Asn Asn Glu Gln Phe Phe
1               5                   10

<210> SEQ ID NO 90
<211> LENGTH: 113
<212> TYPE: PRT
<213> ORGANISM: Homo sapiens
<220> FEATURE:
<223> OTHER INFORMATION: TCR01 - TRB - variable region

<400> SEQUENCE: 90

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
                20                  25                  30

Ser Trp Tyr Arg Gln Asp Pro Gly Leu Gly Leu Arg Gln Ile Tyr Tyr
            35                  40                  45

Ser Met Asn Val Glu Val Thr Asp Lys Gly Asp Val Pro Glu Gly Tyr
        50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ala Ile Gln
                85                  90                  95

Gly Ala Asn Asn Glu Gln Phe Phe Gly Pro Gly Thr Arg Leu Thr Val
                100                 105                 110

Leu

<210> SEQ ID NO 91
<211> LENGTH: 339
<212> TYPE: DNA
<213> ORGANISM: Artificial Sequence
<220> FEATURE:
<223> OTHER INFORMATION: DNA encoding variable region of TCR06 - TRA

<400> SEQUENCE: 91
aagcaagaag tgacccagat tcctgccgct ctgtccgtgc ctgaaggcga gaatctggtc     60
```

```
ctgaactgca gcttcaccga cagcgccatc tacaacctgc agtggttcag gcaggatccc      120
ggcaagggac tgacaagcct gctgctgatt cagagcagcc agagagagca gacctccggc      180
agactgaatg ccagcctgga taagtccagc ggcagaagca ccctgtatat cgccgcttct      240
cagcctggcg atagcgccac atatctgtgt gccgtcctga tggactccaa ctaccagctg      300
atttggggag ccggcaccaa gctgatcatc aagcccgac                             339
```

<210> SEQ ID NO 92
<211> LENGTH: 339
<212> TYPE: DNA
<213> ORGANISM: Artificial Sequence
<220> FEATURE:
<223> OTHER INFORMATION: DNA encoding variable region of TCR06 - TRB

<400> SEQUENCE: 92

```
gatgccggaa tcacacagag ccccagatac aagatcaccg agacaggccg gcaagtgacc      60
ctgatgtgtc accagacatg gtcccacagc tacatgttct ggtacagaca ggacctcggc      120
cacggcctga gactgatcta ctattctgcc gccgctgaca tcaccgacaa gggcgaagtg      180
cctgatggct acgtggtgtc cagaagcaag accgagaact tcccactgac actggaaagc      240
gccacacggt cccagaccag cgtgtacttt tgtgccagca gcgaggacgg aatgaacacc      300
gaggcctttt tcggccaagg caccagactg accgtggtg                             339
```

<210> SEQ ID NO 93
<211> LENGTH: 342
<212> TYPE: DNA
<213> ORGANISM: Artificial Sequence
<220> FEATURE:
<223> OTHER INFORMATION: DNA encoding variable region of TCR50 - TRA

<400> SEQUENCE: 93

```
gcccagagcg tgacacaact ggatagccac gtgtccgtgt ctgagggcac acctgtgctg      60
ctgagatgca actactccag cagctacagc cccagcctgt tttggtacgt gcagcaccct      120
aacaagggac tgcagctgct gctgaagtac acctctgccg ccacactggt caagggcatc      180
aatggcttcg aggccgagtt caagaagtcc gagacaagct tccacctgac caagcctagc      240
gctcacatgt ccgatgccgc cgaatacttc tgcgtggtca tggccaccgg cttccagaaa      300
ctggtgtttg gcacaggcac ccggctgctc gtgtccccaa at                        342
```

<210> SEQ ID NO 94
<211> LENGTH: 339
<212> TYPE: DNA
<213> ORGANISM: Artificial Sequence
<220> FEATURE:
<223> OTHER INFORMATION: DNA encoding variable region of TCR50 - TRB

<400> SEQUENCE: 94

```
gatagcggcg ttacccagac acctaagcac ctgatcacag ccacaggcca gcgcgtgacc      60
ctgagatgtt ctcctagaag cggcgacctg agcgtgtact ggtatcagca gtctctggac      120
cagggcctgc agttcctgat ccagtactac aacggcgagg aaagagccaa gggcaacatc      180
ctggaacggt tcagcgccca gcagttccca gatctgcaca cgcagctgaa cctgagcagc      240
ctggaactgg gagatagcgc cctgtacttc tgtgccagct ctgtgaccag cggcagcgac      300
gagcagtttt ttggccctgg caccagactg accgtgctg                             339
```

<210> SEQ ID NO 95

-continued

```
<211> LENGTH: 333
<212> TYPE: DNA
<213> ORGANISM: Artificial Sequence
<220> FEATURE:
<223> OTHER INFORMATION: DNA encoding variable region of TCR83 - TRA

<400> SEQUENCE: 95
ggccagaaca tcgatcagcc tacagagatg accgccaccg agggcgccat cgtgcagatc      60
aattgcacct accagaccag cggcttcaac ggcctgttct ggtatcagca gcatgccggc     120 gaggcccta ccttcctgag ctacaatgtg ctggacggcc tggaagaaaa gggcagattc      180
agcagcttcc tgtccagaag caagggctac tcctacctgc tgctgaaaga actgcagatg     240
aaggacagcg cctcttacct gtgtgccgcc gtgaacaacg ccggcaacat gctgacattt     300
ggcggcggaa cacggctgat ggtcaagccc cac                                  333

<210> SEQ ID NO 96
<211> LENGTH: 348
<212> TYPE: DNA
<213> ORGANISM: Artificial Sequence
<220> FEATURE:
<223> OTHER INFORMATION: DNA encoding variable region of TCR83 - TRB

<400> SEQUENCE: 96
gatacagccg tgtctcagac ccctaagtac ctggtcaccc agatgggcaa cgacaagagc      60
atcaagtgcg agcagaacct gggccacgac accatgtact ggtacaagca ggacagcaag     120
aaattcctga agatcatgtt cagctacaac aacaaagagc tgatcatcaa cgagacagtg     180
cccaaccggt tcagccctaa gagccctgat aaggcccacc tgaacctgca catcaacagc     240
ctggaactgg gcgacagcgc cgtgtacttt tgtgccagct ctcaaggcta tggcggccct     300
agcaccgaca cacagtattt cggccctggc accagactga ccgtgctg                  348

<210> SEQ ID NO 97
<211> LENGTH: 342
<212> TYPE: DNA
<213> ORGANISM: Artificial Sequence
<220> FEATURE:
<223> OTHER INFORMATION: DNA encoding variable region of TCR64 - TRA

<400> SEQUENCE: 97
acacagctgc tggaacagag cccacagttc ctgagcatcc aagagggcga gaacctgacc      60
gtgtactgca acagcagcag cgtgttcagc tccctgcagt ggtacaggca agagcctggc     120
gaaggacctg tgctgctggt cacagttgtg acaggcggcg aagtgaagaa gctgaagcgg     180
ctgaccttcc agttcggcga cgccagaaag gattccagcc tgcacattac cgctgctcag     240
ccaggcgata ccggcctgta tctttgtgct ggcgacgtcg acacaggcac cgccagcaaa     300
ctgacatttg gcaccggcac caggctgcaa gtgaccctgg ac                       342

<210> SEQ ID NO 98
<211> LENGTH: 345
<212> TYPE: DNA
<213> ORGANISM: Artificial Sequence
<220> FEATURE:
<223> OTHER INFORMATION: DNA encoding variable region of TCR64 - TRB

<400> SEQUENCE: 98
gacgtgaaag tgacacagag cagcagatac ctggtcaagc ggaccggcga gaaggtgttc      60
ctggaatgcg tgcaggacat ggaccacgag aatatgttct ggtacagaca ggaccccggc     120
ctgggcctga gactgatcta cttcagctac gacgtgaaga tgaaggaaaa gggcgacatc     180
```

-continued

```
cccgagggct acagcgtgtc cagagagaag aaagagcggt tcagcctgat cctggaaagc     240
gccagcacca accagaccag catgtacctg tgtgccagca gcctgcttgg atctggcgcc     300
ctgtacgagc agtatttcgg ccctggcacc agactgaccg tgacc                     345
```

```
<210> SEQ ID NO 99
<211> LENGTH: 342
<212> TYPE: DNA
<213> ORGANISM: Artificial Sequence
<220> FEATURE:
<223> OTHER INFORMATION: DNA encoding variable region of TCR25 - TRA

<400> SEQUENCE: 99
gcccagagcg tgacacaact ggatagccac gtgtccgtgt ctgagggcac acctgtgctg     60
ctgagatgca actactccag cagctacagc cccagcctgt tttggtacgt gcagcaccct     120
aacaagggcc tgcagctgct gctgaagtac acatctgccg ccacactggt caagggcatc     180
aatggcttcg aggccgagtt caagaagtct gagacaagct tccacctgac caagcctagc     240
gctcacatgt ccgatgccgc cgaatacttc tgcgtggcct gggataccgg cttccagaaa     300
ctggtgtttg gcaccggcac acggctgctc gtgtccccaa at                        342
```

```
<210> SEQ ID NO 100
<211> LENGTH: 336
<212> TYPE: DNA
<213> ORGANISM: Artificial Sequence
<220> FEATURE:
<223> OTHER INFORMATION: DNA encoding variable region of TCR25 - TRB

<400> SEQUENCE: 100
gagcccgaag tgacacagac acccagccac caagtgaccc agatgggcca agaagtgatc     60
ctgcgctgcg tgcccatcag caaccacctg tacttctact ggtacagaca gatcctgggc     120
cagaaagtcg agttcctggt gtccttctac aacaacgaga tcagcgagaa gtccgagatc     180
ttcgacgacc agttcagcgt ggaaagaccc gacggcagca acttcaccct gaagatcaga     240
agcaccaagc tcgaggacag cgccatgtac ttttgcgcct ctaaggccct ggccgacaca     300
cagtattttg ccctggcac cagactgacc gtgctg                               336
```

```
<210> SEQ ID NO 101
<211> LENGTH: 333
<212> TYPE: DNA
<213> ORGANISM: Artificial Sequence
<220> FEATURE:
<223> OTHER INFORMATION: DNA encoding variable region of TCR58 - TRA

<400> SEQUENCE: 101
cggaaagagg tggaacagga ccctggacct ttcaacgttc agagggcgc caccgtggcc      60 ttcaattgca cctacagcaa tagcgccagc cagagctttt tctggtatcg gcaggactgc     120
cggaaagaac ccaagctgct gatgagcgtg tacagcagcg gcaacgagga cggcagattc     180
acagcccagc tgaacagagc cagccagtac atctccctgc tgatccggga tagcaagctg     240
agcgatagcg ccacctatct gtgtgtggcc agcggcgata gcagctacaa gctgatcttt     300
ggcagcggca ccaggctgct tgtgcggccc gat                                  333
```

```
<210> SEQ ID NO 102
<211> LENGTH: 345
<212> TYPE: DNA
<213> ORGANISM: Artificial Sequence
<220> FEATURE:
```

-continued

<223> OTHER INFORMATION: DNA encoding variable region of TCR58 - TRB

<400> SEQUENCE: 102
gagcccgaag tgacacagac acccagccac caagtgaccc agatgggcca agaagtgatc      60
ctgcgctgcg tgcccatcag caaccacctg tacttctact ggtacagaca gatcctgggc      120
cagaaagtcg agttcctggt gtccttctac aacaacgaga tcagcgagaa gtccgagatc      180
ttcgacgacc agttcagcgt ggaaagaccc gacggcagca acttcaccct gaagatcaga      240
agcaccaagc tcgaggacag cgccatgtac ttttgcgcca gcagcgatcc cctgagcacc      300
tacaacgagc agttcttcgg ccctggcacc agactgaccg tgctg                      345

<210> SEQ ID NO 103
<211> LENGTH: 342
<212> TYPE: DNA
<213> ORGANISM: Artificial Sequence
<220> FEATURE:
<223> OTHER INFORMATION: DNA encoding variable region of TCR27 - TRA

<400> SEQUENCE: 103
gacgccaaga ccacacagcc caacagcatg gaaagcaacg aagaggaacc cgtgcatctg      60
ccctgcaacc acagcacaat cagcggcacc gactacatcc actggtatag acagctgccc      120
tctcagggcc ccgagtatgt gattcacgga ctgaccagca cgtgaacaa ccggatggcc      180 tctctggcca ttgccgagga cagaaagagc agcaccctga tcctgcacag agccacactg      240
agagatgccg ccgtgtacta ctgcatcctt tgtggcgctg gcggcaccag ctatggcaag      300
ctgacatttg gccagggcac catcctgacc gtgcatccca ac                        342

<210> SEQ ID NO 104
<211> LENGTH: 339
<212> TYPE: DNA
<213> ORGANISM: Artificial Sequence
<220> FEATURE:
<223> OTHER INFORMATION: DNA encoding variable region of TCR27 - TRB

<400> SEQUENCE: 104
gaagctcaag tgacacagaa ccccagatac ctgatcaccg tgaccggcaa gaaactgacc      60
gtgacctgca gccagaacat gaaccacgag tacatgagct ggtacagaca ggaccctggc      120
ctgggcctga cacagatcta ctacagcatg aacgtggaag tgaccgacaa gggcgacgtg      180
cccgagggct acaaggtgtc cagaaaagag aagcggaact tcccactgat cctggaaagc      240
ccatctccta accagaccag cctgtacttc tgcgccagca atgtgcaggg cgccaacaac      300
gagcagttct tcggccctgg caccagactg acagtgctg                            339

<210> SEQ ID NO 105
<211> LENGTH: 342
<212> TYPE: DNA
<213> ORGANISM: Artificial Sequence
<220> FEATURE:
<223> OTHER INFORMATION: DNA encoding variable region of TCR01 - TRA

<400> SEQUENCE: 105
gacgccaaga ccacacagcc caacagcatg gaaagcaacg aagaggaacc cgtgcatctg      60
ccctgcaacc acagcacaat cagcggcacc gactacatcc actggtatag acagctgccc      120
tctcagggcc ccgagtatgt gattcacgga ctgaccagca cgtgaacaa ccggatggcc      180 tctctggcca ttgccgagga cagaaagagc agcaccctga tcctgcacag agccacactg      240
agagatgccg ccgtgtacta ctgcatcctt tgtggcgctg gcggcaccag ctatggcaag      300
ctgacatttg gccagggcac catcctgacc gtgcatccca ac                    342

<210> SEQ ID NO 106
<211> LENGTH: 339
<212> TYPE: DNA
<213> ORGANISM: Artificial Sequence
<220> FEATURE:
<223> OTHER INFORMATION: DNA encoding variable region of TCR01 - TRB

<400> SEQUENCE: 106
gaagctcaag tgacacagaa ccccagatac ctgatcaccg tgaccggcaa gaaactgacc     60
gtgacctgca gccagaacat gaaccacgag tacatgagct ggtacagaca ggaccctggc    120
ctgggcctga cagatctca ctacagcatg aacgtggaag tgaccgacaa gggcgacgtg    180
cccgagggct acaaggtgtc cagaaaagag aagcggaact tcccactgat cctggaaagc    240
ccatctccta accagaccag cctgtacttc tgcgccagcg ctattcaggg cgccaacaac    300
gagcagttct tcggccctgg caccagactg acagtgctg                          339

<210> SEQ ID NO 107
<211> LENGTH: 9
<212> TYPE: PRT
<213> ORGANISM: Homo sapiens

<400> SEQUENCE: 107

Trp Thr Leu Leu Val Asp Leu Leu Trp
1               5

<210> SEQ ID NO 108
<211> LENGTH: 10
<212> TYPE: PRT
<213> ORGANISM: Homo sapiens

<400> SEQUENCE: 108

Ile Ala Leu Tyr Leu Gln Gln Asn Trp Trp
1               5                   10

<210> SEQ ID NO 109
<211> LENGTH: 10
<212> TYPE: PRT
<213> ORGANISM: Homo sapiens

<400> SEQUENCE: 109

Trp Trp Thr Leu Leu Val Asp Leu Leu Trp
1               5                   10

<210> SEQ ID NO 110
<211> LENGTH: 10
<212> TYPE: PRT
<213> ORGANISM: Homo sapiens

<400> SEQUENCE: 110

Ile Ile Ala Leu Tyr Leu Gln Gln Asn Trp
1               5                   10

<210> SEQ ID NO 111
<211> LENGTH: 10
<212> TYPE: PRT
<213> ORGANISM: Homo sapiens

<400> SEQUENCE: 111

Trp Thr Leu Leu Val Asp Leu Leu Trp Leu
1               5                   10

-continued

```
<210> SEQ ID NO 112
<211> LENGTH: 9
<212> TYPE: PRT
<213> ORGANISM: Homo sapiens

<400> SEQUENCE: 112

Leu Ala Ile Leu Ile Trp Met Tyr Tyr
1               5

<210> SEQ ID NO 113
<211> LENGTH: 9
<212> TYPE: PRT
<213> ORGANISM: Homo sapiens

<400> SEQUENCE: 113

Leu Leu Phe Leu Ala Ile Leu Ile Trp
1               5

<210> SEQ ID NO 114
<211> LENGTH: 10
<212> TYPE: PRT
<213> ORGANISM: Homo sapiens

<400> SEQUENCE: 114

Leu Leu Leu Phe Leu Ala Ile Leu Ile Trp
1               5                   10

<210> SEQ ID NO 115
<211> LENGTH: 10
<212> TYPE: PRT
<213> ORGANISM: Homo sapiens

<400> SEQUENCE: 115

Leu Ala Ile Leu Ile Trp Met Tyr Tyr His
1               5                   10

<210> SEQ ID NO 116
<211> LENGTH: 9
<212> TYPE: PRT
<213> ORGANISM: Homo sapiens

<400> SEQUENCE: 116

Ala Leu Tyr Leu Gln Gln Asn Trp Trp
1               5

<210> SEQ ID NO 117
<211> LENGTH: 10
<212> TYPE: PRT
<213> ORGANISM: Homo sapiens

<400> SEQUENCE: 117

Phe Leu Ala Ile Leu Ile Trp Met Tyr Tyr
1               5                   10

<210> SEQ ID NO 118
<211> LENGTH: 9
<212> TYPE: PRT
<213> ORGANISM: Homo sapiens

<400> SEQUENCE: 118

Asn Ser Asn Glu Gly Arg His His Leu
1               5
```

<210> SEQ ID NO 119
<211> LENGTH: 497
<212> TYPE: PRT
<213> ORGANISM: Homo sapiens
<220> FEATURE:
<223> OTHER INFORMATION: LMP2A

<400> SEQUENCE: 119

Met Gly Ser Leu Glu Met Val Pro Met Gly Ala Gly Pro Pro Ser Pro
1               5                   10                  15

Gly Gly Asp Pro Asp Gly Tyr Asp Gly Gly Asn Asn Ser Gln Tyr Pro
            20                  25                  30

Ser Ala Ser Gly Ser Ser Gly Asn Thr Pro Thr Pro Pro Asn Asp Glu
        35                  40                  45

Glu Arg Glu Ser Asn Glu Glu Pro Pro Pro Pro Tyr Glu Asp Pro Tyr
    50                  55                  60

Trp Gly Asn Gly Asp Arg His Ser Asp Tyr Gln Pro Leu Gly Thr Gln
65                  70                  75                  80

Asp Gln Ser Leu Tyr Leu Gly Leu Gln His Asp Gly Asn Asp Gly Leu
                85                  90                  95

Pro Pro Pro Pro Tyr Ser Pro Arg Asp Asp Ser Ser Gln His Ile Tyr
            100                 105                 110

Glu Glu Ala Gly Arg Gly Ser Met Asn Pro Val Cys Leu Pro Val Ile
            115                 120                 125

Val Ala Pro Tyr Leu Phe Trp Leu Ala Ala Ile Ala Ala Ser Cys Phe
        130                 135                 140

Thr Ala Ser Val Ser Thr Val Val Thr Ala Thr Gly Leu Ala Leu Ser
145                 150                 155                 160

Leu Leu Leu Leu Ala Ala Val Ala Ser Ser Tyr Ala Ala Ala Gln Arg
                165                 170                 175

Lys Leu Leu Thr Pro Val Thr Val Leu Thr Ala Val Val Thr Phe Phe
            180                 185                 190

Ala Ile Cys Leu Thr Trp Arg Ile Glu Asp Pro Pro Phe Asn Ser Leu
            195                 200                 205

Leu Phe Ala Leu Leu Ala Ala Ala Gly Gly Leu Gln Gly Ile Tyr Val
        210                 215                 220

Leu Val Met Leu Val Leu Leu Ile Leu Ala Tyr Arg Arg Arg Trp Arg
225                 230                 235                 240

Arg Leu Thr Val Cys Gly Gly Ile Met Phe Leu Ala Cys Val Leu Val
                245                 250                 255

Leu Ile Val Asp Ala Val Leu Gln Leu Ser Pro Leu Leu Gly Ala Val
            260                 265                 270

Thr Val Val Ser Met Thr Leu Leu Leu Leu Ala Phe Val Leu Trp Leu
            275                 280                 285

Ser Ser Pro Gly Gly Leu Gly Thr Leu Gly Ala Ala Leu Leu Thr Leu
        290                 295                 300

Ala Ala Ala Leu Ala Leu Leu Ala Ser Leu Ile Leu Gly Thr Leu Asn
305                 310                 315                 320

Leu Thr Thr Met Phe Leu Leu Met Leu Leu Trp Thr Leu Val Val Leu
                325                 330                 335

Leu Ile Cys Ser Ser Cys Ser Ser Cys Pro Leu Ser Lys Ile Leu Leu
            340                 345                 350

Ala Arg Leu Phe Leu Tyr Ala Leu Ala Leu Leu Leu Leu Ala Ser Ala
            355                 360                 365

Leu Ile Ala Gly Gly Ser Ile Leu Gln Thr Asn Phe Lys Ser Leu Ser

-continued

```
          370             375             380
Ser Thr Glu Phe Ile Pro Asn Leu Phe Cys Met Leu Leu Leu Ile Val
385             390             395             400

Ala Gly Ile Leu Phe Ile Leu Ala Ile Leu Thr Glu Trp Gly Ser Gly
                405             410             415

Asn Arg Thr Tyr Gly Pro Val Phe Met Cys Leu Gly Gly Leu Leu Thr
            420             425             430

Met Val Ala Gly Ala Val Trp Leu Thr Val Met Ser Asn Thr Leu Leu
        435             440             445

Ser Ala Trp Ile Leu Thr Ala Gly Phe Leu Ile Phe Leu Ile Gly Phe
        450             455             460

Ala Leu Phe Gly Val Ile Arg Cys Cys Arg Tyr Cys Cys Tyr Tyr Cys
465             470             475             480

Leu Thr Leu Glu Ser Glu Glu Arg Pro Pro Thr Pro Tyr Arg Asn Thr
            485             490             495

Val
```

<210> SEQ ID NO 120
<211> LENGTH: 386
<212> TYPE: PRT
<213> ORGANISM: Homo sapiens
<220> FEATURE:
<223> OTHER INFORMATION: LMP1

<400> SEQUENCE: 120

```
Met Glu His Asp Leu Glu Arg Gly Pro Pro Gly Pro Arg Arg Pro Pro
1               5               10              15

Arg Gly Pro Pro Leu Ser Ser Ser Leu Gly Leu Ala Leu Leu Leu Leu
            20              25              30

Leu Leu Ala Leu Leu Phe Trp Leu Tyr Ile Val Met Ser Asp Trp Thr
        35              40              45

Gly Gly Ala Leu Leu Val Leu Tyr Ser Phe Ala Leu Met Leu Ile Ile
        50              55              60

Ile Ile Leu Ile Ile Phe Ile Phe Arg Arg Asp Leu Leu Cys Pro Leu
65              70              75              80

Gly Ala Leu Cys Ile Leu Leu Leu Met Ile Thr Leu Leu Leu Ile Ala
                85              90              95

Leu Trp Asn Leu His Gly Gln Ala Leu Phe Leu Gly Ile Val Leu Phe
            100             105             110

Ile Phe Gly Cys Leu Leu Val Leu Gly Ile Trp Ile Tyr Leu Leu Glu
        115             120             125

Met Leu Trp Arg Leu Gly Ala Thr Ile Trp Gln Leu Leu Ala Phe Phe
        130             135             140

Leu Ala Phe Phe Leu Asp Leu Ile Leu Leu Ile Ile Ala Leu Tyr Leu
145             150             155             160

Gln Gln Asn Trp Trp Thr Leu Leu Val Asp Leu Leu Trp Leu Leu Leu
            165             170             175

Phe Leu Ala Ile Leu Ile Trp Met Tyr Tyr His Gly Gln Arg His Ser
            180             185             190

Asp Glu His His His Asp Asp Ser Leu Pro His Pro Gln Gln Ala Thr
            195             200             205

Asp Asp Ser Gly His Glu Ser Asp Ser Asn Ser Asn Glu Gly Arg His
        210             215             220

His Leu Leu Val Ser Gly Ala Gly Asp Gly Pro Pro Leu Cys Ser Gln
225             230             235             240
```

Asn Leu Gly Ala Pro Gly Gly Pro Asp Asn Gly Pro Gln Asp Pro
                245                 250                 255

Asp Asn Thr Asp Asp Asn Gly Pro Gln Asp Pro Asp Asn Thr Asp Asp
                260                 265                 270

Asn Gly Pro His Asp Pro Leu Pro Gln Asp Pro Asp Asn Thr Asp Asp
                275                 280                 285

Asn Gly Pro Gln Asp Pro Asp Asn Thr Asp Asp Asn Gly Pro His Asp
        290                 295                 300

Pro Leu Pro His Ser Pro Ser Asp Ser Ala Gly Asn Asp Gly Gly Pro
305                 310                 315                 320

Pro Gln Leu Thr Glu Glu Val Glu Asn Lys Gly Gly Asp Gln Gly Pro
                325                 330                 335

Pro Leu Met Thr Asp Gly Gly Gly Gly His Ser His Asp Ser Gly His
                340                 345                 350

Gly Gly Gly Asp Pro His Leu Pro Thr Leu Leu Gly Ser Ser Gly
        355                 360                 365

Ser Gly Gly Asp Asp Asp Asp Pro His Gly Pro Val Gln Leu Ser Tyr
    370                 375                 380

Tyr Asp
385

<210> SEQ ID NO 121
<211> LENGTH: 992
<212> TYPE: PRT
<213> ORGANISM: Homo sapiens
<220> FEATURE:
<223> OTHER INFORMATION: EBNA3C

<400> SEQUENCE: 121

Met Glu Ser Phe Glu Gly Gln Gly Asp Ser Arg Gln Ser Pro Asp Asn
1               5                   10                  15

Glu Arg Gly Asp Asn Val Gln Thr Thr Gly Glu His Asp Gln Asp Pro
                20                  25                  30

Gly Pro Gly Pro Pro Ser Ser Gly Ala Ser Glu Arg Leu Val Pro Glu
        35                  40                  45

Glu Ser Tyr Ser Arg Asp Gln Gln Pro Trp Gly Gln Ser Arg Gly Asp
    50                  55                  60

Glu Asn Arg Gly Trp Met Gln Arg Ile Arg Arg Arg Arg Arg Arg
65                  70                  75                  80

Ala Ala Leu Ser Gly His Leu Leu Asp Thr Glu Asp Asn Val Pro Pro
                85                  90                  95

Trp Leu Pro Pro His Asp Ile Thr Pro Tyr Thr Ala Arg Asn Ile Arg
                100                 105                 110

Asp Ala Ala Cys Arg Ala Val Lys Gln Ser His Leu Gln Ala Leu Ser
        115                 120                 125

Asn Leu Ile Leu Asp Ser Gly Leu Asp Thr Gln His Ile Leu Cys Phe
    130                 135                 140

Val Met Ala Ala Arg Gln Arg Leu Gln Asp Ile Arg Arg Gly Pro Leu
145                 150                 155                 160

Val Ala Glu Gly Gly Val Gly Trp Arg His Trp Leu Leu Thr Ser Pro
                165                 170                 175

Ser Gln Ser Trp Pro Met Gly Tyr Arg Thr Ala Thr Leu Arg Thr Leu
                180                 185                 190

Thr Pro Val Pro Asn Arg Val Gly Ala Asp Ser Ile Met Leu Thr Ala
        195                 200                 205

-continued

```
Thr Phe Gly Cys Gln Asn Ala Ala Arg Thr Leu Asn Thr Phe Ser Ala
    210             215                 220

Thr Val Trp Thr Pro Pro His Ala Gly Pro Arg Glu Gln Glu Arg Tyr
225             230                 235                 240

Ala Arg Glu Ala Glu Val Arg Phe Leu Arg Gly Lys Trp Gln Arg Arg
                245                 250                 255

Tyr Arg Arg Ile Tyr Asp Leu Ile Glu Leu Cys Gly Ser Leu His His
                260                 265                 270

Ile Trp Gln Asn Leu Leu Gln Thr Glu Glu Asn Leu Leu Asp Phe Val
            275                 280                 285

Arg Phe Met Gly Val Met Ser Ser Cys Asn Asn Pro Ala Val Asn Tyr
    290             295                 300

Trp Phe His Lys Thr Ile Gly Asn Phe Lys Pro Tyr Tyr Pro Trp Asn
305             310                 315                 320

Ala Pro Pro Asn Glu Asn Pro Tyr His Ala Arg Arg Gly Ile Lys Glu
                325                 330                 335

His Val Ile Gln Asn Ala Phe Arg Lys Ala Gln Ile Gln Gly Leu Ser
            340                 345                 350

Met Leu Ala Thr Gly Gly Glu Pro Arg Gly Asp Ala Thr Ser Glu Thr
            355                 360                 365

Ser Ser Asp Glu Asp Thr Gly Arg Gln Gly Ser Asp Val Glu Leu Glu
    370                 375                 380

Ser Ser Asp Asp Glu Leu Pro Tyr Ile Asp Pro Asn Met Glu Pro Val
385                 390                 395                 400

Gln Gln Arg Pro Val Met Phe Val Ser Arg Val Pro Ala Lys Lys Pro
                405                 410                 415

Arg Lys Leu Pro Trp Pro Thr Pro Lys Thr His Pro Val Lys Arg Thr
                420                 425                 430

Asn Val Lys Thr Ser Asp Arg Ser Asp Lys Ala Glu Ala Gln Ser Thr
            435                 440                 445

Pro Glu Arg Pro Gly Pro Ser Glu Gln Ser Ser Val Thr Val Glu Pro
    450                 455                 460

Ala His Pro Thr Pro Val Glu Met Pro Met Val Ile Leu His Gln Pro
465                 470                 475                 480

Pro Pro Val Pro Lys Pro Val Pro Val Lys Pro Thr Pro Pro Pro Ser
                485                 490                 495

Arg Arg Arg Arg Gly Ala Cys Val Val Tyr Asp Asp Asp Val Ile Glu
                500                 505                 510

Val Ile Asp Val Glu Thr Thr Glu Asp Ser Ser Ser Val Ser Gln Pro
            515                 520                 525

Asn Lys Pro His Arg Lys His Gln Asp Gly Phe Gln Arg Ser Gly Arg
    530                 535                 540

Arg Gln Lys Arg Ala Ala Pro Pro Thr Val Ser Pro Ser Asp Thr Gly
545                 550                 555                 560

Pro Pro Ala Val Gly Pro Pro Ala Ala Gly Pro Pro Ala Ala Gly Pro
                565                 570                 575

Pro Ala Ala Gly Pro Pro Ala Ala Gly Pro Pro Ala Ala Gly Pro Pro
            580                 585                 590

Ala Ala Gly Pro Arg Ile Leu Ala Pro Leu Ser Ala Gly Pro Pro Ala
            595                 600                 605

Ala Gly Pro His Ile Val Thr Pro Pro Ser Ala Arg Pro Arg Ile Met
    610                 615                 620
```

```
Ala Pro Pro Val Val Arg Met Phe Met Arg Glu Arg Gln Leu Pro Gln
625             630             635             640

Ser Thr Gly Arg Lys Pro Gln Cys Phe Trp Glu Met Arg Ala Gly Arg
                645             650             655

Glu Ile Thr Gln Met Gln Gln Glu Pro Ser Ser His Leu Gln Ser Ala
            660             665             670

Thr Gln Pro Thr Thr Pro Arg Pro Ser Trp Ala Pro Ser Val Cys Ala
        675             680             685

Leu Ser Val Met Asp Ala Gly Lys Ala Gln Pro Ile Glu Ser Ser His
    690             695             700

Leu Ser Ser Met Ser Pro Thr Gln Pro Ile Ser His Glu Glu Gln Pro
705             710             715             720

Arg Tyr Glu Asp Pro Asp Ala Pro Leu Asp Leu Ser Leu His Pro Asp
                725             730             735

Val Ala Ala Gln Pro Ala Pro Gln Ala Pro Tyr Gln Gly Tyr Gln Glu
            740             745             750

Pro Pro Ala Pro Gln Ala Pro Tyr Gln Gly Tyr Gln Glu Pro Pro Pro
        755             760             765

Pro Gln Ala Pro Tyr Gln Gly Tyr Gln Glu Pro Pro Ala His Gly Leu
    770             775             780

Gln Ser Ser Ser Tyr Pro Gly Tyr Ala Gly Pro Trp Thr Pro Arg Ser
785             790             795             800

Gln His Pro Cys Tyr Arg His Pro Trp Ala Pro Trp Ser Gln Asp Pro
                805             810             815

Val His Gly His Thr Gln Gly Pro Trp Asp Pro Arg Ala Pro His Leu
            820             825             830

Pro Pro Gln Trp Asp Gly Ser Ala Gly His Gly Gln Asp Gln Val Ser
        835             840             845

Gln Phe Pro His Leu Gln Ser Glu Thr Gly Pro Pro Arg Leu Gln Leu
    850             855             860

Ser Leu Val Pro Leu Val Ser Ser Ser Ala Pro Ser Trp Ser Ser Pro
865             870             875             880

Gln Pro Arg Ala Pro Ile Arg Pro Ile Pro Thr Arg Phe Pro Pro Pro
                885             890             895

Pro Met Pro Leu Gln Asp Ser Met Ala Val Gly Cys Asp Ser Ser Gly
            900             905             910

Thr Ala Cys Pro Ser Met Pro Phe Ala Ser Asp Tyr Ser Gln Gly Ala
        915             920             925

Phe Thr Pro Leu Asp Ile Asn Ala Thr Thr Pro Lys Arg Pro Arg Val
    930             935             940

Glu Glu Ser Ser His Gly Pro Ala Arg Cys Ser Gln Ala Thr Ala Glu
945             950             955             960

Ala Gln Glu Ile Leu Ser Asp Asn Ser Glu Ile Ser Val Phe Pro Lys
                965             970             975

Asp Ala Lys Gln Thr Asp Tyr Asp Ala Ser Thr Glu Ser Glu Leu Asp
            980             985             990

<210> SEQ ID NO 122
<211> LENGTH: 14
<212> TYPE: PRT
<213> ORGANISM: Homo sapiens

<400> SEQUENCE: 122

Ala Met Ser Asp Leu Tyr Ala Gly Asn Asn Arg Lys Leu Ile
1               5               10
```

```
<210> SEQ ID NO 123
<211> LENGTH: 11
<212> TYPE: PRT
<213> ORGANISM: Homo sapiens

<400> SEQUENCE: 123

Ala Leu Thr Phe Leu Arg Asp Asp Lys Ile Ile
1               5                   10

<210> SEQ ID NO 124
<211> LENGTH: 15
<212> TYPE: PRT
<213> ORGANISM: Homo sapiens

<400> SEQUENCE: 124

Ala Ser Ser Gln Asp Ala Arg Val Ser Gly Ala Asn Val Leu Thr
1               5                   10                  15

<210> SEQ ID NO 125
<211> LENGTH: 12
<212> TYPE: PRT
<213> ORGANISM: Homo sapiens

<400> SEQUENCE: 125

Ala Ser Ser Val Thr Ser Gly Ser Asp Glu Gln Phe
1               5                   10

<210> SEQ ID NO 126
<211> LENGTH: 13
<212> TYPE: PRT
<213> ORGANISM: Homo sapiens

<400> SEQUENCE: 126

Ala Ser Ser Phe Ser Leu Gly His Ser Tyr Glu Gln Tyr
1               5                   10

<210> SEQ ID NO 127
<211> LENGTH: 9
<212> TYPE: PRT
<213> ORGANISM: Homo sapiens

<400> SEQUENCE: 127

Gln Pro Arg Ala Pro Ile Arg Pro Ile
1               5

<210> SEQ ID NO 128
<211> LENGTH: 12
<212> TYPE: PRT
<213> ORGANISM: Homo sapiens

<400> SEQUENCE: 128

Arg Pro Ile Pro Thr Arg Phe Pro Pro Pro Met
1               5                   10

<210> SEQ ID NO 129
<211> LENGTH: 12
<212> TYPE: PRT
<213> ORGANISM: Homo sapiens

<400> SEQUENCE: 129

Arg Pro Arg Val Glu Glu Ser Ser His Gly Pro Ala
1               5                   10
```

```
<210> SEQ ID NO 130
<211> LENGTH: 8
<212> TYPE: PRT
<213> ORGANISM: Homo sapiens

<400> SEQUENCE: 130

Ser Pro Gln Pro Arg Ala Pro Ile
1               5

<210> SEQ ID NO 131
<211> LENGTH: 11
<212> TYPE: PRT
<213> ORGANISM: Homo sapiens

<400> SEQUENCE: 131

Ser Pro Gln Pro Arg Ala Pro Ile Arg Pro Ile
1               5                   10

<210> SEQ ID NO 132
<211> LENGTH: 12
<212> TYPE: PRT
<213> ORGANISM: Homo sapiens

<400> SEQUENCE: 132

Ser Pro Gln Pro Arg Ala Pro Ile Arg Pro Ile Pro
1               5                   10

<210> SEQ ID NO 133
<211> LENGTH: 10
<212> TYPE: PRT
<213> ORGANISM: Homo sapiens

<400> SEQUENCE: 133

Pro Gln Pro Arg Ala Pro Ile Arg Pro Ile
1               5                   10

<210> SEQ ID NO 134
<211> LENGTH: 10
<212> TYPE: PRT
<213> ORGANISM: Homo sapiens

<400> SEQUENCE: 134

Gln Pro Arg Ala Pro Ile Arg Pro Ile Pro
1               5                   10

<210> SEQ ID NO 135
<211> LENGTH: 8
<212> TYPE: PRT
<213> ORGANISM: Homo sapiens

<400> SEQUENCE: 135

Pro Arg Ala Pro Ile Arg Pro Ile
1               5

<210> SEQ ID NO 136
<211> LENGTH: 10
<212> TYPE: PRT
<213> ORGANISM: Homo sapiens

<400> SEQUENCE: 136

Ala Pro Ile Arg Pro Ile Pro Thr Arg Phe
1               5                   10

<210> SEQ ID NO 137
<211> LENGTH: 8
```

-continued

```
<212> TYPE: PRT
<213> ORGANISM: Homo sapiens

<400> SEQUENCE: 137

Phe Pro Pro Pro Pro Met Pro Leu
1               5

<210> SEQ ID NO 138
<211> LENGTH: 10
<212> TYPE: PRT
<213> ORGANISM: Homo sapiens

<400> SEQUENCE: 138

His Gly Pro Ala Arg Cys Ser Gln Ala Thr
1               5                   10

<210> SEQ ID NO 139
<211> LENGTH: 9
<212> TYPE: PRT
<213> ORGANISM: Homo sapiens

<400> SEQUENCE: 139

Arg Pro Ile Pro Thr Arg Phe Pro Pro
1               5

<210> SEQ ID NO 140
<211> LENGTH: 8
<212> TYPE: PRT
<213> ORGANISM: Homo sapiens

<400> SEQUENCE: 140

Arg Pro Ile Pro Thr Arg Phe Pro
1               5

<210> SEQ ID NO 141
<211> LENGTH: 11
<212> TYPE: PRT
<213> ORGANISM: Homo sapiens

<400> SEQUENCE: 141

Ile Pro Thr Arg Phe Pro Pro Pro Pro Met Pro
1               5                   10

<210> SEQ ID NO 142
<211> LENGTH: 11
<212> TYPE: PRT
<213> ORGANISM: Homo sapiens

<400> SEQUENCE: 142

Pro Ile Pro Thr Arg Phe Pro Pro Pro Pro Met
1               5                   10

<210> SEQ ID NO 143
<211> LENGTH: 12
<212> TYPE: PRT
<213> ORGANISM: Homo sapiens

<400> SEQUENCE: 143

Ile Pro Thr Arg Phe Pro Pro Pro Pro Met Pro Leu
1               5                   10

<210> SEQ ID NO 144
<211> LENGTH: 10
<212> TYPE: PRT
<213> ORGANISM: Homo sapiens
```

-continued

<400> SEQUENCE: 144

Gly Pro Ala Arg Cys Ser Gln Ala Thr Ala
1               5                   10

<210> SEQ ID NO 145
<211> LENGTH: 12
<212> TYPE: PRT
<213> ORGANISM: Homo sapiens

<400> SEQUENCE: 145

Phe Pro Pro Pro Pro Met Pro Leu Gln Asp Ser Met
1               5                   10

<210> SEQ ID NO 146
<211> LENGTH: 9
<212> TYPE: PRT
<213> ORGANISM: Homo sapiens

<400> SEQUENCE: 146

Pro Pro Met Pro Leu Gln Asp Ser Met
1               5

<210> SEQ ID NO 147
<211> LENGTH: 10
<212> TYPE: PRT
<213> ORGANISM: Homo sapiens

<400> SEQUENCE: 147

Arg Pro Ile Pro Thr Arg Phe Pro Pro Pro
1               5                   10

<210> SEQ ID NO 148
<211> LENGTH: 10
<212> TYPE: PRT
<213> ORGANISM: Homo sapiens

<400> SEQUENCE: 148

Met Pro Leu Gln Asp Ser Met Ala Val Gly
1               5                   10

<210> SEQ ID NO 149
<211> LENGTH: 12
<212> TYPE: PRT
<213> ORGANISM: Homo sapiens

<400> SEQUENCE: 149

Pro Ile Pro Thr Arg Phe Pro Pro Pro Met Pro
1               5                   10

<210> SEQ ID NO 150
<211> LENGTH: 10
<212> TYPE: PRT
<213> ORGANISM: Homo sapiens

<400> SEQUENCE: 150

Pro Met Pro Leu Gln Asp Ser Met Ala Val
1               5                   10

<210> SEQ ID NO 151
<211> LENGTH: 8
<212> TYPE: PRT
<213> ORGANISM: Homo sapiens

<400> SEQUENCE: 151

Pro Met Pro Leu Gln Asp Ser Met
1               5

<210> SEQ ID NO 152
<211> LENGTH: 11
<212> TYPE: PRT
<213> ORGANISM: Homo sapiens

<400> SEQUENCE: 152

Gln Pro Arg Ala Pro Ile Arg Pro Ile Pro Thr
1               5               10

<210> SEQ ID NO 153
<211> LENGTH: 8
<212> TYPE: PRT
<213> ORGANISM: Homo sapiens

<400> SEQUENCE: 153

Gln Pro Arg Ala Pro Ile Arg Pro
1               5

<210> SEQ ID NO 154
<211> LENGTH: 9
<212> TYPE: PRT
<213> ORGANISM: Homo sapiens

<400> SEQUENCE: 154

Arg Ala Pro Ile Arg Pro Ile Pro Thr
1               5

<210> SEQ ID NO 155
<211> LENGTH: 10
<212> TYPE: PRT
<213> ORGANISM: Homo sapiens

<400> SEQUENCE: 155

Ser Glu Arg Leu Val Pro Glu Glu Ser Tyr
1               5               10

<210> SEQ ID NO 156
<211> LENGTH: 10
<212> TYPE: PRT
<213> ORGANISM: Homo sapiens

<400> SEQUENCE: 156

Trp Leu Leu Thr Ser Pro Ser Gln Ser Trp
1               5               10

<210> SEQ ID NO 157
<211> LENGTH: 9
<212> TYPE: PRT
<213> ORGANISM: Homo sapiens

<400> SEQUENCE: 157

Leu Leu Thr Ser Pro Ser Gln Ser Trp
1               5

<210> SEQ ID NO 158
<211> LENGTH: 9
<212> TYPE: PRT
<213> ORGANISM: Homo sapiens

<400> SEQUENCE: 158

Arg Arg Tyr Arg Arg Ile Tyr Asp Leu

```
1               5

<210> SEQ ID NO 159
<211> LENGTH: 9
<212> TYPE: PRT
<213> ORGANISM: Homo sapiens

<400> SEQUENCE: 159

Ala Arg Glu Ala Glu Val Arg Phe Leu
1               5

<210> SEQ ID NO 160
<211> LENGTH: 9
<212> TYPE: PRT
<213> ORGANISM: Homo sapiens

<400> SEQUENCE: 160

Leu Arg Gly Lys Trp Gln Arg Arg Tyr
1               5

<210> SEQ ID NO 161
<211> LENGTH: 9
<212> TYPE: PRT
<213> ORGANISM: Homo sapiens

<400> SEQUENCE: 161

Glu Arg Tyr Ala Arg Glu Ala Glu Val
1               5

<210> SEQ ID NO 162
<211> LENGTH: 9
<212> TYPE: PRT
<213> ORGANISM: Homo sapiens

<400> SEQUENCE: 162

Ser Arg Arg Arg Arg Gly Ala Cys Val
1               5

<210> SEQ ID NO 163
<211> LENGTH: 9
<212> TYPE: PRT
<213> ORGANISM: Homo sapiens

<400> SEQUENCE: 163

Asn Leu Leu Asp Phe Val Arg Phe Met
1               5

<210> SEQ ID NO 164
<211> LENGTH: 9
<212> TYPE: PRT
<213> ORGANISM: Homo sapiens

<400> SEQUENCE: 164

Arg Arg Ile Tyr Asp Leu Ile Glu Leu
1               5

<210> SEQ ID NO 165
<211> LENGTH: 9
<212> TYPE: PRT
<213> ORGANISM: Homo sapiens

<400> SEQUENCE: 165

Arg Arg Arg Arg Gly Ala Cys Val Val
1               5
```

<210> SEQ ID NO 166
<211> LENGTH: 9
<212> TYPE: PRT
<213> ORGANISM: Homo sapiens

<400> SEQUENCE: 166

Val Arg Phe Leu Arg Gly Lys Trp Gln
1               5

<210> SEQ ID NO 167
<211> LENGTH: 9
<212> TYPE: PRT
<213> ORGANISM: Homo sapiens

<400> SEQUENCE: 167

Arg Arg Arg Gly Ala Cys Val Val Tyr
1               5

<210> SEQ ID NO 168
<211> LENGTH: 9
<212> TYPE: PRT
<213> ORGANISM: Homo sapiens

<400> SEQUENCE: 168

Gln Arg Arg Tyr Arg Arg Ile Tyr Asp
1               5

<210> SEQ ID NO 169
<211> LENGTH: 9
<212> TYPE: PRT
<213> ORGANISM: Homo sapiens

<400> SEQUENCE: 169

Val Arg Phe Met Gly Val Met Ser Ser
1               5

<210> SEQ ID NO 170
<211> LENGTH: 10
<212> TYPE: PRT
<213> ORGANISM: Homo sapiens

<400> SEQUENCE: 170

Tyr Ala Arg Glu Ala Glu Val Arg Phe Leu
1               5                   10

<210> SEQ ID NO 171
<211> LENGTH: 9
<212> TYPE: PRT
<213> ORGANISM: Homo sapiens

<400> SEQUENCE: 171

Asn Arg Val Gly Ala Asp Ser Ile Met
1               5

<210> SEQ ID NO 172
<211> LENGTH: 9
<212> TYPE: PRT
<213> ORGANISM: Homo sapiens

<400> SEQUENCE: 172

Leu His His Ile Trp Gln Asn Leu Leu
1               5

<210> SEQ ID NO 173

```
<211> LENGTH: 9
<212> TYPE: PRT
<213> ORGANISM: Homo sapiens

<400> SEQUENCE: 173

Arg Arg Gly Ile Lys Glu His Val Ile
1               5

<210> SEQ ID NO 174
<211> LENGTH: 9
<212> TYPE: PRT
<213> ORGANISM: Homo sapiens

<400> SEQUENCE: 174

Tyr Arg Arg Ile Tyr Asp Leu Ile Glu
1               5

<210> SEQ ID NO 175
<211> LENGTH: 10
<212> TYPE: PRT
<213> ORGANISM: Homo sapiens

<400> SEQUENCE: 175

Arg Arg Tyr Arg Arg Ile Tyr Asp Leu Ile
1               5                   10

<210> SEQ ID NO 176
<211> LENGTH: 9
<212> TYPE: PRT
<213> ORGANISM: Homo sapiens

<400> SEQUENCE: 176

Ala Arg Arg Gly Ile Lys Glu His Val
1               5

<210> SEQ ID NO 177
<211> LENGTH: 10
<212> TYPE: PRT
<213> ORGANISM: Homo sapiens

<400> SEQUENCE: 177

Gln Arg Arg Tyr Arg Arg Ile Tyr Asp Leu
1               5                   10

<210> SEQ ID NO 178
<211> LENGTH: 9
<212> TYPE: PRT
<213> ORGANISM: Homo sapiens

<400> SEQUENCE: 178

Trp Gln Arg Arg Tyr Arg Arg Ile Tyr
1               5

<210> SEQ ID NO 179
<211> LENGTH: 10
<212> TYPE: PRT
<213> ORGANISM: Homo sapiens

<400> SEQUENCE: 179

Phe Leu Arg Gly Lys Trp Gln Arg Arg Tyr
1               5                   10

<210> SEQ ID NO 180
<211> LENGTH: 9
<212> TYPE: PRT
```

-continued

<213> ORGANISM: Homo sapiens

<400> SEQUENCE: 180

Arg Arg Gly Ala Cys Val Val Tyr Asp
1               5

<210> SEQ ID NO 181
<211> LENGTH: 9
<212> TYPE: PRT
<213> ORGANISM: Homo sapiens

<400> SEQUENCE: 181

Val Tyr Asp Asp Asp Val Ile Glu Val
1               5

<210> SEQ ID NO 182
<211> LENGTH: 9
<212> TYPE: PRT
<213> ORGANISM: Homo sapiens

<400> SEQUENCE: 182

Tyr Ala Arg Glu Ala Glu Val Arg Phe
1               5

<210> SEQ ID NO 183
<211> LENGTH: 9
<212> TYPE: PRT
<213> ORGANISM: Homo sapiens

<400> SEQUENCE: 183

Gly Cys Gln Asn Ala Ala Arg Thr Leu
1               5

<210> SEQ ID NO 184
<211> LENGTH: 9
<212> TYPE: PRT
<213> ORGANISM: Homo sapiens

<400> SEQUENCE: 184

Asn Ser Asn Glu Gly Arg His His Leu
1               5

<210> SEQ ID NO 185
<211> LENGTH: 9
<212> TYPE: PRT
<213> ORGANISM: Homo sapiens

<400> SEQUENCE: 185

Asp Ser Leu Pro His Pro Gln Gln Ala
1               5

<210> SEQ ID NO 186
<211> LENGTH: 9
<212> TYPE: PRT
<213> ORGANISM: Homo sapiens

<400> SEQUENCE: 186

Tyr Leu Gln Gln Asn Trp Trp Thr Leu
1               5

<210> SEQ ID NO 187
<211> LENGTH: 10
<212> TYPE: PRT
<213> ORGANISM: Homo sapiens -continued

```
<400> SEQUENCE: 187

Phe Met Cys Leu Gly Gly Leu Leu Thr Met
1               5                   10

<210> SEQ ID NO 188
<211> LENGTH: 9
<212> TYPE: PRT
<213> ORGANISM: Homo sapiens

<400> SEQUENCE: 188

Met Leu Leu Leu Ile Val Ala Gly Ile
1               5

<210> SEQ ID NO 189
<211> LENGTH: 9
<212> TYPE: PRT
<213> ORGANISM: Homo sapiens

<400> SEQUENCE: 189

Asn Leu Phe Cys Met Leu Leu Leu Ile
1               5

<210> SEQ ID NO 190
<211> LENGTH: 10
<212> TYPE: PRT
<213> ORGANISM: Homo sapiens

<400> SEQUENCE: 190

Leu Leu Ile Val Ala Gly Ile Leu Phe Ile
1               5                   10

<210> SEQ ID NO 191
<211> LENGTH: 10
<212> TYPE: PRT
<213> ORGANISM: Homo sapiens

<400> SEQUENCE: 191

Asn Leu Phe Cys Met Leu Leu Leu Ile Val
1               5                   10

<210> SEQ ID NO 192
<211> LENGTH: 10
<212> TYPE: PRT
<213> ORGANISM: Homo sapiens

<400> SEQUENCE: 192

Met Cys Leu Gly Gly Leu Leu Thr Met Val
1               5                   10

<210> SEQ ID NO 193
<211> LENGTH: 9
<212> TYPE: PRT
<213> ORGANISM: Homo sapiens

<400> SEQUENCE: 193

Leu Ile Val Ala Gly Ile Leu Phe Ile
1               5

<210> SEQ ID NO 194
<211> LENGTH: 9
<212> TYPE: PRT
<213> ORGANISM: Homo sapiens

<400> SEQUENCE: 194
```

-continued

```
Phe Ile Pro Asn Leu Phe Cys Met Leu
1               5

<210> SEQ ID NO 195
<211> LENGTH: 9
<212> TYPE: PRT
<213> ORGANISM: Homo sapiens

<400> SEQUENCE: 195

Ile Val Ala Gly Ile Leu Phe Ile Leu
1               5

<210> SEQ ID NO 196
<211> LENGTH: 10
<212> TYPE: PRT
<213> ORGANISM: Homo sapiens

<400> SEQUENCE: 196

Met Leu Leu Leu Ile Val Ala Gly Ile Leu
1               5               10

<210> SEQ ID NO 197
<211> LENGTH: 10
<212> TYPE: PRT
<213> ORGANISM: Homo sapiens

<400> SEQUENCE: 197

Cys Met Leu Leu Leu Ile Val Ala Gly Ile
1               5               10

<210> SEQ ID NO 198
<211> LENGTH: 10
<212> TYPE: PRT
<213> ORGANISM: Homo sapiens

<400> SEQUENCE: 198

Pro Asn Leu Phe Cys Met Leu Leu Leu Ile
1               5               10

<210> SEQ ID NO 199
<211> LENGTH: 10
<212> TYPE: PRT
<213> ORGANISM: Homo sapiens

<400> SEQUENCE: 199

Phe Ile Pro Asn Leu Phe Cys Met Leu Leu
1               5               10
```

TCR CONSTRUCTS SPECIFIC FOR EBV-DERIVED ANTIGENS

The present invention relates to the filed of immunotherapy, in particular, of Epstein-Barr virus-associated diseases (EBV, also designated Human gammaherpesvirus 4), e.g., cancer or post-transplant lymphoproliferative disease, in particular, to adoptive T cell therapy or T cell receptor (TCR) gene therapy. The invention provides a combination of nucleic acids encoding at least two TCR constructs, or the respective proteins or host cells, wherein each TCR construct is capable of specifically binding to its respective epitope in the context of the respective MHC I, and wherein the epitopes are peptides from different antigens expressed by the same infective agent or cancer, e.g., EBV antigens. The invention also provides specific nucleic acids encoding a TCR alpha chain construct (TRA) and/or a TCR beta chain construct (TRB) of a TCR construct specific for an epitope in complex with a human MHC I, wherein the epitope is an epitope of an Epstein-Barr virus protein, wherein the TCR constructs are specific for epitopes from LMP2A, LMP1 or EBNA3C. Proteins encoded by said nucleic acids, corresponding host cells and pharmaceutical compositions and kits are also objects of the invention.

A TCR is a heterodimeric cell surface protein of the immunoglobulin super-family which is associated with invariant proteins of the CD3 complex involved in mediating signal transduction. TCRs exist in $\alpha\beta$ and $\gamma\delta$ forms, which are structurally similar, but have quite distinct anatomical locations and probably functions. The alpha and beta chains of native heterodimeric $\alpha\beta$TCR are transmembrane proteins, which each comprises two extracellular domains, a membrane-proximal constant domain, and a membrane-distal variable domain. Each of the constant and variable domains includes an intra-chain disulfide bond.

The variable region of each TCR chain comprises variable and joining segments, and in the case of the beta chain also a diversity segment. Each variable region comprises three CDRs (Complementarity Determining Regions), highly polymorphic loops, embedded in a framework sequence, one being the hypervariable region named CDR3. There are several types of alpha chain variable (V$\alpha$) regions and several types of beta chain variable (V$\beta$) regions distinguished by their framework, CDR1 and CDR2 sequences, and by a partly defined CDR3 sequence. Unique TRAV or TRBV numbers are given to V$\alpha$ or V$\beta$s by IMGT nomenclature. TCR specificity for the epitopes recognized is mainly determined by the CDR3 regions (Danska et al., 1990; Garcia et al., 2005.).

The use of adoptive TCR gene therapy allows equipping the patients' own T cells with desired specificities and generation of sufficient numbers of activated, non-exhausted T cells in a short period of time. The TCR may be transduced into all T cells or T-cell subsets such as CD8+ T cells, central memory T cells or T cells with stem cell characteristics, which may ensure better persistence and function upon transfer. TCR-engineered T cells may be infused into patients, e.g., cancer patients that have, e.g., been rendered lymphopenic by chemotherapy or irradiation, inducing homeostatic expansion which greatly enhances engraftment and long term persistence of transferred T cells and is associated with higher cure rates.

TCR-based adoptive T cell therapy relies on classical TCR recognition of processed epitopes of antigens presented in the context of MHC molecules. Thus, a T cell expressing a specific TCR specific for an epitope in the context of a specific MHC can only be used for treatment of a patient expressing the respective MHC.

Epstein-Barr virus (EBV), a human herpesvirus, infects approx. 90% of the world's population. In healthy individuals, diseases caused by EBV are usually cleared by immune cells, wherein T cells play the most important role.

EBV-associated diseases are infectious mononucleosis and various non-malignant, premalignant, and malignant EBV-associated lymphoproliferative diseases such as post transplant lymphoproliferative disorder, Burkitt lymphoma, hemophagocytic lymphohistiocytosis, Hodgkin and non-Hodgkin lymphoma; non-lymphoid malignancies such as gastric cancer, lung cancer, and nasopharyngeal carcinoma; and conditions associated with human immunodeficiency virus such as hairy leukoplakia and central nervous system lymphomas. The virus is also associated with the childhood disorders of Alice in Wonderland Syndrome and acute cerebellar ataxia and, based on some evidence, higher risks of developing certain autoimmune diseases. About 200,000 cancer cases per year are thought to be attributable to EBV (Wikipedia).

Most of the EBV-associated cancers express only a limited number of EBV-specific antigens such as latent membrane proteins (LMP1, LMP2A) and nuclear proteins (EBNA1, EBNA3C). These antigens were shown to be interesting targets for TCR-based immunotherapy, e.g., TCR gene therapy or adoptive T cell therapy of EBV-associated diseases, e.g., post transplant lymphoproliferative disorder or cancer (Orentas et al., 2001; Jurgens et al., 2006; Hart et al., 2008; Simpson et al., 2011; Yang et al., 2011; Zheng et al., 2015; Cho et al., 2018; WO 2015/022520 A1; WO 2011/039508 A2).

However, most T cell-based immunotherapies targeting EBV-associated malignancies have been using natural EBV-specific T cells generated from third party donors or patients, where T cells have been expanded using EBV lymphoblastoid cell lines (LCL) or EBV peptide pools. Adoptive T cell therapies using EBV-specific TCR-engineered T cells have not been tested in clinical trials. TCR-engineered T cells have several advantages compared to natural EBV-specific T cells: 1) Efficacy: The introduced TCR is a pre-defined receptor with high affinity to EBV-positive tumor cells. Growing natural T cells from patient blood relies on the presence of EBV-specific T cells to grow out. However, a patient may lack effective T cells that can be expanded. 2) Feasibility: The success rate of manufacturing engineered T cells is above 95%, while procedures to grow natural T cells have success rates below 70%. 3) Costs: Vein-to-vein time is reduced to less than 21 days in engineered T cell processes compared to more than 40 days for expanding natural T cells.

To execute TCR gene therapy for patient populations with different MHC I (HLA) alleles it is necessary to identify TCRs which are restricted to different HLA alleles. Further, the identification of TCRs which are restricted to different HLA alleles is a pre-requisite for targeting EBV epitopes via two different HLA alleles that are expressed by the same cell.

The present invention addresses some of these problems, and provides novel, and preferably, advantageous immunotherapeutic agents useful for immunotherapy of cancer or infectious agents. This problem is solved by the subject matter of the claims.

Nucleic Acids Encoding TCR Constructs

In one embodiment, the invention provides particular TCR constructs useful for therapy of EBV-associated diseases, and nucleic acids encoding them.

The invention provides a nucleic acid encoding a TCR alpha chain construct (TRA) and/or a TCR beta chain construct (TRB) of a TCR construct specific for an epitope in complex with a human MHC I, wherein the epitope is an epitope of an EBV protein, a) wherein the epitope has the sequence of SEQ ID NO: 1, the MHC I is HLA-A*02:01, and the TRA comprises a CDR3 having at least 90% sequence identity to SEQ ID NO: 13 and the TRB comprises a CDR3 having at least 90% sequence identity to SEQ ID NO: 18;

b) wherein the epitope has the sequence of SEQ ID NO: 2, the MHC I is HLA-B*57:01, and the TRA comprises a CDR3 having at least 90% sequence identity to SEQ ID NO: 23 and the TRB comprises a CDR3 having at least 90% sequence identity to SEQ ID NO: 28;

c) wherein the epitope has the sequence of SEQ ID NO: 3, the MHC I is HLA-C*15:02, and the TRA comprises a CDR3 having at least 90% sequence identity to SEQ ID NO: 33 and the TRB comprises a CDR3 having at least 90% sequence identity to SEQ ID NO: 38;

d) wherein the epitope has the sequence of SEQ ID NO: 4, the MHC I is HLA-C*06:02, and the TRA comprises a CDR3 having at least 90% sequence identity to SEQ ID NO: 43 and the TRB comprises a CDR3 having at least 90% sequence identity to SEQ ID NO: 48;

e) wherein the epitope has the sequence of SEQ ID NO: 5, the MHC I is HLA-B*44:02, and the TRA comprises a CDR3 having at least 90% sequence identity to SEQ ID NO: 53 and the TRB comprises a CDR3 having at least 90% sequence identity to SEQ ID NO: 58;

f) wherein the epitope has the sequence of SEQ ID NO: 5, the MHC I is HLA-B*44:02, and the TRA comprises a CDR3 having at least 90% sequence identity to SEQ ID NO: 63 and the TRB comprises a CDR3 having at least 90% sequence identity to SEQ ID NO: 68;

g) wherein the epitope has the sequence of SEQ ID NO: 6, the MHC I is HLA-B*07:02, and the TRA comprises a CDR3 having at least 90% sequence identity to SEQ ID NO: 73 and the TRB comprises a CDR3 having at least 90% sequence identity to SEQ ID NO: 78; and/or h) wherein the epitope has the sequence of SEQ ID NO: 7, the MHC I is HLA-B*07:02, and the TRA comprises a CDR3 having at least 90% sequence identity to SEQ ID NO: 83 and the TRB comprises a CDR3 having at least 90% sequence identity to SEQ ID NO: 88.

In the context of the present invention, "a" is understood to mean "one or more" unless expressly stated otherwise. Accordingly, for example, if the TCR construct of the invention contains both alpha and beta chain constructs, as preferred throughout the invention, it may be encoded by either one or two nucleic acids. The alpha and beta chain constructs together are capable of specifically binding to an epitope from an EBV protein in complex with a human MHC I. As intermediate products, the alpha and beta chain constructs are also subject matter of the invention by themselves. The invention also provides a single chain nucleic acid construct, wherein, e.g., TCR alpha and beta chain constructs are separated by a P2A element.

One nucleic acid of the invention encodes a TRA and/or a TRB of a TCR construct specific for an epitope in complex with a human MHC I, wherein the epitope has the sequence of SEQ ID NO: 1, the MHC I is HLA-A*02:01, and the TRA comprises a CDR3 having at least 90% sequence identity to SEQ ID NO: 13 and the TRB comprises a CDR3 having at least 90% sequence identity to SEQ ID NO: 18. SEQ ID NO: 1 is an epitope from the EBV protein LMP2A which is known in the art to be presented by cancer cells of an EBV-associated cancer type in the context of HLA-A2, e.g., HLA-A*02:01, i.e., a very common HLA-type (e.g., Orentas et al., 2001, see above). The TCR construct having the CDR3 sequences disclosed herein has a particularly high affinity or peptide sensitivity, as shown herein, compared to a TCR of the art, and thus is a preferred TCR construct of the invention.

Advantageously, said TCR has a high peptide sensitivity with a half maximum IFN-$\gamma$ release with a peptide concentration of $10^{-8}$ mol/L or less, preferably, $10^{-9}$ mol/L or less. The analysis can be carried out by culturing TCR-engineered T cells with target cells (e.g., K562-HLA-A*02:01 cells loaded with peptide, preferably peptide of SEQ ID NO: 1) at an effector to target cell ratio of 1:1, e.g., as described for FIG. 15 or 16, preferably, for FIG. 15.

Optionally, the TRA comprises a CDR1 having at least 80% sequence identity to SEQ ID NO: 11, a CDR2 having at least 80% sequence identity to SEQ ID NO: 12 and a CDR3 having at least 90%, preferably, 100% sequence identity to SEQ ID NO: 13. Optionally, the TRB comprises a CDR1 having at least 80% sequence identity to SEQ ID NO: 16, a CDR2 having at least 80% sequence identity to SEQ ID NO: 17 and a CDR3 having at least 90%, preferably, 100% sequence identity to SEQ ID NO: 18.

The TRA may comprise the junction amino acids shown in SEQ ID NO: 14. The TRB may comprise the junction amino acids shown in SEQ ID NO: 19.

The TRA may comprise a variable region having at least 90%, optionally, at least 95% or 100% sequence identity to SEQ ID NO: 15. The TRB may comprise a variable region having at least 90%, optionally, at least 95% or 100% sequence identity to SEQ ID NO: 20.

A TCR construct comprising a TRA with a variable region of SEQ ID NO: 15 and a TRB with a variable region of SEQ ID NO: 20 has been show to have particularly advantageous characteristics herein. It is also designated TCR06.

The variable region of the TRA of said TCR construct may be encoded by a nucleic acid having a sequence of SEQ ID NO: 91, and the variable region of the TRB of said TCR construct may be encoded by a nucleic acid having a sequence of SEQ ID NO: 92.

One nucleic acid of the invention encodes a TRA and/or a TRB of a TCR construct specific for an epitope in complex with a human MHC I, wherein the epitope has the sequence of SEQ ID NO: 2, the MHC I is HLA-B*57:01, and the TRA comprises a CDR3 having at least 90% sequence identity to SEQ ID NO: 23 and the TRB comprises a CDR3 having at least 90% sequence identity to SEQ ID NO: 28. SEQ ID NO: 2 is an epitope from the EBV protein LMP1 which is presented by cancer cells of an EBV-associated cancer type in the context of HLA-B*57:01. The TCR construct having the CDR3 sequences disclosed herein has a high affinity or peptide sensitivity, as shown herein.

Optionally, said TRA comprises a CDR1 having at least 80% sequence identity to SEQ ID NO: 21, a CDR2 having at least 80% sequence identity to SEQ ID NO: 22 and a CDR3 having at least 90%, preferably, 100% sequence identity to SEQ ID NO: 23. Optionally, said TRB comprises a CDR1 having at least 80% sequence identity to SEQ ID NO: 26, a CDR2 having at least 80% sequence identity to SEQ ID NO: 27 and a CDR3 having at least 90%, preferably, 100% sequence identity to SEQ ID NO: 28.

The TRA may comprise the junction amino acids shown in SEQ ID NO: 24. The TRB may comprise the junction amino acids shown in SEQ ID NO: 29.

The TRA may comprise a variable region having at least 90%, optionally, at least 95% or 100% sequence identity to SEQ ID NO: 25. The TRB may comprise a variable region having at least 90%, optionally, at least 95% or 100% sequence identity to SEQ ID NO: 30.

A TCR construct comprising a TRA with a variable region of SEQ ID NO: 25 and a TRB with a variable region of SEQ ID NO: 30 has been show to have advantageous characteristics herein. It is also designated TCR50.

The variable region of the TRA of said TCR construct may be encoded by a nucleic acid having a sequence of SEQ ID NO: 93, and the variable region of the TRB of said TCR construct may be encoded by a nucleic acid having a sequence of SEQ ID NO: 94.

One nucleic acid of the invention encodes a TRA and/or a TRB of a TCR construct specific for an epitope in complex with a human MHC I, wherein the epitope has the sequence of SEQ ID NO: 3, the MHC I is HLA-C*15:02, and the TRA comprises a CDR3 having at least 90% sequence identity to SEQ ID NO: 33 and the TRB comprises a CDR3 having at least 90% sequence identity to SEQ ID NO: 38. SEQ ID NO: 3 is an epitope from the EBV protein LMP1 which is presently, for the first time, shown to be presented by cancer cells of an EBV-associated cancer type. It is presented in the context of HLA-C*15:02. The TCR construct having the CDR3 sequences disclosed herein has a high affinity or peptide sensitivity, as shown herein.

Optionally, said TRA comprises a CDR1 having at least 80% sequence identity to SEQ ID NO: 31, a CDR2 having at least 80% sequence identity to SEQ ID NO: 32 and a CDR3 having at least 90%, preferably, 100% sequence identity to SEQ ID NO: 33. Optionally, said TRB comprises a CDR1 having at least 80% sequence identity to SEQ ID NO: 36, a CDR2 having at least 80% sequence identity to SEQ ID NO: 37 and a CDR3 having at least 90%, preferably, 100% sequence identity to SEQ ID NO: 38.

The TRA may comprise the junction amino acids shown in SEQ ID NO: 34. The TRB may comprise the junction amino acids shown in SEQ ID NO: 39.

The TRA may comprise a variable region having at least 90%, optionally, at least 95% or 100% sequence identity to SEQ ID NO: 35. The TRB may comprise a variable region having at least 90%, optionally, at least 95% or 100% sequence identity to SEQ ID NO: 40.

A TCR construct comprising a TRA with a variable region of SEQ ID NO: 35 and a TRB with a variable region of SEQ ID NO: 40 has been show to have advantageous characteristics herein. It is also designated TCR83.

The variable region of the TRA of said TCR construct may be encoded by a nucleic acid having a sequence of SEQ ID NO: 95, and the variable region of the TRB of said TCR construct may be encoded by a nucleic acid having a sequence of SEQ ID NO: 96.

One nucleic acid of the invention encodes a TRA and/or a TRB of a TCR construct specific for an epitope in complex with a human MHC I, wherein the epitope has the sequence of SEQ ID NO: 4, the MHC I is HLA-C*06:02, and the TRA comprises a CDR3 having at least 90% sequence identity to SEQ ID NO: 43 and the TRB comprises a CDR3 having at least 90% sequence identity to SEQ ID NO: 48. SEQ ID NO: 4 is an epitope from the EBV protein EBNA3C which is presently, for the first time, shown to be presented by cancer cells of an EBV-associated cancer type. It is presented in the context of HLA-C*06:02.

Optionally, said TRA comprises a CDR1 having at least 80% sequence identity to SEQ ID NO: 41, a CDR2 having at least 80% sequence identity to SEQ ID NO: 42 and a CDR3 having at least 90%, preferably, 100% sequence identity to SEQ ID NO: 43. Optionally, said TRB comprises a CDR1 having at least 80% sequence identity to SEQ ID NO: 46, a CDR2 having at least 80% sequence identity to SEQ ID NO: 47 and a CDR3 having at least 90%, preferably, 100% sequence identity to SEQ ID NO: 48.

The TRA may comprise the junction amino acids shown in SEQ ID NO: 44. The TRB may comprise the junction amino acids shown in SEQ ID NO: 49.

Preferably, the TRA comprises a variable region having at least 90%, optionally, at least 95% or 100% sequence identity to SEQ ID NO: 45. Preferably, the TRB comprises a variable region having at least 90%, optionally, at least 95% or 100% sequence identity to SEQ ID NO: 50.

A TCR construct comprising a TRA with a variable region of SEQ ID NO: 45 and a TRB with a variable region of SEQ ID NO: 50 has been show to have advantageous characteristics herein. It is also designated TCR64.

The variable region of the TRA of said TCR construct may be encoded by a nucleic acid having a sequence of SEQ ID NO: 97, and the variable region of the TRB of said TCR construct may be encoded by a nucleic acid having a sequence of SEQ ID NO: 98.

One nucleic acid of the invention encodes a TRA and/or a TRB of a TCR construct specific for an epitope in complex with a human MHC I, wherein the epitope has the sequence of SEQ ID NO: 5, the MHC I is HLA-B*44:02, and the TRA comprises a CDR3 having at least 90% sequence identity to SEQ ID NO: 53 and the TRB comprises a CDR3 having at least 90% sequence identity to SEQ ID NO: 58. SEQ ID NO: 5 is an epitope from the EBV protein EBNA3C which is presently, for the first time, shown to be presented by cancer cells of an EBV-associated cancer type. It is presented in the context of HLA-B*44:02.

Optionally, said TRA comprises a CDR1 having at least 80% sequence identity to SEQ ID NO: 51, a CDR2 having at least 80% sequence identity to SEQ ID NO: 52 and a CDR3 having at least 90%, preferably, 100% sequence identity to SEQ ID NO: 53. Optionally, said TRB comprises a CDR1 having at least 80% sequence identity to SEQ ID NO: 56, a CDR2 having at least 80% sequence identity to SEQ ID NO: 57 and a CDR3 having at least 90%, preferably, 100% sequence identity to SEQ ID NO: 58.

The TRA may comprise the junction amino acids shown in SEQ ID NO: 54. The TRB may comprise the junction amino acids shown in SEQ ID NO: 59.

Preferably, the TRA comprises a variable region having at least 90%, optionally, at least 95% or 100% sequence identity to SEQ ID NO: 55. Preferably, the TRB comprises a variable region having at least 90%, optionally, at least 95% or 100% sequence identity to SEQ ID NO: 60.

A TCR construct comprising a TRA with a variable region of SEQ ID NO: 55 and a TRB with a variable region of SEQ ID NO: 60 has been show to have advantageous characteristics herein. It is also designated TCR25.

The variable region of the TRA of said TCR construct may be encoded by a nucleic acid having a sequence of SEQ ID NO: 99, and the variable region of the TRB of said TCR construct may be encoded by a nucleic acid having a sequence of SEQ ID NO: 100.

One nucleic acid of the invention encodes a TRA and/or a TRB of a TCR construct specific for an epitope in complex with a human MHC I, wherein the epitope has the sequence of SEQ ID NO: 5, the MHC I is HLA-B*44:02, and the TRA comprises a CDR3 having at least 90% sequence identity to SEQ ID NO: 63 and the TRB comprises a CDR3 having at least 90% sequence identity to SEQ ID NO: 68. As mentioned above, SEQ ID NO: 5 is an epitope from the EBV protein EBNA3C which is presently, for the first time, shown to be presented by cancer cells of an EBV-associated cancer type. It is presented in the context of HLA-B*44:02.

Optionally, said TRA comprises a CDR1 having at least 80% sequence identity to SEQ ID NO: 61, a CDR2 having at least 80% sequence identity to SEQ ID NO: 62 and a CDR3 having at least 90%, preferably, 100% sequence identity to SEQ ID NO: 63. Optionally, said TRB comprises a CDR1 having at least 80% sequence identity to SEQ ID NO: 66, a CDR2 having at least 80% sequence identity to SEQ ID NO: 67 and a CDR3 having at least 90%, preferably, 100% sequence identity to SEQ ID NO: 68.

The TRA may comprise the junction amino acids shown in SEQ ID NO: 64. The TRB may comprise the junction amino acids shown in SEQ ID NO: 69.

Preferably, the TRA comprises a variable region having at least 90%, optionally, at least 95% or 100% sequence identity to SEQ ID NO: 65. Preferably, the TRB comprises a variable region having at least 90%, optionally, at least 95% or 100% sequence identity to SEQ ID NO: 70.

A TCR construct comprising a TRA with a variable region of SEQ ID NO: 65 and a TRB with a variable region of SEQ ID NO: 70 has been show to have advantageous characteristics herein. It is also designated TCR58.

The variable region of the TRA of said TCR construct may be encoded by a nucleic acid having a sequence of SEQ ID NO: 101, and the variable region of the TRB of said TCR construct may be encoded by a nucleic acid having a sequence of SEQ ID NO: 102.

One nucleic acid of the invention encodes a TRA and/or a TRB of a TCR construct specific for an epitope in complex with a human MHC I, wherein the epitope has the sequence of SEQ ID NO: 6, the MHC I is HLA-B*07:02, and the TRA comprises a CDR3 having at least 90% sequence identity to SEQ ID NO: 73 and the TRB comprises a CDR3 having at least 90% sequence identity to SEQ ID NO: 78. SEQ ID NO: 6 is an epitope from the EBV protein EBNA3C which is presented by cancer cells of an EBV-associated cancer type in the context of HLA-B*07:02.

Optionally, said TRA comprises a CDR1 having at least 80% sequence identity to SEQ ID NO: 71, a CDR2 having at least 80% sequence identity to SEQ ID NO: 72 and a CDR3 having at least 90%, preferably, 100% sequence identity to SEQ ID NO: 73. Optionally, said TRB comprises a CDR1 having at least 80% sequence identity to SEQ ID NO: 76, a CDR2 having at least 80% sequence identity to SEQ ID NO: 77 and a CDR3 having at least 90%, preferably, 100% sequence identity to SEQ ID NO: 78.

The TRA may comprise the junction amino acids shown in SEQ ID NO: 74. The TRB may comprise the junction amino acids shown in SEQ ID NO: 79.

Preferably, the TRA comprises a variable region having at least 90%, optionally, at least 95% or 100% sequence identity to SEQ ID NO: 75. Preferably, the TRB comprises a variable region having at least 90%, optionally, at least 95% or 100% sequence identity to SEQ ID NO: 80.

A TCR construct comprising a TRA with a variable region of SEQ ID NO: 75 and a TRB with a variable region of SEQ ID NO: 80 has been show to have advantageous characteristics herein. It is also designated TCR27.

The variable region of the TRA of said TCR construct may be encoded by a nucleic acid having a sequence of SEQ ID NO: 103, and the variable region of the TRB of said TCR construct may be encoded by a nucleic acid having a sequence of SEQ ID NO: 104.

One nucleic acid of the invention encodes a TRA and/or a TRB of a TCR construct specific for an epitope in complex with a human MHC I, wherein the epitope has the sequence of SEQ ID NO: 7, the MHC I is HLA-B*07:02, and the TRA comprises a CDR3 having at least 90% sequence identity to SEQ ID NO: 83 and the TRB comprises a CDR3 having at least 90% sequence identity to SEQ ID NO: 88. SEQ ID NO: 7 is an epitope from the EBV protein EBNA3C, and it comprises SEQ ID NO: 6 and a C-terminal T.

Optionally, said TRA comprises a CDR1 having at least 80% sequence identity to SEQ ID NO: 81, a CDR2 having at least 80% sequence identity to SEQ ID NO: 82 and a CDR3 having at least 90%, preferably, 100% sequence identity to SEQ ID NO: 83. Optionally, said TRB comprises a CDR1 having at least 80% sequence identity to SEQ ID NO: 86, a CDR2 having at least 80% sequence identity to SEQ ID NO: 87 and a CDR3 having at least 90%, preferably, 100% sequence identity to SEQ ID NO: 88.

The TRA may comprise the junction amino acids shown in SEQ ID NO: 84. The TRB may comprise the junction amino acids shown in SEQ ID NO: 89.

Preferably, the TRA comprises a variable region having at least 90%, optionally, at least 95% or 100% sequence identity to SEQ ID NO: 85. Preferably, the TRB comprises a variable region having at least 90%, optionally, at least 95% or 100% sequence identity to SEQ ID NO: 90.

A TCR construct comprising a TRA with a variable region of SEQ ID NO: 85 and a TRB with a variable region of SEQ ID NO: 90 has been show to have advantageous characteristics herein. It is also designated TCR01.

The variable region of the TRA of said TCR construct may be encoded by a nucleic acid having a sequence of SEQ ID NO: 105, and the variable region of the TRB of said TCR construct may be encoded by a nucleic acid having a sequence of SEQ ID NO: 106.

In any of the TRA and/or TRB constructs of the invention, independently, the CDR1 and CDR3 may have at least 80%, at least 90% or 100% sequence identity to the recited sequences. Preferably, the CDR3 has 100% sequence identity to the recited defined CDR3. Typically, if the sequence is not identical, there is at most one amino acid exchange, deletion or insertion, typically, an amino acid exchange. The exchange may be a conserved substitution, i.e., one amino acid of a particular type (e.g., polar, apolar, acidic, basic, aromatic) is exchanged against another amino acid of the same type. Methods for affinity maturation are known in the art and further described below.

Optionally, the sequence identity to the recited CDR1 and CDR2 and CDR3 regions is 100% in the TRA or TRB, preferably, in both TRA and TRB of the TCR constructs of the invention.

A TCR alpha and/or beta chain construct of the invention may comprise all characteristics or domains corresponding to its native counterpart, i.e., a TCR alpha or beta chain, but this is not essential. Preferably, the TCR alpha and/or beta chain construct comprises at least a variable region, or a variable and a constant region, e.g., the variable and/or constant region having at least 60%, at least 70%, at least 80%, at least 90% or at least 95% sequence identity to a human variable or constant TCR region.

The TCR alpha chain constructs and/or the TCR beta chain constructs of the invention preferably comprise a constant region. For adoptive TCR therapy, it is preferred that the TCR construct comprises full length TCR alpha and beta chains comprising variable and constant regions, including transmembrane regions. The constant region may be a human constant region, a murine constant region or a chimeric constant region such as a minimally murine constant region. The TCR construct may be of essentially or exclusively human origin to minimize immunogenicity. To prevent pairing with endogenous TCR chains, the constructs of the invention however preferably contain one or more, e.g., 1-5, 1-10 or 1-20, preferably, 9 amino acid exchanges in comparison to a human sequence (Sommermeyer and Uckert, 2010). To this end, the constant region of the TCR alpha and beta chain construct may also be a murine constant region (Cohen et al., 2006) or/and additional cysteines are provided to enable the formation of an additional disulfide bond between the TCR chains (Cohen et al., 2007, Kuball et al., 2007). In addition, codon modification of the TCR sequence may be used to enhance the functional expression of the transgenic TCR (Scholten et al., 2006) and/or a peptide (e.g. P2A) can be applied to link both TCR chains to achieve a stoichiometric expression of both chains (Leise-gang et al., 2008), also resulting in an enhanced functional expression of the transgenic TCR.

The construct may also be a chimeric antigen receptor, or part of it, wherein, e.g. a human TCR variable region may be linked to a different immunoglobulin constant domain, e.g. an IgG constant domain, or to an antibody domain capable of specifically binding to an antigen such as LMP2A.

Single chain constructs (scTCR) are encompassed as well as heterodimeric TCR constructs. A scTCR can comprise a variable region of a first TCR chain construct (e.g., an alpha chain) and an entire (full-length) second TCR chain (e.g., a beta chain), or vice versa. Furthermore, the scTCR can optionally comprise one or more linkers which join the two or more polypeptides together. The linker can be, for instance, a peptide which joins together two single chains. Also provided is such a scTCR of the invention, which is fused to a cytokine, e.g., a human cytokine, such as IL-2, IL-7, IL-12 or IL-15.

To enable specific recognition of the epitope in the context of the MHC, in partiuclar, for therapeutic purposes, the nucleic acid of the invention encodes one TCR alpha and one beta chain construct of a TCR construct of the invention, e.g., the TCR construct specific for the epitope of SEQ ID NO: 1, as described herein.

Typically, the nucleic acid sequences provided by the invention are codon-optimized for expression in human cells.

In the context of the invention, the nucleic acid can either be DNA or RNA. Preferably, it is DNA. The nucleic acid may, e.g., be a viral vector, or a non-viral vector, e.g., a transposon, a vector suitable for CRISPR/CAS based recombination or a plasmid suitable for in vitro RNA transcription. The nucleic acid of the invention preferably is a vector. Suitable vectors include those designed for propagation and expansion, or for expression or both, such as plasmids and viruses. The vector may be an expression vector suitable for expression in a host cell selected from the group comprising a human T cell or a human T cell precursor, preferably, a human T cell such as CD8+ T cell. Said CD8+ cell may be a central-memory T cell, effector-memory T cell, stem cell-like T cell or effector T cell, or a mixture of these. The vector may be a viral vector, e.g. a retroviral, in particular gamma-retroviral or lentiviral vector. Examples of suitable expression vectors include the retroviral vector MP71 (Engels et al., 2003). The expression vector comprises regulatory sequences, such as transcription and translation initiation and termination codons, which are specific to the type of host cell (e.g., bacterium, fungus, plant, or animal) into which the vector is to be introduced and in which the expression of the nucleic acid of the invention shall be performed, typically, in the context of the invention, human CD8+ T cells. Furthermore, the vector of the invention may include one or more marker genes, which allow for selection of transduced or transfected hosts. The recombinant expression vector can comprise a native or, preferably, a heterologous promoter operably linked to the nucleotide sequence encoding the TCR construct of the invention, or to a nucleotide sequence which is complementary to or which hybridizes to the nucleotide sequence encoding the constructs of the invention. The selection of promoters includes, e.g., strong, weak, inducible, tissue-specific and developmental-specific promoters. The promoter can be a non-viral promoter or a viral promoter. Preferably, it is a heterologous promoter, i.e., a promoter not naturally linked to TCR in human T cells, such as long terminal repeat promoter, which is suitable for expression in human T cells. The inventive recombinant expression vectors can be designed for either transient expression, for stable expression, or for both. Also, the recombinant expression vectors can be made for constitutive expression or for inducible expression.

Proteins

The present invention also provides a protein, i.e., an alpha or beta chain construct, or, preferably, a TCR construct comprising both alpha and beta chain constructs capable of specifically binding an epitope from an EBV-protein described above in the context of the respective MHC I, as described herein, e.g., the TCR construct specific for the epitope of SEQ ID NO: 1, as described herein. The protein is encoded by a nucleic acid of the invention.

The terms "capable of specifically binding" or "recognizing" or "specific for" a given antigen, as used herein, are synonymous, and mean that the TCR construct can specifically bind to and immunologically recognize said epitope, preferably from an EBV protein, more preferably with high affinity. For example, a TCR may be considered to have "be able of specifically binding" to a peptide from an EBV protein if T cells expressing the TCR secrete at least about 200 pg/mL or more (e.g. 250 pg/mL or more, 300 pg/mL or more, 400 pg/mL or more, 500 pg/mL or more, 600 pg/mL or more, 700 pg/mL or more, 1000 pg/mL or more, 2,000 pg/mL or more, 2,500 pg/mL or more, 5,000 pg/mL or more) of interferon $\gamma$ (IFN-$\gamma$) upon co-culture with target cells pulsed with a low concentration of the respective epitope, e.g., about $10^{-11}$ mol/L, $10^{-10}$ mol/L, $10^{-9}$ mol/L, $10^{-8}$ mol/L, $10^{-7}$ mol/L, $10^{-6}$ mol/L, $10^{-5}$ mol/L, but not without epitope or with an unrelated control peptide epitope. Preferably, this is tested with 10,000 TCR+CD8+ T cells and 20,000-50,000, preferably, 50,000 target cells expressing an appropriate HLA, e.g., with an assay as described below in the examples. Alternatively, or additionally, a TCR may be considered to have "antigenic specificity" for an epitope if T cells expressing the TCR secrete at least twice as much IFN-$\gamma$ as the untransduced background level of IFN-$\gamma$ upon co-culture with target cells pulsed with a low concentration of the appropriate peptide. Such "specificity" as described above can—for example—be analyzed with an ELISA.

A high affinity is correlated with a high peptide sensitivity, as described above for the TCR of the invention, e.g., with a half maximum IFN-$\gamma$ release with a peptide concentration of $10^{-6}$ mol/L or less, preferably, $10^{-7}$ mol/L or less, $10^{-8}$ mol/L or less or $10^{-9}$ mol/L or less. Alternatively, affinity can be analyzed by methods well known to the skilled person, e.g. by BiaCore. A TCR affinity or T cell avidity of 100 $\mu$M or higher, more preferably 10 $\mu$M or higher is considered high affinity.

Based on the defined CDR3 and variable region sequences provided by the invention, it is possible to carry out affinity maturation of the TCR sequences (Chervin et al., 2008; Robbins et al., 2008). Non-synonymous nucleotide substitutions, which lead to amino acid exchanges in the CDR3 sequence, may lead to enhanced affinity of the TCR to target antigen. Furthermore, TCR sequence changes in other parts of the variable TRA and TRB regions may change affinity of the TCR to the peptide-MHC I complex. This may increase overall affinity of the TCR to the peptide-MHC, but harbors the risk of unspecific recognition and increased cross-reactivity (Linette et al., 2013). It is preferred that TCRs varying from the specific sequences provided retain exclusive specificity for the target antigen provided, i.e., that they are not cross-reactive, most importantly, that they do not have cross-reactivity for human self-peptides. Potential cross-reactivity of TCR can be tested against known self-peptides loaded on cells with the correct MHC allele (Morgan et al., 2013). Accordingly, it is preferred that adoptive transfer of T cells expressing the TCR construct of the invention has no or significant negative effects on healthy tissue.

The TCR construct according to the invention can also be provided in the form of a multimeric complex, comprising at least two scTCR molecules, wherein said scTCR molecules are each fused to at least one biotin moiety, and wherein said scTCRs are interconnected by biotin-strepavidin interaction to allow the formation of said multimeric complex. Also provided are multimeric complexes of a higher order, comprising more than two, e.g., four, scTCR of the invention.

The TCR construct of the invention can be modified to comprise a detectable label, such as, for instance, a radioisotope, a fluorophore (e.g., fluorescein isothiocyanate (FITC), phycoerythrin (PE)), a tag, such as a HIS-tag, an enzyme (e.g., alkaline phosphatase, horseradish peroxidase), or particles (e.g., gold particles or magnetic particles).

Host Cells

The invention also provides a host cell comprising a nucleic acid and/or protein of the invention. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell or T cell precursor, in particular, a human T cell, which may be isolated from PBMC. The T cell can be any T cell, such as a cultured T cell, e.g. a primary T cell, or a T cell from a cultured T cell line, or a T cell obtained from a mammal, preferably, it is a T cell or T cell precursor from a human patient. The T cell can be obtained from numerous sources, such as blood, bone marrow, lymph node, the thymus, or other tissues or fluids. T cells can also be enriched for or purified. It can be, e.g., a tumor infiltrating cell (TIL), effector cell, central effector cell, memory T cell, naive T cell, and the like, preferably a central-memory T cell. Alternatively, the host cell may be another immune effector cell, e.g., an NK cell or a macrophage.

Preferably, in particular, in the context of therapy of a human, the T cell is a human T cell. The T cell preferably is a CD8+ cell (e.g., cytotoxic T cell). Preferably, the T cell is a T cell isolated from a human, e.g., a human patient, in particular, the patient who is to be treated. Alternatively, the T cell may be from a third-party donor who may be related or unrelated to the patient. Such T cells may be genetically engineered, e.g., in multiple ways. For example, by knock out of the endogenous TCR and/or MHC I. T cells may also be generated from autologous or third-party donor stem cells, wherein, optionally, the stem cells are not human embryonic stem cells.

Preferably, the host cell is a human CD8+ T cell comprising a nucleic acid of the invention which is an expression vector, wherein the nucleic acid encoding the TRA and/or TRB is operably linked to a heterologous promotor, wherein the host cell expresses a TCR construct of the invention.

The invention also provides a host cell expressing two or more different TCR constructs, e.g., two TCR constructs of the invention. Preferably, in this context, the TCR constructs are single chain TCR constructs in which the TCR alpha and beta chains of each TCR are combined by a linker to avoid mispairing between transgenic TCR chains. Said two single chain TCR constructs may be encoded on a single expression vector.

Pharmaceutical Compositions

The invention also provides a pharmaceutical composition comprising a) a nucleic acid of the invention encoding a TCR construct capable of specifically binding to its respective epitope in the context of the respective MHC I; or b) a protein of the invention comprising a TCR construct capable of specifically binding to its respective epitope in the context of the respective MHC I (i.e., a TCR construct of the invention); or c) a host cell of the invention expressing a TCR construct capable of specifically binding to its respective epitope in the context of the respective MHC I.

Preferably, the TCR construct is the TCR construct specific for the epitope of SEQ ID NO: 1.

In another embodiment, the present invention provides a pharmaceutical composition, or a kit comprising at least two pharmaceutical compositions, comprising a) at least two nucleic acids, each encoding a TCR construct capable of specifically binding to its respective epitope in the context of the respective MHC I; or b) at least two proteins, each comprising a TCR construct capable of specifically binding to its respective epitope in the context of the respective MHC I; or c) at least two host cells, each expressing a TCR construct capable of specifically binding to its respective epitope in the context of the respective MHC I, wherein the epitopes are peptides from different antigens expressed by the same cancer or infectious agent. Typically, immunotherapy will be carried out for treatment of a cancer, so the different antigens are preferably antigens expressed by a cancer, i.e., by cells of the same cancer. In this context, antigens are proteins comprising an epitope which may be presented on an MHC I. It is possible that different cancer cells of the same cancer type each express at least one antigen, and the TCR constructs are thus directed to different cancer cells of the same cancer, which may be useful, e.g., if the stage of the cancer is not known and/or if cells of different stages which express different antigens are to be treated. However, generally, it is beneficial if the different antigens are expressed by the same cancer cells.

The inventors have surprisingly found that it is advantageous to use a combination of at least two TCR constructs expressed by T cells for adoptive T cell therapy, in particular, two or more T cells each expressing a TCR construct capable of specifically binding to its respective epitope in the context of the respective MHC I.

Without intending to be bound by the theory, it is believed that attacking the cancer (or infectious agent) based on its expression of two or more antigens can help to sustain the attack and avoid immune evasion, e.g., through mutations, downregulation of one target antigen or antigen loss variants.

It is also possible to target a cancer or infectious agent with three or more TCR constructs, in particular, three or more host cells each comprising a nucleic acid encoding a TCR construct capable of specifically binding to its respective epitope in the context of the respective MHC I, wherein the epitopes are peptides from different antigens expressed by the same cancer or infectious agent.

The kit or pharmaceutical composition is for use in treatment of the cancer or infectious agent from which the epitopes targeted by the TCR constructs are derived.

The infection or cancer may be associated, e.g., with EBV. In this case, the different EBV antigens may be LMP2A, LMP1, EBNA1 or EBNA3C. Preferably, one of the EBV antigens targeted by one TCR construct of the invention is LMP2A. A second EPV antigen targeted by one TCR construct of the invention may be LMP1 or EBN3C, preferably, LMP1. If three EBV antigens are to be targeted, the antigens may be LMP2A, LMP1 and EBNA3C. An alternative or additional EBV antigen is EBNA1.

The present invention also provides a pharmaceutical composition a kit as mentioned above, comprising
a) at least two nucleic acids of the invention, each encoding a TCR construct capable of specifically binding to its respective epitope in the context of the respective MHC I; or
b) at least two proteins of the invention, each comprising a TCR construct capable of specifically binding to its respective epitope in the context of the respective MHC I; or
c) at least two host cells of the invention, each expressing a TCR construct capable of specifically binding to its respective epitope in the context of the respective MHC I;
wherein, optionally, the epitopes are derived from different EBV proteins.

One or two or three TCR constructs used in the context of a pharmaceutical composition or kit of the invention may be TCR constructs of the present invention, as disclosed herein. Preferably, one of the TCR constructs used is the TCR construct disclosed herein recognizing the epitope of SEQ ID NO: 1 in HLA-A2 context.

Accordingly, the kit or pharmaceutical composition may comprise human CD8+ T cells comprising a nucleic acid encoding a TCR construct of the invention, e.g., recognizing the epitope of SEQ ID NO: 1 in HLA-A2 context, as defined herein. The TCR construct may be expressed from the nucleic acid under the control of a heterologous promotor.

In the kit or pharmaceutical composition of the invention comprising at least two nucleic acids encoding TCR constructs, at least two TCR constructs or at least two host cells each comprising a nucleic acid encoding a TCR construct, one, two or three of said TCR constructs may also be other TCR constructs, e.g., TCR constructs known in the art. For example, if the cancer is EBV-associated, one, two or three of the TCR constructs disclosed by Cho et al., 2018; Jurgens et al., 2006; Zheng et al., 2015; Simpson et al., 2011; Yang et al., 2011; Orentase et al., 2001; Hart et al., 2008; WO 2015/022520 A1; or WO 2011/039508 may be used, optionally, in combination with one of the TCR constructs provided herein.

Adoptive T cell therapy (option c) is preferred throughout the present application, wherein the host cell is a T cell, preferably, a human CD8+ T cell. Said host cell typically comprises a nucleic acid encoding the TCR construct under the control of a heterologous promotor.

However, gene therapy with a nucleic acid of the invention (option a) is also possible, wherein, e.g., a lentiviral vector may be used.

A TCR construct of the invention in protein form (option b) may also be used in therapy, e.g., for targeting a toxin to which it is linked to a cancer, for targeting a bacterial minicell to a cancer, which may comprise a therapeutic agent such as a toxin. A TCR construct of the invention in protein form may also be used for targeting a diagnostic agent to a cancer. The composition may thus also be a diagnostic composition.

The T cells each expressing its respective TCR construct may be contained in a kit, wherein, separately, each T cell is stored, e.g., in a pharmaceutically acceptable buffer. The components of a kit of the invention may be formulated for simultaneous administration or for administration in any sequence. The components may also be for repeated administration. Tran et al., 2014 describe a possible regimen of administration. Alternatively, they may be mixed before administration and administered together. Alternatively, the T cells each expressing its respective TCR construct may be contained in a single pharmaceutical composition. The same applies for nucleic acids or proteins of the invention.

The pharmaceutical compositions or kits of the invention typically are for intravenous administration. They may further comprise pharmaceutically acceptable carriers such as buffers, e.g., physiological saline or PBS. They may further comprise excipients, such as stabilizers such as SPGA, carbohydrates (e.g. sorbitol, mannitol, starch, sucrose, glucose, dextran), proteins such as albumin or casein, or protein containing agents such as bovine serum or skimmed milk.

T cells are typically administered to a patient in a concentration of $1\times10^5$-$1\times10^9$ cells per kg. About $1\times10^6$-$1\times10^{11}$ cells may be administered to a patient as a single dose. These parameters may be adapted by the medical practioner, depending, e.g., on the patients age, sex, body weight and medical condition. Protocols disclosed, e.g., in Doran et al., 2019 may be adapted to use the host cells of the present invention.

The pharmaceutical composition of the invention or a kit comprising a pharmaceutical composition or a kit of the invention may be for use in the treatment of a patient expressing an MHC in the context of which the respective TCR recognizes the respective epitope, e.g., as disclosed herein. Average HLA (MHC I) distribution in different populations can be found, e.g., under http://allelefrequencies.net/. It is advantageous to test before treatment if a patient expresses the respective MHC I.

The patient may have a cancer or an infectious disease, in particular in context with the specific TCR constructs disclosed herein, an EBV-associated disease, e.g, selected from the group comprising Hodgkin's and non-Hodgkin lymphoma, Burkitt lymphoma, hemophagocytic lymphohistiocytosis, nasopharyngeal carcinoma, head and neck cancer, gastric cancer, lung cancer hairy leukoplakia, post-transplant lymphoproliferative disorder and central nervous system lymphoma. Preferably, the EBV-associated cancer is a type II malignancy, as exemplified by Hodgkin lymphoma and nasopharyngeal carcinoma, or a type III malignancy, as exemplified by hairy leukoplakia, post transplant lymphoproliferative disorder and central nervous system lymphoma (Orentas et al., 2001), as these cancers typically express high levels of LMP2A and LMP1. In type III malignancies, EBNA2C is additionally expressed.

Targeted cancer cells express the protein or, optionally, the proteins, from which the recognized epitope is derived, preferably, most of the cancer cells.

The patient typically is a mammalian patient. The patient may be a mouse, but, preferably, the patient is a human patient.

The invention also discloses a method of treating cancer or an infectious disease, e.g., an EBV-associated disease, preferably, an EBV-associated cancer, by administering an effective amount of a pharmaceutical composition or kit of the present invention to a patient in need thereof, e.g., a patient having said cancer or disease.

Pharmaceutical compositions and kits of the present invention may be used in combination with other agents, in particular, with other anti-cancer agents. For example, other anti-cancer agents may be TCR-engineered T cells expressing TCRs specific for other antigens expressed in the EBV-positive tumor (e.g. MAGE, NY-ESO, o. a.), checkpoint inhibitors or other immunotherapies as well as antibodies, small molecule inhibitors or other types of reagents.

One preferred medicinal use of the invention is immune therapy, preferably adoptive T cell therapy. The product and methods of the invention are particularly useful in the context of adoptive T cell therapy. The administration of the compounds of the invention can for example involve the administration, e.g., infusion of T cells of the invention into said patient. Preferably such T cells are autologous T cells of the patient which were in vitro transduced with a nucleic acid of the present invention.

Alternatively, the patient may also be administered a nucleic acid of the invention, in particularly, an expression vector, for in vivo transduction of T cells.

Protein TCR constructs of the invention may also, e.g., be used for diagnostic purposes to find out if a subject expresses the respective protein, and, in particular, if the epitope recognized by the TCR construct in the context of the MHC I is presented. To this end, such constructs are preferably labelled to facilitate detection. Preferably, a patient presenting such an epitope on the respective MHC I is treated by an adoptive T cell therapy of the invention.

The invention also relates to a method of preparing a host cell of the invention, comprising introducing an expression vector encoding a TCR construct of the invention into a suitable host cell, preferably, a human CD8+ T cell isolated from a patient.

The present invention is further illustrated in the following examples with reference to the accompanying figures and sequences, nevertheless, without being limited thereto. For the purposes of the present invention, all references as cited herein are incorporated by reference in their entirety.

Vaccines

In one embodiment, the invention provides a pharmaceutical composition, in particular, a vaccine composition, comprising a peptide comprising an epitope capable of being presented by a human MHC I, wherein the epitope is newly identified herein, or a nucleic acid (such as RNA) encoding such a peptide. The epitope may a) have at least 88% sequence identity to SEQ ID NO: 3, wherein the epitope is capable of being presented on HLA-C*15:02, and wherein the peptide comprises at most 25, preferably, at most 11 consecutive amino acids identical to the sequence of amino acids occurring in LMP1 of SEQ ID NO: 120;

b) have at least 88% sequence identity to SEQ ID NO: 4, wherein the epitope is capable of being presented on HLA-C*06:02, and wherein the peptide comprises at most 25, preferably, at most 11 consecutive amino acids identical to the sequence of amino acids occurring in EBNA3C of SEQ ID NO: 121; and c) have at least 90% sequence identity to SEQ ID NO: 5, wherein the epitope is capable of being presented on HLA-B*44:02, and wherein the peptide comprises at most 25, preferably, at most 11 consecutive amino acids identical to the sequence of amino acids occurring in EBNA3C of SEQ ID NO: 121.

Preferably, the peptide of a) can be specifically recognized by TCR83 as defined herein. Preferably, the peptide of b) can be specifically recognized by TCR64 as defined herein. Preferably, the peptide of c) can be specifically recognized by TCR25 or 58 as defined herein.

Peptide vaccinations are well known in the state of the art. For example, peptide vaccines may be for use in administration to a subject in combination with an adjuvant, such as an aluminium salt, e.g., aluminium phosphate or aluminium hydroxide, squalene, e.g., MF59, liposomes, e.g., QS21 or monophosphoryl lipid A.

Such a pharmaceutical composition of the invention may comprise a peptide comprising an epitope of SEQ ID NO: 3, wherein the epitope is capable of being presented on HLA-C*15:02, and wherein the peptide comprises at most 25, at most 15, or preferably, at most 11 amino acids identical to the sequence of amino acids occurring in LMP1 of SEQ ID NO: 120.

Such a pharmaceutical composition of the invention may comprise a peptide comprising an epitope of SEQ ID NO: 2, wherein the epitope is capable of being presented on HLA-B*57:01, and wherein the peptide comprises at most 25, at most 15, or preferably, at most 11 consecutive amino acids identical to the sequence of amino acids occurring in LMP1 of SEQ ID NO: 120.

Such a pharmaceutical composition of the invention may comprise a peptide comprising an epitope of SEQ ID NO: 5, wherein the epitope is capable of being presented on HLA-B*44:02, and wherein the peptide comprises at most 25, at most 15, or preferably, at most 11 consecutive amino acids identical to the sequence of amino acids occurring in EBNA3C of SEQ ID NO: 121.

Nucleic acids encoding a peptide comprising an epitope, as defined herein, may also be used, e.g., in combination with a suitable adjuvant such as liposomes or CpG nucleotides.

Such a pharmaceutical composition of the invention may comprise a nucleic acid encoding a peptide comprising an epitope of SEQ ID NO: 3, wherein the epitope is capable of being presented on HLA-C*15:02, and wherein the peptide comprises at most 25, at most 15, or preferably, at most 11 amino acids identical to the sequence of amino acids occurring in LMP1 of SEQ ID NO: 120.

Such a pharmaceutical composition of the invention may comprise a nucleic acid encoding a peptide comprising an epitope of SEQ ID NO: 4, wherein the epitope is capable of being presented on HLA-C*06:02, and wherein the peptide comprises at most 25, at most 15, or preferably, at most 11 consecutive amino acids identical to the sequence of amino acids occurring in EBNA3C of SEQ ID NO: 121.

Such a pharmaceutical composition of the invention may comprise a nucleic acid encoding a peptide comprising an epitope of SEQ ID NO: 5, wherein the epitope is capable of being presented on HLA-B*44:02, and wherein the peptide comprises at most 25, at most 15, or preferably, at most 11 consecutive amino acids identical to the sequence of amino acids occurring in EBNA3C of SEQ ID NO: 121.

Any of said vaccine pharmaceutical compositions may be for use in vaccination against an EBV-associated disease selected from the group comprising Hodgkin's and non-Hodgkin lymphoma, Burkitt lymphoma, hemophagocytic lymphohistiocytosis, nasopharyngeal carcinoma, head and neck cancer, gastric cancer hairy leukoplakia, post transplant lymphoproliferative disorder and central nervous system lymphoma. The vaccination may be preventive vaccination, i.e., a vaccination provided to a subject not yet having the disease or not yet having an EBV infection, with the intent of reducing the risk for the subject to develop the disease in case of EBV-contact. The subject may belong to a risk group for the disease, e.g., it may be a subject identified as having had EBV contact or as having a correct EBV infection, wherein the subject does not have the disease (yet). Alternatively, the vaccination may be therapeutic vaccination. A patient having an EBV-associated disease may be treated with a therapeutic vaccination.

Advantageously, the HLA of the subject or patient is known, and the vaccine is administered to a patient who is capable of presenting the epitope on an MHC I molecule, e.g., for the epitope as defined in a), a patient who has HLA-C*15, in particular, HLA-C*15:02, for the epitope as defined in b), a patient who has HLA-B*57, in particular HLA-B*57:01, or for the epitope as defined in c), a patient who has HLA-B*44, in particular HLA-B*44:02.

LEGENDS

FIG. 1. Detection of T cell responses using a MHC class I K562 cell library. T cells expanded on EBV antigen-expressing dendritic cells were co-cultured with K562 cells of the MHC cell library. Screening for immunogenic EBV antigen-HLA combinations was performed by (A) analysing the expression of CD137 and (B) determining the amount of secreted IFN-γ by ELISA. (C) FACS sorting of CD137-positive T cells (11%) responding to K562-HLA-B*57:01-positive cells, which then were used to identify dominant TCRα- and TCRβ chains. (MIN—no antigen stimulation, MAX—unspecific antigen stimulation, us—unstained T cells). This approach was applied for the identification and isolation of all further TCRs described herein.

FIG. 2. TCR gene analysis. (A) Next generation sequencing-based TCR repertoire analysis of FACS-sorted T cells responding to EBV antigen-positive (LMP1/LMP2A/EBNA1) K562-HLA-B*57:01 cells. Indicated are parts of total reads assigned to each sequence cluster, which has a sequence representative indicated on the y-axis. TCRα- and TCRβ chains with a frequency of >10% were utilized to construct single chain TCR-retroviruses to identify the functional TCR. (B) For one TCR (designated as TCR50) the different V segments of the most dominant TCRα-(TRAV) and TCRβ (TRBV) chains, their frequency, and the sequences of the CDR-3 region (IMGT nomenclature) are shown (AMSDLYAGNNRKLI: SEQ ID NO: 122, ALT-FLRDDKII: SEQ ID NO: 123, VVMATGFQKLV: SEQ ID NO: 24, ASSQDARVSGANVLT: SEQ ID NO: 124, ASSVTSGSDEQF: SEQ ID NO: 125, ASSFSLGHSYEQY: SEQ ID NO: 126). This approach was applied to all further TCRs described herein.

FIG. 3. Identification of the functional TCRαβ chain combination. TCRα- and TCRβ chains with a frequency of >10% were used to construct single chain TCR-retroviruses for the identification of the functional TCR. For TCR50 TRAV8-2*01 and TRBV9*01 formed a functional TCR as TCR-engineered T cells specifically recognize one antigen (LMP1) in combination with one HLA (B*57:01). Other TCRα- and TCRβ chain combinations resulted in unspecific antigen recognition. The combinatorial approach to identify functional TCRα- and TCRβ chain combinations, as exemplarily shown here for TCR50, was applied to all further TCRs described herein. (MIN—no antigen stimulation, MAX—unspecific stimulation).

Figures 4A, 5A:
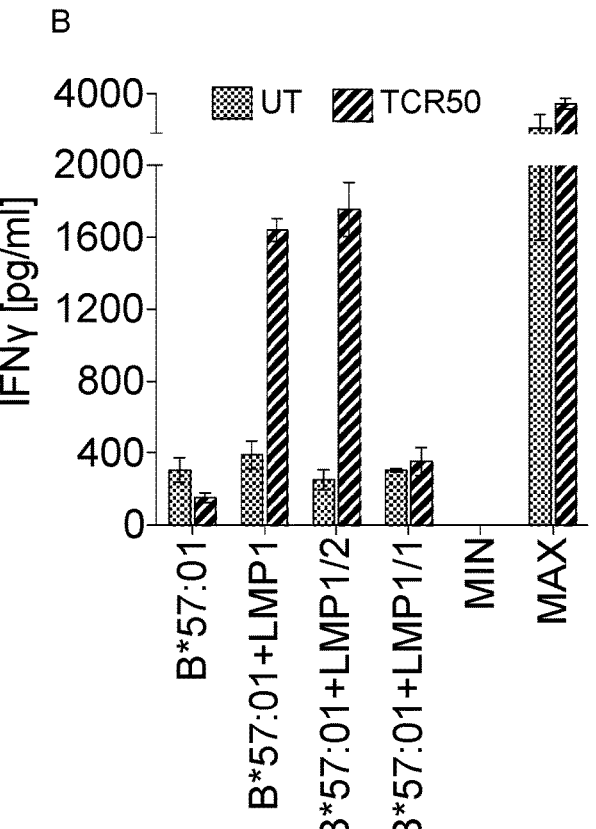

FIG. 4. Epitope mapping to identify the antigenic peptide recognized by TCR50. (A) Truncated versions (LMP1/2, LMP1/1) of the full-length LMP1 antigen were generated and expressed in K562-HLA-B*57:01 cells. (B) The antigen region harboring the immunogenic epitope was identified by measuring the amount of secreted IFN-γ by ELISA in the supernatant and is located between nucleotide (nt) 316 and 624. (MIN—no antigen stimulation, MAX—unspecific antigen stimulation, UT—untransduced T cells).

Figure 5B:
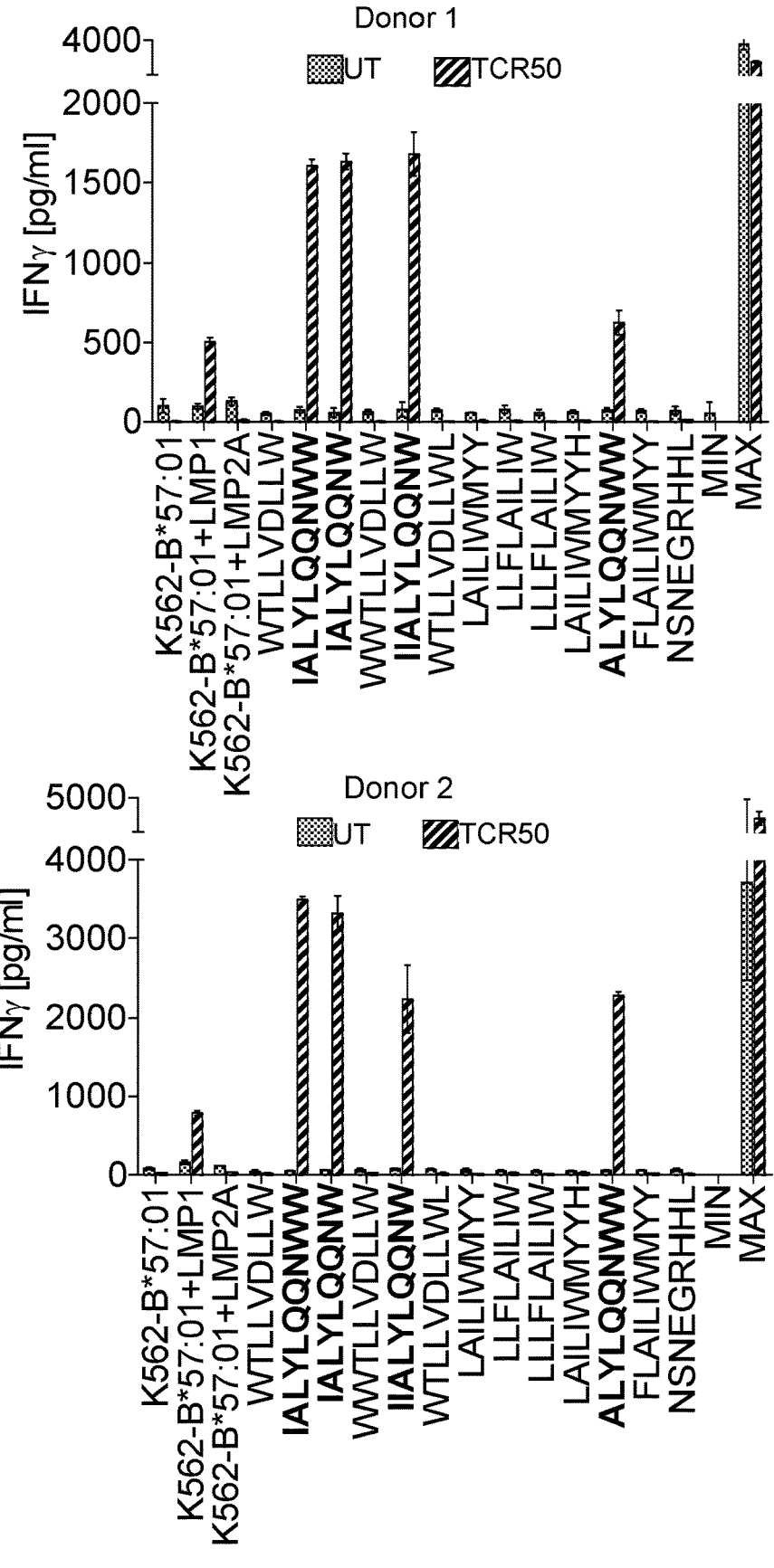

FIG. 5. Identification of the immunogenic epitope of LMP1. The protein region identified as epitope-positive sequence (LMP1/2 nt 316-624) was used to select for candidate peptides applying the epitope prediction algorithm NetMHCpan4.0 for HLA-B*57:01. (A) 13 peptides, according to their peptide-MHC I binding affinity (bind level) classified as strong binder (SB) and weak binder (WB), respectively, were utilized for the identification of the epitope. (B) K562-HLA-B*57:01 cells were loaded with the selected peptides, co-cultured with TCR50-engineered T cells of two donors, and IFN-γ secretion was determined by ELISA. Four epitopes (highlighted in A) with the following amino acid sequences were recognized by TCR50-engineered T cells: IALYLQQNWW (SEQ ID NO: 108), IALYLQQNW (SEQ ID NO: 2), IIALYLQQNW (SEQ ID NO: 110), ALYLQQNWW (SEQ ID NO: 116). SEQ ID NOs of the analyzed peptides are shown in Table 1 below. (MIN—no antigen stimulation, MAX—unspecific stimulation, SB—strong binder, WB—weak binder, UT—untransduced T cells).

Figure 6:
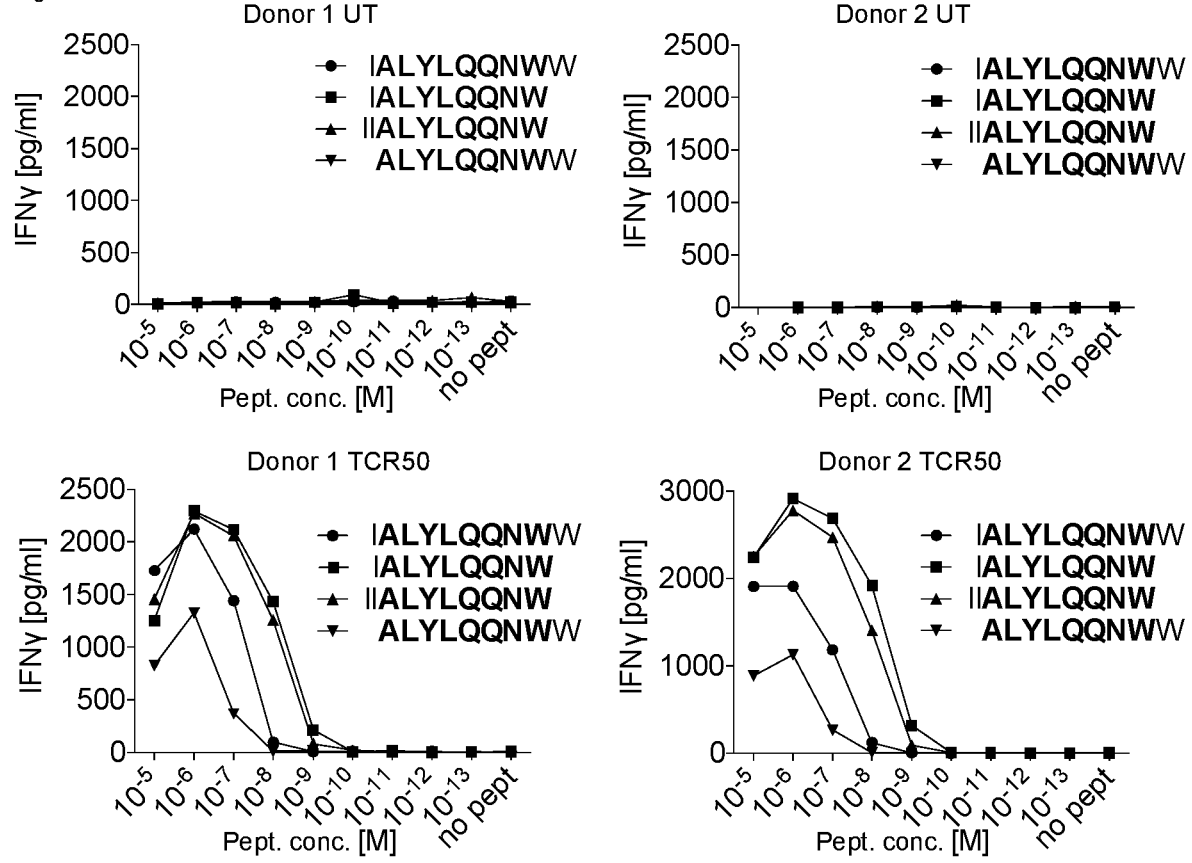

FIG. 6. Peptide titration of TCR50-engineered T cells. Untransduced (UT) and TCR50-transduced T cells (TCR50) of two donors were co-cultured with K562-HLA-B*57:01 cells loaded with titrated amounts of the indicated peptides (SEQ ID NO: 2, 108, 110, 116) and the amount of secreted IFN-γ in the supernatant was determined by ELISA. Peptide IALYLQQNW (9mer, SEQ ID NO: 2), was recognized at lowest concentrations and can therefore be considered as cognate EBV LMP1 epitope of TCR50. Interestingly and worth to mentioning, this epitope recognized by TCR50 was not ranked highest in the NetMHCpan4.0 prediction tool indicating that the prediction tool is not precise in forecasting relevant immunodominant epitopes.

FIG. 7. TCR50-engineered T cells recognize LMP1-positive cells. Functional analysis of LMP1-specific TCR50-engineered T cells of two donors using K562-HLA-B*57:01 antigen-loaded cells, an EBV-associated cancer cell line (L591-B*57:01), and lymphoblastoid cell lines (WIN, DEM), respectively. T cell reactivity was determined by measuring the amount of secreted IFN-γ by ELISA at an effector to target (E:T) cell ratio of 1:1. (MIN—no antigen stimulation, MAX—unspecific stimulation, UT—untransduced T cells).

FIG. 8. Functional analysis of the EBNA3C-reactive TCR01. (A) EBNA3C-specific TCR01-engineered T cells were co-cultured with K562-HLA-B*07:02 antigen-pulsed cells and EBV-positive cell lines. T cell functionality was determined by measuring the amount of secreted IFN-γ by ELISA at at an effector to target (E:T) cell ratio of 1:1. (B) Truncated versions (EBNA3C/3, EBNA3C/2, EBNA3C/1) of the full-length EBNA3C antigen were generated and expressed in K562-HLA-B*07:02 cells. (C) The antigen region harboring the immunogenic epitope was identified by measuring the amount of secreted IFN-γ by ELISA in the supernatant and is located between nucleotide (nt) 2071 and 2979. (D) The protein region identified as epitope-positive sequence (EBNA3C nt 2071-2979) was used to select for candidate peptides applying the epitope prediction algorithm NetMHCpan4.0 for HLA-B*07:02. (E) 27 peptides according to their peptide-MHC I binding affinity (bind level) classified as strong binder (SB) and weak binder (WB), respectively, were utilized for the identification of the epitope (QPRAPIRPI (SEQ ID NO: 127), RPIPTRFPPPPM (SEQ ID NO: 128), RPRVEESSHGPA (SEQ ID NO: 129), SPQPRAPI (SEQ ID NO: 130), SPQPRAPIRPI (SEQ ID NO: 131), SPQPRAPIRPIP (SEQ ID NO: 132), PQPRA-PIRPI (SEQ ID NO: 133), QPRAPIRPIP (SEQ ID NO: 134), PRAPIRPI (SEQ ID NO: 135), APIRPIPTRF (SEQ ID NO: 136), FPPPPMPL (SEQ ID NO: 137), HGPARCSQAT (SEQ ID NO: 138), RPIPTRFPP (SEQ ID NO: 139), RPIP-TRFP (SEQ ID NO: 140), IPTRFPPPPMP (SEQ ID NO: 141), PIPTRFPPPPM (SEQ ID NO: 142), IPTRFPPPPMPL (SEQ ID NO: 143), GPARCSQATA (SEQ ID NO: 144), FPPPPMPLQDSM (SEQ ID NO: 145), PPMPLQDSM (SEQ ID NO: 146), RPIPTRFPPP (SEQ ID NO: 147), MPLQDSMAVG (SEQ ID NO: 148), PIPTRFPPPPMP (SEQ ID NO: 149), PMPLQDSMAV (SEQ ID NO: 150), PMPLQDSM (SEQ ID NO: 151), QPRAPIRPIPT (SEQ ID NO: 152), QPRAPIRP (SEQ ID NO: 153)). K562-HLA-B*07:02 cells were loaded with the selected peptides, co-cultured with TCR01-engineered T cells, and IFN-γ secretion was determined by ELISA. Epitopes (highlighted in D) were recognized by TCR01-engineered T cells. (F) K562-HLA-B*07:02 cells were loaded with titrated amounts of the indicated peptides or no peptide as control and peptide sensitivity of TCR01-engineered T cells was determined by measuring the amount of secreted IFN-γ by ELISA at an E:T cell ratio of 1:1. (MIN—no antigen stimulation, MAX—unspecific stimulation, SB—strong binder, WB—weak binder, UT—untransduced T cells).

FIG. 9. Functional analysis of the EBNA3C-reactive TCR25. (A) EBNA3C-specific TCR25-engineered T cells were co-cultured with K562-HLA-B*44:02 antigen-pulsed cells or an EBV-associated cancer cell line. T cell functionality was determined by measuring the amount of secreted IFN-γ by ELISA at an effector to target (E:T) cell ratio of 1:1. (B) Truncated versions (EBNA3C/3, EBNA3C/2, EBNA3C/1) of the full-length EBNA3C antigen were generated and expressed in K562-HLA-B*44:02 cells. (C) The antigen region harboring the immunogenic epitope was identified by measuring the amount of secreted IFN-γ by ELISA in the supernatant and is located between nucleotide (nt) 1 and 567. (D) The protein region identified as epitope-positive sequence (EBNA3C nt 1-567) was used to select for candidate peptides applying the epitope prediction algorithm NetMHCpan4.0 for HLA-B*44:02. (E) Four peptides according to their peptide-MHC binding affinity (bind level) classified as strong binder (SB) and weak binder (WB), respectively, were utilized for the identification of the epitope (AEGGVGWRHW (SEQ ID NO: 5), SER-LVPEESY (SEQ ID NO: 155), WLLTSPSQSW (SEQ ID NO: 156), LLTSPSQSW (SEQ ID NO: 157)). K562-HLA-B*44:02 cells were loaded with the selected peptides, co-cultured with TCR25-engineered T cells, and IFN-γ secretion was determined by ELISA. One epitope (highlighted in D) with the amino acid sequence AEGGVGWRHW was recognized by TCR25-engineered T cells and can therefore be considered as cognate EBV EBNA3C epitope of TCR25. (F) K562-HLA-B*44:02 cells were loaded with titrated amounts of the indicated peptide or no peptide as control. Peptide sensitivity of TCR25-engineered T cells was determined by measuring the amount of secreted IFN-γ by ELISA at an E:T cell ratio of 1:1. (MIN—no antigen stimulation, MAX—unspecific stimulation, SB—strong binder, WB—weak binder, UT—untransduced T cells).

FIG. 10. Functional analysis of the EBNA3C-reactive TCR27. (A) EBNA3C-specific TCR27-engineered T cells were co-cultured with K562-HLA-B*07:02 antigen-pulsed cells and EBV-positive cell lines. T cell functionality was determined by measuring the amount of secreted IFN-γ by ELISA at an effector to target (E:T) cell ratio of 1:1. (B) Truncated versions (EBNA3C/3, EBNA3C/2, EBNA3C/1) of the full-length EBNA3C antigen were generated and expressed in K562-HLA-B*07:02 cells. (C) The antigen region harboring the immunogenic epitope was identified by measuring the amount of secreted IFN-γ (ELISA) in the supernatant and is located between nucleotide (nt) 2071 and 2979. (D) The protein region identified as epitope-positive sequence (EBNA3C nt 2071-2979) was used to select for candidate peptides applying the epitope prediction algorithm NetMHCpan4.0 for HLA-B*07:02. (E) 27 peptides according to their peptide-MHC binding affinity (bind level) classified as strong binder (SB) and weak binder (WB), respectively, were utilized for the identification of the epitope. K562-HLA-B*07:02 cells were loaded with the selected peptides, co-cultured with TCR27-engineered T cells, and IFN-γ secretion was determined by ELISA. Epitopes (highlighted in D) were recognized by TCR27-engineered T cells. (F) K562-HLA-B*07:02 cells were loaded with titrated amounts of the indicated peptides or no peptide as control and peptide sensitivity of TCR27-engineered T cells was determined by measuring the amount of secreted IFN-γ by ELISA at an E:T cell ratio of 1:1. (MIN—no antigen stimulation, MAX—unspecific stimulation, SB—strong binder, WB—weak binder, UT—untransduced T cells, SEQ ID NOs cf. legend to FIG. 8).

FIG. 11. Functional analysis of the EBNA3C-reactive TCR58. (A) EBNA3C-specific TCR58-engineered T cells were co-cultured with K562-HLA-B*44:02 antigen-pulsed cells or an EBV-associated cancer cell line. T cell functionality was determined by measuring the amount of secreted IFN-γ by ELISA at an effector to target (E:T) cell ratio of 1:1. (B) Truncated versions (EBNA3C/3, EBNA3C/2, EBNA3C/1) of the full-length EBNA3C antigen were generated and expressed in K562-HLA-B*44:02 cells. (C) The antigen region harboring the immunogenic epitope was identified by measuring the amount of secreted IFN-γ by ELISA in the supernatant and is located between nucleotide (nt) 1 and 567. (D) The protein region identified as epitope-positive sequence (EBNA3C nt 1-567) was used to select for candidate peptides applying the epitope prediction algorithm NetMHCpan4.0 for HLA-B*44:02. (E) Four peptides according to their peptide-MHC binding affinity (bind level) classified as strong binder (SB) and weak binder (WB), respectively, were utilized for the identification of the epitope. K562-HLA-B*44:02 cells were loaded with the selected peptides, co-cultured with TCR58-engineered T cells, and IFN-γ secretion was determined by ELISA. One epitope (highlighted in D) with the amino acid sequence AEGGVGWRHW was recognized by TCR58-engineered T cells and can therefore be considered as cognate EBV EBNA3C epitope of TCR58. (F) K562-HLA-B*44:02 cells were loaded with titrated amounts of the indicated peptide or no peptide as control. Peptide sensitivity of TCR58-engineered T cells was determined by measuring the amount of secreted IFN-γ by ELISA at an E:T cell ratio of 1:1. (MIN—no antigen stimulation, MAX—unspecific stimulation, SB—strong binder, WB—weak binder, UT—untransduced T cells, SEQ ID NOs cf. legend to FIG. 9).

FIG. 12. Functional analysis of the EBNA3C-reactive TCR64. (A) EBNA3C-specific TCR64-engineered T cells were co-cultured with K562-HLA-C*06:02 antigen-pulsed cells and EBV-positive cell lines. T cell functionality was determined by measuring the amount of secreted IFN-γ by ELISA at an effector to target (E:T) cell ratio of 1:1. (B) Truncated versions (EBNA3C/3, EBNA3C/2, EBNA3C/1) of the full-length EBNA3C antigen were generated and expressed in K562-HLA-C*06:02 cells. (C) The antigen region harboring the immunogenic epitope was identified by measuring the amount of secreted IFN-γ by ELISA in the supernatant and is located between nucleotide (nt) 568 and 1569. (D) The protein region identified as epitope-positive sequence (EBNA3C nt 568-1569) was used to select for candidate peptides applying the epitope prediction algorithm NetMHCpan4.0 for HLA-C*06:02. (E) 27 peptides according to their peptide-MHC binding affinity (bind level) classified as strong binder (SB) and weak binder (WB), respectively, were utilized for the identification of the epitope (RRYRRIYDL (SEQ ID NO: 158), FRKAQIQGL (SEQ ID NO: 4), AREAEVRFL (SEQ ID NO: 159), LRGKWQRRY (SEQ ID NO: 160), ERYAREAEV (SEQ ID NO: 161), SRRRRGACV (SEQ ID NO: 162), NLLDFVRFM (SEQ ID NO: 163), RRIYDLIEL (SEQ ID NO: 164), RRRRGACW (SEQ ID NO: 165), VRFLRGKWQ (SEQ ID NO: 166), RRRGACVVY (SEQ ID NO: 167), QRRYRRIYD (SEQ ID NO: 168), VRFMGVMSS (SEQ ID NO: 169), YAREAEVRFL (SEQ ID NO: 170), NRVGADSIM (SEQ ID NO: 171), LHHIWQNLL (SEQ ID NO: 172), RRGIKEHVI (SEQ ID NO: 173), YRRIYDLIE (SEQ ID NO: 174), RRYRRIYDLI (SEQ ID NO: 175), ARRGIKEHV (SEQ ID NO: 176), QRRYRRIYDL (SEQ ID NO: 177), WQRRYRRIY (SEQ ID NO: 178), FLRGKWQRRY (SEQ ID NO: 179), RRGACWYD (SEQ ID NO: 180), VYDDDVIEV (SEQ ID NO: 181), YAREAEVRF (SEQ ID NO: 182), GCQNAARTL (SEQ ID NO: 183)). K562-HLA-C*06:02 cells were loaded with the selected peptides, co-cultured with TCR64-engineered T cells, and IFN-γ secretion was determined by ELISA. One epitope (highlighted in D) with the amino acid sequence FRKAQIQGLwas recognized by TCR64-engineered T cells and can therefore be considered as cognate EBV EBNA3C epitope of TCR64. (F) K562-HLA-C*06:02 cells were loaded with titrated amounts of the indicated peptide or no peptide as control and peptide sensitivity of TCR64-engineered T cells was determined by measuring the amount of secreted IFN-γ by ELISA at an E:T cell ratio of 1:1. (MIN—no antigen stimulation, MAX—unspecific stimulation, SB—strong binder, WB—weak binder, UT—untransduced T cells).

FIG. 13. Functional analysis of the LMP1-reactive TCR83. (A) LMP1-specific TCR83-engineered T cells were co-cultured with K562-HLA-C*15:02 antigen-pulsed cells or an EBV-associated cancer cell line. T cell functionality was determined by measuring the amount of secreted IFN-γ by ELISA at an effector to target (E:T) cell ratio of 1:1. (B) Truncated versions (LMP1/2, LMP1/1) of the full-length LMP1 antigen were generated and expressed in K562-HLA-C*15:02 cells. (C) The antigen region harboring the immunogenic epitope was identified by measuring the amount of secreted IFN-γ by ELISA in the supernatant and is located between nucleotide (nt) 316 and 624. (D) The protein region identified as epitope-positive sequence (LMP1 nt 316-624) was used to select for candidate peptides applying the epitope prediction algorithm NetMHCpan4.0 for HLA-C*15:02. (E) Four peptides according to their peptide-MHC binding affinity (bind level) classified as weak binder (WB) were utilized for the identification of the epitope (NSNE-GRHHL (SEQ ID NO: 184), QQNWWTLLV (SEQ ID NO: 3), DSLPHPQQA (SEQ ID NO: 185), YLQQNWWTL (SEQ ID NO: 186)). K562-HLA-C*15:02 cells were loaded with the selected peptides, co-cultured with TCR83-engineered T cells, and IFN-γ secretion was determined by ELISA. One epitope (highlighted in D) with the amino acid sequence QQNWWTLLV was recognized by TCR83-engineered T cells and can therefore be considered as cognate EBV LMP1 epitope of TCR83. (F) K562-HLA-C*15:02 cells were loaded with titrated amounts of the indicated peptide or no peptide as control. Peptide sensitivity of TCR83-engineered T cells was determined by measuring the amount of secreted IFN-γ by ELISA at an E:T cell ratio of 1:1 (B). (MIN—no antigen stimulation, MAX—unspecific stimulation, WB—weak binder, UT—untransduced T cells).

FIG. 14. Functional analysis of the LMP2A-reactive TCR06. (A) LMP2A-specific TCR06-engineered T cells were co-cultured with K562-HLA-A*02:01 antigen-pulsed cells or EBV-associated cancer cell lines. T cell functionality was determined by measuring the amount of secreted IFN-γ by ELISA at an effector to target (E:T) cell ratio of 1:1. (B) Truncated versions (LMP2A/2, LMP2A/1) of the full-length LMP2A antigen were generated and expressed in K562-HLA-A*02:01 cells. (C) The antigen region harboring the immunogenic epitope was identified by measuring the amount of secreted IFN-γ (ELISA) in the supernatant and is located between nucleotide (nt) 1006 and 1494. (D) The protein region identified as epitope-positive sequence (LMP1 nt 1006-1494) was used to select for candidate peptides applying the epitope prediction algorithm NetMHCpan4.0 for HLA-A*02:01. (E) 14 peptides according to their peptide-MHC binding affinity (bind level) classified as strong binder (SB) and weak binder (WB), respectively, were utilized for the identification of the epitope (FMCLGGLLTM (SEQ ID NO: 187), MLLLIVAGI (SEQ ID NO: 188), NLFCMLLLI (SEQ ID NO: 189), LLIVAGILFI (SEQ ID NO: 190), NLFCMLLLIV (SEQ ID NO: 191), MCLGGLLTMV (SEQ ID NO: 192), CLG-GLLTMV (SEQ ID NO: 1), LIVAGILFI (SEQ ID NO: 193), FIPNLFCML (SEQ ID NO: 194), IVAGILFIL (SEQ ID NO: 195), MLLLIVAGIL (SEQ ID NO: 196), CMLLLIVAGI (SEQ ID NO: 197), PNLFCMLLLI (SEQ ID NO: 198), FIPNLFCMLL (SEQ ID NO: 199)). K562-HLA-A*02:01 cells were loaded with the selected peptides, co-cultured with TCR06-engineered T cells, and IFN-γ secretion was determined by ELISA. Epitopes (highlighted in D) were recognized by TCR06-engineered T cells and can therefore be considered as cognate EBV LMP2A epitopes of TCR06. Interestingly and worth to mentioning, that the two epitopes recognized by TCR06 were not ranked highest in the NetMHCpan4.0 prediction tool indicating that the prediction tool is not precise in forecasting relevant immunodominant epitopes. (F) K562-HLA-A*02:01 cells were loaded with titrated amounts of the indicated peptides or no peptide as control. Peptide sensitivity of TCR06-engineered T cells was determined by measuring the amount of secreted IFN-γ by ELISA at an E:T cell ratio of 1:1(B). (MIN—no antigen stimulation, MAX—unspecific stimulation, S—strong binder, WB—weak binder, UT—untransduced T cells).

FIG. 15. Comparison of peptide sensitivity of LMP2A-specific TCR06 and TCRs provided in patents WO 2015/022520 A1 (PUBTCR1) and WO 2011/039508 A2 (PUBTCR2). The previously published wt EBV LMP2A TCR with a TRAV12-3*01/TRAJ41*01/TRAC alpha chain amino acid sequence (SEQ ID No: 2 of WO 2015/022520

A1) and a TRBV11-2*01/TRBD1/TRBJ2-7/TRBC beta chain amino acid sequence (SEQ ID No: 3 of WO 2015/022520 A1), also FIG. 1 of said document, is herein designated PUBTCR1. The previously published LMP2A TCR described in WO 2011/039508 A2, in particular, based on SEQ ID NO: 8 thereof, is designated PUBTCR2. K562-HLA-A*02:01 cells were loaded with titrated amounts of the indicated peptides CLGGLLTMV and MCLGGLLTMV, respectively, co-cultured with TCR06- or PUBTCR1- or PUBTCR2-engineered T cells, and peptide sensitivity of all TCRs was determined by measuring the amount of secreted IFN-γ by ELISA at an effector to target (E:T) cell ratio of 1:1. TCR06 has a higher peptide sensitivity in comparison to PUBTCR1 and PUBTCR2. UT—untransduced T cells.

Figure 16:
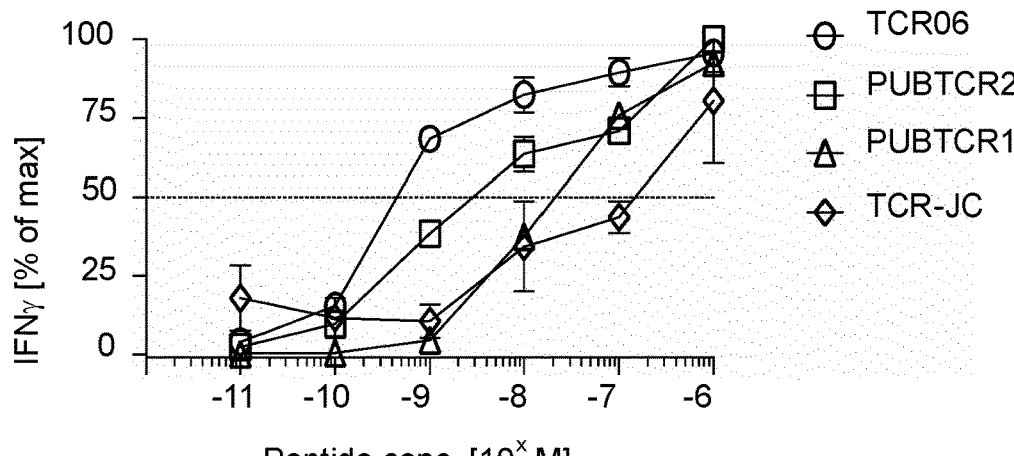

FIG. 16. Extended comparison of peptide sensitivity of LMP2A-specific TCR06 with TCRs provided in patents WO 2015/022520 A1 (PUBTCR1) and WO 2011/039508 A2 (PUBTCR2) and TCR-JC isolated by the applicants.

The previously published wt EBV LMP2A TCR with a TRAV12-3*01/TRAJ41*01/TRAC alpha chain amino acid sequence (SEQ ID NO: 2 of WO 2015/022520 A1) and a TRBV11-2*01/TRBD1/TRBJ2-7/TRBC beta chain amino acid sequence (SEQ ID NO: 3 of WO 2015/022520 A1), also FIG. 1 of said document, is herein designated PUBTCR1. The previously published LMP2A TCR described in WO 2011/039508 A2, in particular, based on SEQ ID NO: 8 thereof, is designated PUBTCR2. Another LMP2A-specific TCR, herein designated as TCR-JC, was isolated by the applicants. (A) K562-HLA-A*02:01 cells were loaded with titrated amounts of the peptide CLGGLLTMV, co-cultured with TCR06-, PUBTCR1-, PUBTCR2- or TCR-JC-engineered T cells, and peptide sensitivity of all TCRs was determined by measuring the amount of secreted IFN-γ by ELISA at an effector to target (E:T) cell ratio of 1:10. (B) Sigmoidal 4PL curves (constrained model) based on data points from A. The sigmoidal regression shows a very good $R^2$ (approx. 0.95) for TCR06, PUBTCR1, and PUBTCR2. Data from TCR-JC shows a model fit of 0.81 (lack of upper plateau). (C) Based on data shown in B, the peptide sensitivity of the four TCRs was calculated and indicated as EC50 in $10^{-9}$ M (EC50—mol/l of peptide needed to achieve 50% of the maximal IFN-γ release, SEM—standard error mean).

FIG. 17. EBV-specific TCR-engineered T cells kill cancer cells. LMP1-specific TCR50-, LMP2A-specific TCR06-, and EBNA3C-specific TCR64-engineered T cells were co-cultured with L591 EBV$^+$ tumor cells, which naturally express LMP1, LMP2A, and EBNA3C but were transfected with the respective MHC I allele. At indicated effector:target (E:T) cell ratios, data of triplicate wells were averaged and the percentage of surviving cells was calculated in relation to the values obtained from the samples co-cultured with untransduced T cells: % specific survival=100×(test value)/(average background). (UT—untransduced T cells).

FIG. 18. In vivo mouse models of tumor rejection (A) NOG mice received subcutaneously $5×10^6$ K562-HLA-A*02:01 tumor cells and 24 h later intravenously $1×10^7$ TCR06-engineered T cells. Data obtained from individual mice receiving TCR06-engineered T cells (n=10) from two donors are shown in comparison to untransduced T cells (n=6). (B) NSG mice received subcutaneously $5×10^6$ K562-HLA-B*57:01 tumor cells and nine days later intravenously $5×10^6$ TCR50-engineered T cells. In both models, tumor size was measured using a caliper and calculated.

EXAMPLES

Generation of EBV-Specific TCR Constructs and Transgenic T Cells and Identification of Epitopes The inventors used an innovative method (Lorenz et al., 2018; WO2016/146618 A1) to generate EBV-specific TCRs, which recognize endogenously processed, immunogenic EBV epitopes presented by different MHC class I molecules.

Briefly, after selecting the EBV antigen of interest, e.g., LMP1, LMP2A or EBNA3C, the following experimental steps were performed:

(i) Pulsing of professional antigen-presenting cells (preferably dendritic cells (DCs)) with in vitro-transcribed (ivt) RNA encoding the full-length sequence of the selected EBV antigen to stimulate autologous T cells. This procedure is completely unbiased and allows the DCs to select the best epitope of the antigen for expression, processing, and presentation on the cell surface in conjunction with the most suitable MHC class I (MHC I) molecule.

(ii) Identification of EBV antigen-reactive T cells. This step was performed by means of a newly established MHC class I cell library, which is composed of single MHC I-expressing cell lines originated from K562 cells. This part is an important feature of the TCR isolation approach, because it is basic to take advantage of the broad MHC flexibility. For the identification of each TCR, the inventors selected up to six MHC I from the K562 cell library that correspond to MHC I alleles of the T cell donor, and transfected the cells with the relevant antigens used for priming in step (i). After co-culture of antigen-presenting K562 cells and antigen-stimulated T cells, responding T cells were identified by interferon-(IFN)γ release using an ELISA, and up-regulation of the T cell activation marker CD137 measured by flow cytometry. Subsequently, reactive CD8+ T cells were enriched by FACS sorting.

(iii) Isolation of total RNA from FACS-sorted CD8+ T cells and PCR amplification of TCRα- and TCRβ chain-specific sequences. Identification of dominant TCRα- and TCRβ sequences by next generation sequencing.

(iv) Re-expression of dominant (at least 10%) TCRα- and TCRβ chain combinations using the γ-retrovirus vector MP71 (Engels et al., 2003; Leisegang et al., 2008; Sommermeyer and Uckert, 2010) in primary human T cells to identify the functional TCRαβ chain combination. This was done by co-cultivation of TCR-engineered T cells with K562 cells carrying the proper MHC I molecule and expressing the full-length EBV antigen. Antigen recognizing TCRαβ chain combinations were linked with a P2A element and recloned in the configuration of TCRβ gene-P2A-TCRα gene into the MP71 vector. Constant TCRαβ chain regions were replaced by their murine counterparts to enhance pairing of transgenic TCR chains. Subsequently, the complete TCR transgene cassette was codon optimized.

(v) Identification of the antigenic peptide (epitope) of EBV, which is recognized by the TCR-engineered T cells. For this, the full-length antigen was C- or N-terminally truncated, cloned into the plasmid vector pcDNA3.1(−) and expressed in K562 cells carrying the proper MHC I molecule. Then, the remaining protein fragments were tested for their ability to furthermore present the epitope recognized by the TCR. Finally, candidate peptides of the corresponding protein region were identified by the epitope prediction algorithm NetMHCpan4.0 (http://www.cbs.dtu.dk/services/NetMHCpan/). Predicted peptides were generated and loaded onto K562 cells carrying the proper MHC I molecule and investigated in co-culture experiments for their ability to be recognized by TCR-engineered T cells. The peptides capable of stimulating most IFN-γ production are considered as cognate epitope.

TABLE 1

Peptides tested for one of the TCR (TCR50). The protein region identified as epitope-positive sequence (LMP1/2 nt 316-624) was used to select for candidate peptides applying the epitope prediction algorithm NetMHCpan4.0 for HLA-B*57:01. 13 peptides, according to their peptide-MHC binding affinity classified as strong binder (SB) and weak binder (WK), respectively, were utilized for epitope identification. Results are shown in FIG. 5.

| Epitope (SEQ ID NO:) | Length (aa) | Bind level | Affinity |
|---|---|---|---|
| WTLLVDLLW (107) | 9 | SB | 12.25 |
| IALYLQQNWW (108) | 10 | SB | 14.84 |
| IALYLQQNW (2) | 9 | SB | 16.32 |
| WWTLLVDLLW (109) | 10 | SB | 32.51 |
| IIALYLQQNW (110) | 10 | SB | 57.84 |
| WTLLVDLLWL (111) | 10 | SB | 111.95 |
| LAILIWMYY (112) | 9 | SB | 231.02 |
| LLFLAILIW (113) | 9 | SB | 234.00 |
| LLLFLAILIW (114) | 10 | WB | 749.75 |
| LAILIWMYYH (115) | 10 | WB | 789.96 |
| ALYLQQNWW (116) | 9 | WB | 853.78 |
| FLAILIWMYY (117) | 10 | WB | 1515.23 |
| NSNEGRHHL (118) | 9 | WB | 12828.84 |

TCR constructs generated are characterized in Tables 2, 3 and 4 below.

TABLE 2

TCR summary

| TCR | half-maximum IFN-γ | EBV-Antigen | Epitope | SEQ ID NO: | MHC I | Recognition of tumor cells |
|---|---|---|---|---|---|---|
| 01 | $6 \times 10^{-8}$ | EBNA3C | QPRAPIRPIPT | 7 | B*07:02 | + |
| 25 | $6 \times 10^{-7}$ | EBNA3C | AEGGVGWRHW | 5 | B*44:02 | + |
| 27 | $6 \times 10^{-8}$ | EBNA3C | QPRAPIRPIP | 6 | B*07:02 | + |
| 58 | $3 \times 10^{-7}$ | EBNA3C | AEGGVGWRHW | 5 | B*44:02 | + |

TABLE 2-continued

TCR summary

| TCR | half-maximum IFN-γ | EBV-Antigen | Epitope | SEQ ID NO: | MHC I | Recognition of tumor cells |
|---|---|---|---|---|---|---|
| 64 | $7 \times 10^{-6}$ | EBNA3C | FRKAQIQGL | 4 | C*06:02 | + |
| 50 | $3 \times 10^{-8}$ | LMP1 | IALYLQQNW | 2 | B*57:01 | + |
| 83 | $2 \times 10^{-9}$ | LMP1 | QQNWWTLLV | 3 | C*15:02 | + |
| 06 | $6 \times 10^{-9}$ | LMP2A | CLGGLLTMV | 1 | A*02:01 | + |

TCR06, TCR50 and TCR83 have a high peptide sensitivity (half maximum IFN-γ release), in particular, TCR06.

TABLE 3

CDR sequences of preferred TCR constructs of the invention. CDR1 IMGT aa location: 27-38. CDR2 IMGT aa location: 56-65. CDR3 IMGT aa location: 105-117. Numbers in parentheses: SEQ ID NO:

| TCR | | CDR-1 aa seq | CDR-2 aa seq | CDR-3 aa seq |
|---|---|---|---|---|
| TCR 06 | TRA | DSAIYN (11) | IQSSQRE (12) | AVLMDSNYQLI (13) |
| | TRB | WSHSY (16) | SAAADI (17) | ASSEDGMNTEAF (18) |
| TCR 50 | TRA | SSYSPS (21) | YTSAATLV (22) | VVMATGFQKLV (23) |
| | TRB | SGDLS (26) | YYNGEE (27) | ASSVTSGSDEQF (28) |
| TCR 83 | TRA | TSGFNG (31) | NVLDGL (32) | AAVNNAGNMLT (33) |
| | TRB | LGHDT (36) | YNNKEL (37) | ASSQGYGGPSTDTQY (38) |
| TCR 64 | TRA | SVFSS (41) | VVTGGEV (42) | AGDVDTGTASKLT (43) |
| | TRB | MDHEN (46) | SYDVKM (47) | ASSLLGSGALYEQY (48) |
| TCR 25 | TRA | SSYSPS (51) | YTSAATLV (52) | VAWDTGFQKLV (53) |
| | TRB | SNHLY (56) | FYNNEI (57) | ASKALADTQY (58) |
| TCR 58 | TRA | NSASQS (61) | VYSSGN (62) | VASGDSSYKLI (63) |
| | TRB | SNHLY (66) | FYNNEI (67) | ASSDPLSTYNEQF (68) |
| TCR 27 | TRA | TISGTDY (71) | GLTSN (72) | ILCGAGGTSYGKLT (73) |
| | TRB | MNHEY (76) | SMNVEV (77) | ASNVQGANNEQF (78) |
| TCR 01 | TRA | TISGTDY (81) | GLTSN (82) | ILCGAGGTSYGKLT (83) |
| | TRB | MNHEY (86) | SMNVEV (87) | ASAIQGANNEQF (88) |

TABLE 4

TRAV and TRBV segments and junction aa (IMGT
location 104-118) of preferred TCR constructs
of the invention. Numbers in parentheses: SEQ
ID NO:

| TCR | | V segment | aa junction aa seq |
|-----|-----|-----------|--------------------|
| TCR 06 | TRA | TRAV21*01 | CAVLMDSNYQLIW (14) |
| | TRB | TRBV10-2*02 | CASSEDGMNTEAFF (19) |
| TCR 50 | TRA | TRAV8-2*01 | CVVMATGFQKLVF (24) |
| | TRB | TRBV9*01 | CASSVTSGSDEQFF (29) |
| TCR 83 | TRA | TRAV1-2*01 | CAAVNNAGNMLTF (34) |
| | TRB | TRBV3-1*01 | CASSQGYGGPSTDTQYF (39) |
| TCR 64 | TRA | TRAV27*01 | CAGDVDTGTASKLTF (44) |
| | TRB | TRBV28*01 | CASSLLGSGALYEQYF (49) |
| TCR 25 | TRA | TRAV8-2*01 | CVAWDTGFQKLVF (54) |
| | TRB | TRBV2*01 | CASKALADTQYF (59) |
| TCR 58 | TRA | TRAV12-1*01 | CVASGDSSYKLIF (64) |
| | TRB | TRBV2*01 | CASSDPLSTYNEQFF (69) |
| TCR 27 | TRA | TRAV26-2*01 | CILCGAGGTSYGKLTF (74) |
| | TRB | TRBV27*01 | CASNVQGANNEQFF (79) |
| TCR 01 | TRA | TRAV26-2*01 | CILCGAGGTSYGKLTF (84) |
| | TRB | TRBV27*01 | CASAIQGANNEQFF (89) |

Functional Characterization

The generated TCR-engineered T cells were functionally characterized using in vitro assays.

Firstly, the peptide sensitivity (half maximum IFN-γ release) of the isolated TCRs was analyzed in peptide titration experiments (cf. FIG. 6 and Lorenz et al., 2018). Briefly, peptides were loaded in titrating amounts onto K562 target cells, ranging from $10^{-5}$ mol/l to $10^{-13}$ mol/l. A co-culture assay was performed with TCR-engineered T cells at an effector to target (E:T) cell ratio of 1:1 (if not otherwise indicated), meaning $2.5 \times 10^4$ TCR-engineered T cells were co-cultured with $2.5 \times 10^4$ peptide-loaded K562 cells. The ability of TCR-transduced T cells to recognize their target epitope was assessed after 24 h by an IFN-γ ELISA.

Secondly, EBV antigen-expressing target cell lines (LCLs, EBV-associated cancer cell lines which endogenously process and present EBV epitopes and peptide-loaded K562 cells) were applied in co-culture experiments to determine the amount of IFN-γ released by TCR-engineered T cells (cf. FIG. 7 and Lorenz et al., 2018). In brief, TCR-engineered T cells and target cells (each $2 \times 10^4$) were co-cultured. After 24 h, T cell reactivity was determined by measuring the amount of secreted IFN-γ by ELISA. T cells stimulated with PMA and ionomycin were used as positive control, untransduced T cells as negative control.

According to the described isolation and characterization procedure and the identification of the epitopes recognized by TCR-engineered T cells, we have isolated in total eight EBV-specific TCRs, and the relevant, immunogenic peptides (epitopes) recognized by these TCRs. Some of the epitopes were already known in the art, others, in particular, peptides of SEQ ID NO: 3, 4 and 5, have been newly identified herein to be presented by the respective MHC I molecules.

Thirdly, EBV antigen-expressing L591 tumor cells which endogenously process and present epitopes of LMP1, LMP2A, and EBNA3C but where transfected with the relevant MHC I alleles were applied in co-culture experiments with TCR-engineered T cells to determine the killing capacity of TCR-engineered T cells.

Furthermore, the generated TCR-engineered T cells were functionally characterized using in vivo assays. Therefore, two models of immunocompromised mice (NOD, NSG) were applied. Tumor cells expressing both the relevant EBV antigen and MHC I molecule were injected subcutaneously into the animals and TCR-engineered T cells were transferred by tail vein injection into the mice.

Combination of TCRs for Immunotherapy

The combination of TCR-engineered T cells which recognize different epitopes presented by distinct MHC I molecules is an interesting option to improve TCR gene therapy. This approach aims to overcome and prevent two problems of immunotherapy: (i) tumor outgrowth due to loss variants of a specific tumor antigen and (ii) tumor immune evasion due to downregulation of a specific MHC I molecule. Using such a combinatorial approach, the efficiency of TCR gene therapy will be enhanced.

To prove this concept, two or three TCRs, which are able to recognize endogenously processed EBV antigens naturally presented by different MHC I molecules, are selected, e.g. TCR06 (LMP2A, MHC A*02:01), TCR50 (LMP1, MHC B*57:01), and, optionally, TCR64 (EBNA3C, MHC C*06:02). TCR-engineered T cells are generated with these TCRs by retroviral transduction as described. Tumor cells which naturally express the EBV antigens recognized by the TCR and which harbor the respective MHC I molecules (A*02:01, B*57:01, C*06:02) are used in co-culture experiments with TCR-engineered T cells.

Alternatively, such cells (e.g. K562 cells) are generated by transfection of the corresponding EBV antigen genes and the MHC I genes.

In the experiment, TCR-engineered T cells are used individually or in combinations, and will be co-cultured with tumor cells in an E:T ration of 2:1. To evaluate the effectiveness of the single and combinatorial application of TCR-engineered T cells, IFN-γ secretion is determined by ELISA.

In addition, a cytotoxicity assay is used to analyze the capacity of the single and combinatorial application of TCR-engineered T cells to kill tumor cells.

In a further experiment, an in vivo mouse model is established. Tumor cells, e.g. K562 cells, expressing the respective EBV antigens and MHC I molecules, are s.c. injected into the flank of NSG mice (NOD.Cg-Prkdc$^{scid}$ Il2rg$^{tm1 \ Wjl}$/Sz). After tumors are palpable, TCR-engineered T cells are i.v. injected, individually or in combination, to determine the efficacy of TCR gene therapy in terms of tumor rejection.

REFERENCES

Chervin et al., 2008. Journal of Immunological Methods 339: 175-184.

Cho et al., 2018. British Journal of Cancer 118: 534-545.

Cohen et al., 2006. Cancer Research 66: 8878-8886.

Cohen et al., 2007. Cancer Research 67: 3898-3903.

Danska et al., 1990. The Journal of Experimental Medicine 172: 27-33.

Doran et al., 2019. Journal of Clinical Oncology doi: 10.1200/JCO.18.02424. [Epub ahead of print].

Engels et al., 2003. Human Gene Therapy 14: 1155-1168.

Garcia and Adams, 2005. Cell 122: 333-336.

Hart et al., 2008. Gene Therapy 15: 625-631.

Jurgens et al., 2006. Journal of Clinical Immunology 26: 22-32.

Kuball et al., 2007. Blood 109: 2331-2338.

Leisegang et al., 2008. Journal of Molecular Medicine. 86: 573-583.

Linette et al., 2013. Blood 122: 863-871.

Lorenz et al., 2018. Human Gene Therapy 28: 1158-1168.

Morgan et al., 2013. Journal of Immunotherapy 36: 133-151.

Orentas et al., 2001. Clinical Immunology 98: 220-228.

Robbins et al., 2008. Journal of Immunology 180: 6116-6131.

Scholten et al., 2006. Clinical Immunology 119: 135-145.

Simpson et al., 2011. Proceedings of the National Academy of Sciences of the USA 108: 21176-21181.

Sommermeyer and Uckert, 2010, Journal of Immunology 184: 6223-6231.

Tran et al., 2014. Science 344: 641-645.

WO 2011/039508 A2

WO 2015/022520 A1

Yang et al., 2011. Clinical and Developmental Immunology, Article ID 716926

Zheng et al., 2015. Cancer Immunology Research 3: 1138-1147.

The invention claimed is:

1. A nucleic acid encoding a TCR alpha chain construct (TRA) and a TCR beta chain construct (TRB) of a TCR construct specific for an epitope in complex with a human MHC I, wherein the epitope is an epitope of an Epstein-Barr-virus (EBV) protein, wherein the epitope has the sequence of SEQ ID NO: 1, the MHC I is HLA-A*02:01, and the TRA comprises a CDR1 having SEQ ID NO: 11, a CDR2 having SEQ ID NO: 12 and a CDR3 having SEQ ID NO: 13 and the TRB comprises a CDR1 having SEQ ID NO: 16, a CDR2 having SEQ ID NO: 17 and a CDR3 having SEQ ID NO: 18.

2. The nucleic acid of claim 1, wherein the TRA comprises a variable region having at least 90% sequence identity to SEQ ID NO: 15 and the TRB comprises a variable region having at least 90% sequence identity to SEQ ID NO: 20.

3. The nucleic acid of claim 1, wherein the nucleic acid is selected from the group consisting of a viral vector, a transposon, a vector suitable for CRISPR/CAS based recombination or a plasmid suitable for in vitro RNA transcription.

4. The nucleic acid of claim 3, wherein the TCR alpha chain construct and the TCR beta chain construct further comprise a constant region selected from the group consisting of a human constant region, a murine constant region or a chimeric constant region.

5. A protein encoded by the nucleic acid of claim 1, wherein the TCR alpha chain construct and the TCR beta chain construct further comprise a murine constant region or a chimeric constant region.

6. A host cell comprising the nucleic acid of claim 1.

7. A pharmaceutical composition comprising a host cell of claim 6 expressing a TCR construct capable of specifically binding to said epitope in the context of said MHC I.

8. A host cell of claim 6, wherein the host cell is a human CD8+ T cell.

9. A pharmaceutical composition comprising the nucleic acid of claim 1.

10. A pharmaceutical composition or kit comprising at least two nucleic acids, each encoding a TCR construct capable of specifically binding to its respective epitope in the context of the respective MHC I;

wherein one of said nucleic acids is the nucleic acid of claim 1.

11. The nucleic acid of claim 1, wherein a peptide links TRA and TRB chains to achieve a stoichiometric expression of both chains.

12. The nucleic acid of claim 1, wherein the nucleic acid is an expression vector.

13. A host cell comprising the nucleic acid of claim 12.

14. A nucleic acid encoding a TCR alpha chain construct (TRA) and a TCR beta chain construct (TRB) of a TCR construct specific for an epitope in complex with a human MHC I, wherein the epitope is an epitope of an Epstein-Barr-virus (EBV) protein, wherein the epitope has the sequence of SEQ ID NO: 1, the MHC I is HLA-A*02:01, and the TRA comprises a CDR1 having SEQ ID NO: 11, a CDR2 having SEQ ID NO: 12 and a CDR3 having SEQ ID NO: 13 and the TRB comprises a CDR1 having SEQ ID NO: 16, a CDR2 having SEQ ID NO: 17 and a CDR3 having SEQ ID NO: 18, wherein the TCR alpha chain construct and the TCR beta chain construct further comprise a murine constant region or a chimeric constant region.

15. A host cell comprising the nucleic acid of claim 14.

16. A nucleic acid encoding a TCR alpha chain construct (TRA) and a TCR beta chain construct (TRB) of a TCR construct specific for an epitope in complex with a human MHC I, wherein the epitope is an epitope of an Epstein-Barr-virus (EBV) protein, wherein the epitope has the sequence of SEQ ID NO: 1, the MHC I is HLA-A*02:01, and the TRA comprises a CDR1 having SEQ ID NO: 11, a CDR2 having SEQ ID NO: 12 and a CDR3 having SEQ ID NO: 13 and the TRB comprises a CDR1 having SEQ ID NO: 16, a CDR2 having SEQ ID NO: 17 and a CDR3 having SEQ ID NO: 18, wherein the nucleic acid is a recombinant expression vector and a heterologous promoter is operably linked to the nucleotide sequence encoding the TCR construct.

17. A method of treating a cancer associated with EBV or infectious agent, comprising administering to a subject having a cancer or infectious agent a pharmaceutical composition or a kit comprising at least two pharmaceutical compositions comprising a) two nucleic acids, each encoding a TCR construct capable of specifically binding to its respective epitope in the context of the respective MHC I; or b) at least two host cells, each comprising one nucleic acid encoding a TCR construct capable of specifically binding to its respective epitope in the context of the respective MHC I and expressing the TCR construct, wherein the epitopes are peptides from different antigens expressed by the EBV and the different EBV antigens are selected from the group comprising LMP2A, LMP1, EBNA1 and EBNA3C, wherein one of said nucleic acids is the nucleic acid of claim 1.

18. A method of treating a patient expressing HLA-A*02:01 and having an EBV-associated disease selected from the group consisting of Hodgkin's and non-Hodgkin lymphoma, Burkitt lymphoma, hemophagocytic lymphohistiocytosis, nasopharyngeal carcinoma, head and neck cancer, lung cancer, gastric cancer hairy leukoplakia, post transplant lymphoproliferative disorder and central nervous system lymphoma, comprising administering to said patient an effective amount of the nucleic acid of claim 1.

19. A method of treating a patient expressing HLA-A*02:01 and having an EBV-associated disease selected from the group consisting of Hodgkin's and non-Hodgkin lymphoma, Burkitt lymphoma, hemophagocytic lymphohistiocytosis, nasopharyngeal carcinoma, head and neck cancer, lung cancer, gastric cancer hairy leukoplasia, post transplant lymphoproliferative disorder and central nervous system lymphoma, comprising administering to said patient an effective amount of the host cell of claim 6.

* * * * *